United States Patent
Hamner et al.

(10) Patent No.: US 12,233,265 B2
(45) Date of Patent: Feb. 25, 2025

(54) SYSTEMS AND METHODS FOR TREATING CARDIAC DYSFUNCTION THROUGH PERIPHERAL NERVE STIMULATION

(71) Applicant: Cala Health, Inc., San Mateo, CA (US)

(72) Inventors: Samuel Richard Hamner, San Francisco, CA (US); Kathryn H. Rosenbluth, San Francisco, CA (US); Serena HanYing Wong, Palo Alto, CA (US); Erika Kristine Ross, San Mateo, CA (US)

(73) Assignee: Cala Health, Inc., San Mateo, CA (US)

( * ) Notice: Subject to any disclaimer, the term of this patent is extended or adjusted under 35 U.S.C. 154(b) by 7 days.

(21) Appl. No.: 16/327,780

(22) PCT Filed: Aug. 24, 2017

(86) PCT No.: PCT/US2017/048424
§ 371 (c)(1),
(2) Date: Feb. 22, 2019

(87) PCT Pub. No.: WO2018/039458
PCT Pub. Date: Mar. 1, 2018

(65) Prior Publication Data
US 2021/0283400 A1    Sep. 16, 2021

Related U.S. Application Data

(60) Provisional application No. 62/423,169, filed on Nov. 16, 2016, provisional application No. 62/379,253, filed on Aug. 25, 2016.

(51) Int. Cl.
*A61N 1/36*  (2006.01)
*A61N 1/04*  (2006.01)
*A61N 1/39*  (2006.01)

(52) U.S. Cl.
CPC ........ *A61N 1/36117* (2013.01); *A61N 1/0456* (2013.01); *A61N 1/0484* (2013.01); *A61N 1/36178* (2013.01); *A61N 1/395* (2013.01)

(58) Field of Classification Search
CPC . A61N 1/0456; A61N 1/36014; A61N 1/3625
See application file for complete search history.

(56) References Cited

U.S. PATENT DOCUMENTS 3,204,637 A    9/1965   Frank et al.
3,870,051 A    3/1975   Brindley
(Continued)

FOREIGN PATENT DOCUMENTS

AU    2019/250222    6/2021
AU    2017211048    3/2022
(Continued)

OTHER PUBLICATIONS

Apartis; Clinical neurophysiology in movement disorders. Handb Clin Neurol; 111; Pediatric Neurology Pt. 1; pp. 87-92;Apr. 2013.
(Continued)

*Primary Examiner* — Jennifer Pitrak McDonald
*Assistant Examiner* — Adreanne A. Arnold
(74) *Attorney, Agent, or Firm* — Knobbe, Martens, Olson & Bear, LLP

(57) ABSTRACT

Systems and methods are disclosed for the treatment and prevention of cardiac dysrhythmias and/or hypertension, and more specifically to systems and methods of treating cardiac dysrhythmias, including atrial fibrillation, as well as hypertension through noninvasive peripheral nerve stimulation.

21 Claims, 46 Drawing Sheets

(56) References Cited

U.S. PATENT DOCUMENTS

| | | | |
|---|---|---|---|
| 4,103,808 | A | 8/1978 | Hallman et al. |
| 4,300,575 | A | 11/1981 | Wilson |
| 4,458,696 | A | 7/1984 | Larimore |
| 4,461,075 | A | 7/1984 | Bailey |
| 4,539,996 | A | 9/1985 | Engel |
| 4,569,351 | A | 2/1986 | Tang |
| 4,582,049 | A | 4/1986 | Ylvisaker |
| 4,729,377 | A | 3/1988 | Granek et al. |
| 4,739,764 | A | 4/1988 | Lue et al. |
| 4,763,659 | A | 8/1988 | Dunseath, Jr. |
| 4,771,779 | A | 9/1988 | Tanagho et al. |
| 4,981,146 | A | 1/1991 | Bertolucci |
| 4,982,432 | A | 1/1991 | Clark et al. |
| 4,996,987 | A | 3/1991 | Petrofsky |
| 5,003,978 | A | 4/1991 | Dunseath, Jr. |
| 5,052,391 | A | 10/1991 | Silverstone et al. |
| 5,070,862 | A | 12/1991 | Berlant |
| 5,137,507 | A | 8/1992 | Park |
| 5,330,516 | A | 7/1994 | Nathan |
| 5,397,338 | A | 3/1995 | Grey et al. |
| 5,514,175 | A | 5/1996 | Kim et al. |
| 5,540,235 | A | 7/1996 | Wilson |
| 5,562,707 | A | 10/1996 | Prochazka et al. |
| 5,562,717 | A | 10/1996 | Tippey et al. |
| 5,573,011 | A | 11/1996 | Felsing |
| 5,575,294 | A | 11/1996 | Perry et al. |
| 5,606,968 | A | 3/1997 | Mang |
| 5,643,173 | A | 7/1997 | Welles |
| 5,775,331 | A | 7/1998 | Raymond et al. |
| 5,833,709 | A | 11/1998 | Rise et al. |
| 5,833,716 | A | 11/1998 | Bar-Or et al. |
| 5,899,922 | A | 5/1999 | Loos |
| 6,016,449 | A | 1/2000 | Fischell et al. |
| 6,076,018 | A | 6/2000 | Sturman |
| 6,081,744 | A | 6/2000 | Loos |
| 6,161,044 | A | 12/2000 | Silverstone |
| 6,178,352 | B1 * | 1/2001 | Gruzdowich ...... A61N 1/36014 607/44 |
| 6,351,674 | B2 | 2/2002 | Silverstone |
| 6,366,813 | B1 | 4/2002 | DiLorenzo |
| 6,366,814 | B1 | 4/2002 | Boveja et al. |
| 6,445,955 | B1 | 9/2002 | Michelson et al. |
| 6,449,512 | B1 | 9/2002 | Boveja |
| 6,453,204 | B1 | 9/2002 | Rhoads |
| 6,505,074 | B2 | 1/2003 | Boveja et al. |
| 6,546,290 | B1 | 4/2003 | Shloznikov |
| 6,564,103 | B2 | 5/2003 | Fischer et al. |
| 6,579,270 | B2 | 6/2003 | Sussman et al. |
| 6,652,449 | B1 | 11/2003 | Gross et al. |
| 6,678,548 | B1 | 1/2004 | Echauz et al. |
| 6,701,185 | B2 | 3/2004 | Burnett et al. |
| 6,704,603 | B1 | 3/2004 | Gesotti |
| 6,731,987 | B1 | 5/2004 | McAdams et al. |
| 6,735,474 | B1 | 5/2004 | Loeb et al. |
| 6,735,480 | B2 | 5/2004 | Giuntoli et al. |
| 6,788,976 | B2 | 9/2004 | Gesotti |
| 6,819,956 | B2 | 11/2004 | DiLorenzo |
| 6,829,510 | B2 | 12/2004 | Nathan et al. |
| 6,836,684 | B1 | 12/2004 | Rijkhoff et al. |
| 6,862,480 | B2 | 3/2005 | Cohen et al. |
| 6,892,098 | B2 | 5/2005 | Ayal et al. |
| 6,937,905 | B2 | 8/2005 | Carroll et al. |
| 6,959,215 | B2 | 10/2005 | Gliner et al. |
| 6,959,216 | B2 | 10/2005 | Faghri |
| 6,988,005 | B2 | 1/2006 | McGraw et al. |
| 7,010,352 | B2 | 3/2006 | Hogan |
| 7,089,061 | B2 | 8/2006 | Grey |
| 7,146,220 | B2 | 12/2006 | Dar et al. |
| 7,162,305 | B2 | 1/2007 | Tong et al. |
| 7,171,266 | B2 | 1/2007 | Gruzdowich et al. |
| 7,177,694 | B2 | 2/2007 | Elbaum |
| 7,177,703 | B2 | 2/2007 | Boveja et al. |
| 7,209,787 | B2 | 4/2007 | DiLorenzo |
| 7,228,178 | B2 | 6/2007 | Carrol et al. |
| 7,231,254 | B2 | 6/2007 | DiLorenzo |
| 7,236,830 | B2 | 6/2007 | Gliner |
| 7,254,444 | B2 | 8/2007 | Moore et al. |
| 7,277,758 | B2 | 10/2007 | DiLorenzo |
| 7,324,851 | B1 | 1/2008 | DiLorenzo |
| 7,326,235 | B2 | 2/2008 | Edwards |
| 7,328,068 | B2 | 2/2008 | Spinelli et al. |
| 7,349,739 | B2 | 3/2008 | Harry et al. |
| 7,353,064 | B2 | 4/2008 | Gliner et al. |
| 7,369,896 | B2 | 5/2008 | Gesotti |
| 7,499,747 | B2 | 3/2009 | Kieval et al. |
| 7,529,582 | B1 | 5/2009 | DiLorenzo |
| 7,558,610 | B1 | 7/2009 | Odderson |
| 7,636,602 | B2 | 12/2009 | Baru Fassio et al. |
| 7,643,880 | B2 | 1/2010 | Tanagho et al. |
| 7,643,882 | B2 | 1/2010 | Boston |
| 7,647,112 | B2 | 1/2010 | Tracey et al. |
| 7,650,190 | B2 | 1/2010 | Zhou et al. |
| 7,657,317 | B2 | 2/2010 | Thacker et al. |
| 7,742,820 | B2 | 6/2010 | Wyler et al. |
| 7,761,166 | B2 | 7/2010 | Giftakis et al. |
| 7,769,464 | B2 | 8/2010 | Gerber et al. |
| 7,857,771 | B2 | 12/2010 | Alwan et al. |
| 7,899,527 | B2 | 3/2011 | Yun et al. |
| 7,899,556 | B2 | 3/2011 | Nathan et al. |
| 7,917,201 | B2 | 3/2011 | Gozani et al. |
| 7,930,034 | B2 | 4/2011 | Gerber |
| 7,949,403 | B2 | 5/2011 | Palermo et al. |
| 7,957,814 | B2 | 6/2011 | Goetz et al. |
| 7,974,696 | B1 | 7/2011 | DiLorenzo |
| 7,974,698 | B2 | 7/2011 | Tass et al. |
| 7,991,476 | B2 | 8/2011 | Nachum |
| 7,996,088 | B2 | 8/2011 | Marrosu et al. |
| 7,998,092 | B2 | 8/2011 | Avni et al. |
| 8,000,796 | B2 | 8/2011 | Tass et al. |
| 8,025,632 | B2 | 9/2011 | Einarsson |
| 8,046,083 | B2 | 10/2011 | Tegenthoff et al. |
| 8,075,499 | B2 | 12/2011 | Nathan et al. |
| 8,086,318 | B2 | 12/2011 | Strother et al. |
| 8,121,694 | B2 | 2/2012 | Molnar et al. |
| 8,145,316 | B2 | 3/2012 | Deem et al. |
| 8,165,668 | B2 | 4/2012 | Dacey, Jr. et al. |
| 8,165,685 | B1 | 4/2012 | Knutson et al. |
| 8,170,658 | B2 | 5/2012 | Dacey, Jr. et al. |
| 8,175,718 | B2 | 5/2012 | Wahlgren et al. |
| 8,187,209 | B1 | 5/2012 | Guiffrida et al. |
| 8,190,249 | B1 | 5/2012 | Gharieb et al. |
| 8,195,287 | B2 | 6/2012 | Dacey, Jr. et al. |
| 8,209,036 | B2 | 6/2012 | Nathan et al. |
| 8,219,188 | B2 | 7/2012 | Craig |
| 8,233,988 | B2 | 7/2012 | Errico et al. |
| 8,260,439 | B2 | 9/2012 | Diubaldi et al. |
| 8,265,763 | B2 | 9/2012 | Fahey |
| 8,301,215 | B2 | 10/2012 | Lee |
| 8,306,624 | B2 | 11/2012 | Gerber et al. |
| 8,308,665 | B2 | 11/2012 | Harry et al. |
| 8,313,443 | B2 | 11/2012 | Tom |
| 8,326,432 | B2 | 12/2012 | Kalisek |
| 8,343,026 | B2 | 1/2013 | Gardiner et al. |
| 8,364,257 | B2 | 1/2013 | Van Den Eerenbeemd et al. |
| 8,374,701 | B2 | 2/2013 | Hyde et al. |
| 8,380,314 | B2 | 2/2013 | Panken et al. |
| 8,382,688 | B2 | 2/2013 | Dar et al. |
| 8,391,970 | B2 | 3/2013 | Tracey et al. |
| 8,396,556 | B2 | 3/2013 | Libbus et al. |
| 8,406,841 | B2 | 3/2013 | Lin et al. |
| 8,409,116 | B2 | 4/2013 | Wang et al. |
| 8,412,338 | B2 | 4/2013 | Faltys |
| 8,414,507 | B2 | 4/2013 | Asada |
| 8,417,351 | B2 | 4/2013 | Kilger |
| 8,428,719 | B2 | 4/2013 | Napadow |
| 8,430,805 | B2 | 4/2013 | Burnett et al. |
| 8,435,166 | B2 | 5/2013 | Burnett et al. |
| 8,447,411 | B2 | 5/2013 | Skelton et al. |
| 8,452,410 | B2 | 5/2013 | Emborg et al. |
| 8,463,374 | B2 | 6/2013 | Hudson et al. |
| 8,473,064 | B2 | 6/2013 | Castel et al. |
| 8,548,594 | B2 | 10/2013 | Thimineur et al. |
| 8,571,687 | B2 | 10/2013 | Libbus et al. |
| 8,581,731 | B2 | 11/2013 | Purks et al. |

(56) References Cited

U.S. PATENT DOCUMENTS

| | | |
|---|---|---|
| 8,583,238 B1 | 11/2013 | Heldman et al. |
| 8,588,884 B2 | 11/2013 | Hegde et al. |
| 8,588,917 B2 | 11/2013 | Whitehurst et al. |
| 8,608,671 B2 | 12/2013 | Kinoshita et al. |
| 8,626,305 B2 | 1/2014 | Nielsen et al. |
| 8,639,342 B2 | 1/2014 | Possover |
| 8,644,904 B2 | 2/2014 | Chang et al. |
| 8,644,938 B2 | 2/2014 | Craggs |
| 8,660,656 B2 | 2/2014 | Moser et al. |
| 8,666,496 B2 | 3/2014 | Simon et al. |
| 8,679,038 B1 | 3/2014 | Giuffrida |
| 8,682,441 B2 | 3/2014 | De Ridder |
| 8,688,220 B2 | 4/2014 | Degiorgio et al. |
| 8,694,104 B2 | 4/2014 | Libbus et al. |
| 8,694,110 B2 | 4/2014 | Nathan et al. |
| 8,702,584 B2 | 4/2014 | Rigaux et al. |
| 8,702,629 B2 | 4/2014 | Giuffrida et al. |
| 8,706,241 B2 | 4/2014 | Firlik et al. |
| 8,718,780 B2 | 5/2014 | Lee |
| 8,738,143 B2 | 5/2014 | Tucker et al. |
| 8,740,825 B2 | 6/2014 | Ehrenreich et al. |
| 8,744,587 B2 | 6/2014 | Miesel et al. |
| 8,755,892 B2 | 6/2014 | Amurthur et al. |
| 8,768,452 B2 | 7/2014 | Gerber |
| 8,788,045 B2 | 7/2014 | Gross et al. |
| 8,788,049 B2 | 7/2014 | Lasko et al. |
| 8,792,977 B2 | 7/2014 | Kakei et al. |
| 8,798,698 B2 | 8/2014 | Kim et al. |
| 8,821,416 B2 | 9/2014 | Johansson et al. |
| 8,825,163 B2 | 9/2014 | Grill et al. |
| 8,825,165 B2 | 9/2014 | Possover |
| 8,843,201 B1 | 9/2014 | Heldman et al. |
| 8,845,494 B2 | 9/2014 | Whitall et al. |
| 8,845,557 B1 | 9/2014 | Giuffrida et al. |
| 8,855,775 B2 | 10/2014 | Leyde |
| 8,862,238 B2 | 10/2014 | Rahimi et al. |
| 8,862,247 B2 | 10/2014 | Schoendorf et al. |
| 8,868,177 B2 | 10/2014 | Simon et al. |
| 8,874,227 B2 | 10/2014 | Simon et al. |
| 8,880,175 B2 | 11/2014 | Simon |
| 8,886,321 B2 | 11/2014 | Rohrer et al. |
| 8,892,200 B2 | 11/2014 | Wagner et al. |
| 8,897,870 B2 | 11/2014 | De Ridder |
| 8,903,494 B2 | 12/2014 | Goldwasser et al. |
| 8,920,345 B2 | 12/2014 | Greenberg et al. |
| 8,923,970 B2 | 12/2014 | Bar-Yoseph et al. |
| 8,948,876 B2 | 2/2015 | Gozani et al. |
| 8,961,439 B2 | 2/2015 | Yang et al. |
| 8,972,017 B2 | 3/2015 | Dar et al. |
| 8,989,861 B2 | 3/2015 | Su et al. |
| 9,002,477 B2 | 4/2015 | Burnett |
| 9,005,102 B2 | 4/2015 | Burnett et al. |
| 9,008,781 B2 | 4/2015 | Ahmed |
| 9,011,310 B2 | 4/2015 | Ahmed |
| 9,017,273 B2 | 4/2015 | Burbank et al. |
| 9,026,216 B2 | 5/2015 | Rossi et al. |
| 9,042,988 B2 | 5/2015 | Dilorenzo |
| 9,060,747 B2 | 6/2015 | Salorio |
| 9,089,691 B2 | 7/2015 | Libbus et al. |
| 9,095,351 B2 | 8/2015 | Sachs et al. |
| 9,095,417 B2 | 8/2015 | Dar et al. |
| 9,107,614 B2 | 8/2015 | Halkias et al. |
| 9,119,964 B2 | 9/2015 | Marnfeldt |
| 9,155,885 B2 | 10/2015 | Wei et al. |
| 9,155,890 B2 | 10/2015 | Guntinas-Lichius et al. |
| 9,162,059 B1 | 10/2015 | Lindenthaler |
| 9,168,374 B2 | 10/2015 | Su |
| 9,174,045 B2 | 11/2015 | Simon et al. |
| 9,186,095 B2 | 11/2015 | Machado et al. |
| 9,192,763 B2 | 11/2015 | Gerber et al. |
| 9,220,431 B2 | 12/2015 | Holzhacker |
| 9,220,895 B2 | 12/2015 | Siff et al. |
| 9,227,056 B1 | 1/2016 | Heldman et al. |
| 9,238,137 B2 | 1/2016 | Einav et al. |
| 9,238,142 B2 | 1/2016 | Heldman et al. |
| 9,242,085 B2 | 1/2016 | Hershey et al. |
| 9,248,285 B2 | 2/2016 | Haessler |
| 9,248,286 B2 | 2/2016 | Simon et al. |
| 9,248,297 B2 | 2/2016 | Hoyer et al. |
| 9,254,382 B2 | 2/2016 | Ahmad et al. |
| 9,259,577 B2 | 2/2016 | Kaula et al. |
| 9,265,927 B2 | 2/2016 | Yonce et al. |
| 9,282,928 B1 | 3/2016 | Giffrida |
| 9,289,607 B2 | 3/2016 | Su et al. |
| 9,301,712 B2 | 4/2016 | McNames et al. |
| 9,302,046 B1 | 4/2016 | Giuffrida et al. |
| 9,311,686 B2 | 4/2016 | Roush et al. |
| 9,314,190 B1 | 4/2016 | Giuffrida et al. |
| 9,314,622 B2 | 4/2016 | Embrey et al. |
| 9,332,918 B1 | 5/2016 | Buckley et al. |
| 9,339,213 B2 | 5/2016 | Otsamo et al. |
| 9,339,641 B2 | 5/2016 | Rajguru et al. |
| 9,345,872 B2 | 5/2016 | Groteke |
| 9,364,657 B2 | 6/2016 | Kiani et al. |
| 9,364,672 B2 | 6/2016 | Marnfeldt |
| 9,375,570 B2 | 6/2016 | Kiani et al. |
| 9,387,338 B2 | 7/2016 | Burnett |
| 9,393,430 B2 | 7/2016 | Demers et al. |
| 9,408,683 B2 | 8/2016 | St. Anne et al. |
| 9,414,776 B2 | 8/2016 | Sillay et al. |
| 9,415,205 B2 | 8/2016 | Lasko et al. |
| 9,452,287 B2 | 9/2016 | Rosenbluth et al. |
| 9,468,753 B2 | 10/2016 | Fisher et al. |
| 9,474,898 B2 | 10/2016 | Gozani et al. |
| 9,549,872 B2 | 1/2017 | Chen et al. |
| 9,581,972 B1 | 2/2017 | Arrow et al. |
| 9,586,038 B1 | 3/2017 | Kosierkiewicz |
| 9,589,698 B2 | 3/2017 | Anhalt et al. |
| 9,597,509 B2 | 3/2017 | Hoffer et al. |
| 9,610,442 B2 | 4/2017 | Yoo et al. |
| 9,610,459 B2 | 4/2017 | Burnett et al. |
| 9,615,797 B2 | 4/2017 | John |
| 9,630,004 B2 | 4/2017 | Rajguru et al. |
| 9,649,486 B2 | 5/2017 | Holzhacker |
| 9,656,070 B2 | 5/2017 | Gozani et al. |
| 9,669,211 B2 | 6/2017 | Wijting et al. |
| 9,675,800 B2 | 6/2017 | Li et al. |
| 9,675,801 B2 | 6/2017 | Kong et al. |
| 9,707,393 B2 | 7/2017 | Hsueh et al. |
| 9,731,126 B2 | 8/2017 | Ferree et al. |
| 9,757,584 B2 | 9/2017 | Burnett |
| 9,782,584 B2 | 10/2017 | Cartledge et al. |
| 9,802,041 B2 | 10/2017 | Wong et al. |
| 9,861,283 B1 | 1/2018 | Giuffrida |
| 9,877,679 B1 | 1/2018 | Giuffrida |
| 9,877,680 B1 | 1/2018 | Giuffrida et al. |
| 9,884,179 B2 | 2/2018 | Bouton et al. |
| 9,924,899 B2 | 3/2018 | Pracar et al. |
| 9,956,395 B2 | 5/2018 | Bikson et al. |
| 9,974,478 B1 | 5/2018 | Brokaw et al. |
| 9,980,659 B2 | 5/2018 | Sadeghian-Motahar et al. |
| 9,992,918 B2 | 6/2018 | Watanabe et al. |
| 10,004,900 B2 | 6/2018 | Kent et al. |
| 10,016,600 B2 | 7/2018 | Creasey et al. |
| 10,022,545 B1 | 7/2018 | Giuffrida |
| 10,028,695 B2 | 7/2018 | Machado et al. |
| 10,045,740 B2 | 8/2018 | John |
| 10,046,161 B2 | 8/2018 | Biasiucci et al. |
| 10,076,656 B2 | 9/2018 | Dar et al. |
| 10,080,885 B2 | 9/2018 | Nathan et al. |
| 10,112,040 B2 | 10/2018 | Herb et al. |
| 10,118,035 B2 | 11/2018 | Perez et al. |
| 10,130,809 B2 | 11/2018 | Cartledge et al. |
| 10,130,810 B2 | 11/2018 | Ferree et al. |
| 10,137,025 B2 | 11/2018 | Fior et al. |
| 10,173,060 B2 | 1/2019 | Wong et al. |
| 10,179,238 B2 | 1/2019 | Wong et al. |
| 10,213,593 B2 | 2/2019 | Kaplan et al. |
| 10,213,602 B2 | 2/2019 | Ironi et al. |
| 10,232,174 B2 | 3/2019 | Simon et al. |
| 10,252,053 B2 | 4/2019 | Page et al. |
| 10,285,646 B1 | 5/2019 | Grant et al. |
| 10,286,210 B2 | 5/2019 | Yoo et al. |
| 10,293,159 B2 | 5/2019 | Kong et al. |

(56) References Cited

U.S. PATENT DOCUMENTS

| | | |
|---|---|---|
| 10,335,594 B2 | 7/2019 | Lin et al. |
| 10,335,595 B2 | 7/2019 | Ferree et al. |
| 10,342,977 B2 | 7/2019 | Raghunathan |
| 10,398,896 B2 | 9/2019 | Lin et al. |
| 10,456,573 B1 | 10/2019 | Feinstein et al. |
| 10,463,854 B2 | 11/2019 | Perez |
| 10,500,396 B2 | 12/2019 | Tamaki et al. |
| 10,537,732 B2 | 1/2020 | Nachum et al. |
| 10,549,093 B2 | 2/2020 | Wong et al. |
| 10,556,107 B2 | 2/2020 | Yoo et al. |
| 10,561,839 B2 | 2/2020 | Wong et al. |
| 10,603,482 B2 | 3/2020 | Hamner et al. |
| 10,610,114 B2 | 4/2020 | Buckley et al. |
| 10,625,074 B2 | 4/2020 | Rosenbluth et al. |
| 10,632,312 B2 | 4/2020 | Ziv |
| 10,661,082 B2 | 5/2020 | Kerselaers |
| 10,722,709 B2 | 7/2020 | Yoo et al. |
| 10,765,856 B2 | 9/2020 | Wong et al. |
| 10,773,079 B2 | 9/2020 | Keller et al. |
| 10,780,269 B2 | 9/2020 | Gozani et al. |
| 10,786,669 B2 | 9/2020 | Rajguru et al. |
| 10,814,130 B2 | 10/2020 | Wong et al. |
| 10,814,131 B2 | 10/2020 | Goldwasser et al. |
| 10,835,736 B2 | 11/2020 | Horter et al. |
| 10,850,090 B2 | 12/2020 | Rosenbluth et al. |
| 10,870,002 B2 | 12/2020 | Wybo et al. |
| 10,905,879 B2 | 2/2021 | Wong et al. |
| 10,918,853 B2 | 2/2021 | Creasey et al. |
| 10,940,311 B2 | 3/2021 | Gozani et al. |
| 10,945,879 B2 | 3/2021 | Black et al. |
| 10,960,207 B2 | 3/2021 | Wong et al. |
| 10,967,177 B2 | 4/2021 | Lee |
| 11,026,835 B2 | 6/2021 | Black et al. |
| 11,033,206 B2 | 6/2021 | Roh |
| 11,033,731 B2 | 6/2021 | Jeffery et al. |
| 11,033,736 B2 | 6/2021 | Edgerton et al. |
| 11,058,867 B2 | 7/2021 | Nathan et al. |
| 11,077,300 B2 | 8/2021 | McBride |
| 11,077,301 B2 | 8/2021 | Creasey et al. |
| 11,103,699 B1 | 8/2021 | Oppenheim et al. |
| 11,141,586 B2 | 10/2021 | Campean et al. |
| 11,141,587 B2 | 10/2021 | Campean et al. |
| 11,160,971 B2 | 11/2021 | Sharma et al. |
| 11,213,681 B2 | 1/2022 | Raghunathan |
| 11,224,742 B2 | 1/2022 | Burnett |
| 11,247,040 B2 | 2/2022 | Ferree et al. |
| 11,247,053 B2 | 2/2022 | Rajguru et al. |
| 11,266,836 B2 | 3/2022 | Charlesworth et al. |
| 11,331,480 B2 | 5/2022 | Hamner et al. |
| 11,344,722 B2 | 5/2022 | Wong et al. |
| 11,357,981 B2 | 6/2022 | Moaddeb et al. |
| 11,596,785 B2 | 3/2023 | Hamner et al. |
| 11,596,791 B2 | 3/2023 | Wong et al. |
| 11,628,300 B2 | 4/2023 | Rajguru et al. |
| 11,857,778 B2 | 1/2024 | Hamner et al. |
| 11,890,468 B1 | 2/2024 | Yu |
| 11,918,806 B2 | 3/2024 | Wong et al. |
| 2001/0020177 A1* | 9/2001 | Gruzdowich ...... A61N 1/36014 607/44 |
| 2002/0055761 A1 | 5/2002 | Mann et al. |
| 2002/0161415 A1 | 10/2002 | Cohen et al. |
| 2002/0165586 A1* | 11/2002 | Hill ..................... A61N 1/36114 607/9 |
| 2002/0177882 A1 | 11/2002 | DiLorenzo |
| 2003/0032992 A1 | 2/2003 | Thacker et al. |
| 2003/0045922 A1 | 3/2003 | Northrop |
| 2003/0088294 A1 | 5/2003 | Gesotti |
| 2003/0093098 A1 | 5/2003 | Heitzmann et al. |
| 2003/0149457 A1 | 8/2003 | Tcheng et al. |
| 2003/0181959 A1 | 9/2003 | Dobak, III |
| 2003/0187483 A1 | 10/2003 | Grey et al. |
| 2003/0195583 A1 | 10/2003 | Gruzdowich et al. |
| 2004/0015094 A1 | 1/2004 | Manabe et al. |
| 2004/0088025 A1 | 5/2004 | Gessotti |
| 2004/0093093 A1 | 5/2004 | Andrews |
| 2004/0102819 A1 | 5/2004 | Zou et al. |
| 2004/0127939 A1 | 7/2004 | Grey et al. |
| 2004/0133249 A1 | 7/2004 | Gesotti |
| 2004/0167588 A1 | 8/2004 | Bertolucci |
| 2004/0249416 A1 | 12/2004 | Yun et al. |
| 2004/0267331 A1 | 12/2004 | Koeneman et al. |
| 2005/0021103 A1 | 1/2005 | DiLorenzo |
| 2005/0055063 A1 | 3/2005 | Loeb et al. |
| 2005/0060009 A1 | 3/2005 | Geotz |
| 2005/0065553 A1 | 3/2005 | Ben Ezra et al. |
| 2005/0075502 A1 | 4/2005 | Shafer |
| 2005/0171576 A1 | 8/2005 | Williams et al. |
| 2005/0171577 A1 | 8/2005 | Cohen et al. |
| 2005/0182454 A1 | 8/2005 | Gharib et al. |
| 2005/0222626 A1 | 10/2005 | DiLorenzo |
| 2005/0234309 A1 | 10/2005 | Klapper |
| 2005/0240241 A1 | 10/2005 | Yun et al. |
| 2006/0015153 A1 | 1/2006 | Gliner et al. |
| 2006/0047326 A1 | 3/2006 | Wheeler |
| 2006/0052726 A1 | 3/2006 | Weisz et al. |
| 2006/0074450 A1 | 4/2006 | Boveja et al. |
| 2006/0095088 A1 | 5/2006 | De Ridder |
| 2006/0161218 A1 | 7/2006 | Danilov |
| 2006/0173509 A1 | 8/2006 | Lee et al. |
| 2006/0184059 A1 | 8/2006 | Jadidi |
| 2006/0217781 A1 | 9/2006 | John |
| 2006/0224191 A1 | 10/2006 | DiLorenzo |
| 2006/0229678 A1 | 10/2006 | Lee |
| 2006/0253167 A1 | 11/2006 | Kurtz et al. |
| 2006/0276853 A1 | 12/2006 | Tass |
| 2006/0293723 A1 | 12/2006 | Whitehurst et al. |
| 2007/0027486 A1 | 2/2007 | Armstrong |
| 2007/0073361 A1 | 3/2007 | Goren et al. |
| 2007/0123951 A1 | 5/2007 | Boston |
| 2007/0123952 A1 | 5/2007 | Strother et al. |
| 2007/0142862 A1 | 6/2007 | DiLorenzo |
| 2007/0156179 A1 | 7/2007 | Karashurov |
| 2007/0156182 A1 | 7/2007 | Castel et al. |
| 2007/0156183 A1 | 7/2007 | Rhodes |
| 2007/0156200 A1 | 7/2007 | Kornet et al. |
| 2007/0173899 A1 | 7/2007 | Levin et al. |
| 2007/0173903 A1 | 7/2007 | Goren et al. |
| 2007/0203533 A1 | 8/2007 | Goren et al. |
| 2007/0203534 A1 | 8/2007 | Tapper |
| 2007/0207193 A1 | 9/2007 | Zasler et al. |
| 2007/0249952 A1 | 10/2007 | Rubin et al. |
| 2007/0255319 A1 | 11/2007 | Greenberg et al. |
| 2007/0276217 A1 | 11/2007 | Brown et al. |
| 2007/0282228 A1 | 12/2007 | Einav et al. |
| 2008/0004672 A1 | 1/2008 | Dalal et al. |
| 2008/0009772 A1 | 1/2008 | Tyler et al. |
| 2008/0021505 A1 | 1/2008 | Hastings et al. |
| 2008/0027507 A1 | 1/2008 | Bijelic et al. |
| 2008/0030170 A1 | 2/2008 | Dacuay et al. |
| 2008/0033259 A1 | 2/2008 | Manto et al. |
| 2008/0033504 A1 | 2/2008 | Bertolucci |
| 2008/0051839 A1 | 2/2008 | Libbus et al. |
| 2008/0051845 A1 | 2/2008 | Mentelos |
| 2008/0058773 A1 | 3/2008 | John |
| 2008/0058871 A1 | 3/2008 | Libbus et al. |
| 2008/0058893 A1 | 3/2008 | Noujokat |
| 2008/0097564 A1 | 4/2008 | Lathrop |
| 2008/0147146 A1 | 6/2008 | Wahlgren et al. |
| 2008/0177398 A1 | 7/2008 | Gross et al. |
| 2008/0195007 A1 | 8/2008 | Podrazhansky et al. |
| 2008/0208282 A1 | 8/2008 | Gelfand et al. |
| 2008/0208288 A1 | 8/2008 | Podrazhansky et al. |
| 2008/0216593 A1 | 9/2008 | Jacobsen et al. |
| 2008/0243204 A1 | 10/2008 | Uthman et al. |
| 2008/0288016 A1* | 11/2008 | Amurthur ............ A61B 5/6826 607/44 |
| 2008/0300449 A1 | 12/2008 | Gerber et al. |
| 2008/0306325 A1 | 12/2008 | Burnett et al. |
| 2008/0312520 A1 | 12/2008 | Rowlandson et al. |
| 2009/0018609 A1 | 1/2009 | DiLorenzo |
| 2009/0076565 A1 | 3/2009 | Surwit |
| 2009/0082831 A1 | 3/2009 | Paul et al. |
| 2009/0099623 A1 | 4/2009 | Bentwich |
| 2009/0105785 A1 | 4/2009 | Wei et al. |

(56) References Cited

U.S. PATENT DOCUMENTS

| | | |
|---|---|---|
| 2009/0112133 A1 | 4/2009 | Deisseroth et al. |
| 2009/0157138 A1 | 6/2009 | Errico et al. |
| 2009/0187121 A1 | 7/2009 | Evans |
| 2009/0216294 A1 | 8/2009 | Ewing et al. |
| 2009/0222053 A1 | 9/2009 | Gaunt et al. |
| 2009/0247910 A1 | 10/2009 | Klapper |
| 2009/0249617 A1 | 10/2009 | Karicherla et al. |
| 2009/0299435 A1 | 12/2009 | Gliner et al. |
| 2009/0312690 A1 | 12/2009 | Kim et al. |
| 2009/0318986 A1 | 12/2009 | Alo et al. |
| 2009/0326595 A1 | 12/2009 | Brockway et al. |
| 2009/0326607 A1 | 12/2009 | Castel et al. |
| 2010/0004715 A1 | 1/2010 | Fahey |
| 2010/0010381 A1 | 1/2010 | Skelton et al. |
| 2010/0010383 A1 | 1/2010 | Skelton et al. |
| 2010/0010572 A1 | 1/2010 | Skelton et al. |
| 2010/0057154 A1 | 3/2010 | Dietrich et al. |
| 2010/0059722 A1 | 3/2010 | Copp-Howland et al. |
| 2010/0076533 A1 | 3/2010 | Dar et al. |
| 2010/0099963 A1 | 4/2010 | Kilger |
| 2010/0107657 A1 | 5/2010 | Vistakula |
| 2010/0125220 A1 | 5/2010 | Seong |
| 2010/0152817 A1 | 6/2010 | Gillbe |
| 2010/0168501 A1 | 7/2010 | Burnett et al. |
| 2010/0168604 A1 | 7/2010 | Echauz |
| 2010/0174342 A1 | 7/2010 | Boston et al. |
| 2010/0222630 A1 | 9/2010 | Mangrum et al. |
| 2010/0227330 A1 | 9/2010 | Fink et al. |
| 2010/0228180 A1 | 9/2010 | Jayes et al. |
| 2010/0249637 A1 | 9/2010 | Walter et al. |
| 2010/0292527 A1 | 11/2010 | Schneider et al. |
| 2010/0298905 A1 | 11/2010 | Simon |
| 2010/0324611 A1 | 12/2010 | Deming et al. |
| 2011/0004268 A1 | 1/2011 | Tcheng et al. |
| 2011/0009920 A1 | 1/2011 | Whitehurst et al. |
| 2011/0021899 A1 | 1/2011 | Arps et al. |
| 2011/0040204 A1 | 2/2011 | Ivorra et al. |
| 2011/0040288 A1 | 2/2011 | Eckstein et al. |
| 2011/0054358 A1 | 3/2011 | Kim et al. |
| 2011/0071590 A1 | 3/2011 | Mounaim et al. |
| 2011/0098780 A1 | 4/2011 | Graupe et al. |
| 2011/0112605 A1 | 5/2011 | Fahey |
| 2011/0118805 A1 | 5/2011 | Wei et al. |
| 2011/0125212 A1 | 5/2011 | Tyler |
| 2011/0137375 A1 | 6/2011 | McBride |
| 2011/0184489 A1 | 7/2011 | Nicolelis et al. |
| 2011/0196446 A1 | 8/2011 | Wu |
| 2011/0202107 A1 | 8/2011 | Sunagawa et al. |
| 2011/0208444 A1 | 8/2011 | Solinky |
| 2011/0213278 A1 | 9/2011 | Horak et al. |
| 2011/0224571 A1 | 9/2011 | Pascual-Leone et al. |
| 2011/0230701 A1 | 9/2011 | Simon et al. |
| 2011/0245734 A1 | 10/2011 | Wagner et al. |
| 2011/0250297 A1 | 10/2011 | Oronsky et al. |
| 2011/0282412 A1 | 11/2011 | Glukhovsky et al. |
| 2011/0288615 A1 | 11/2011 | Armstrong et al. |
| 2011/0301663 A1 | 12/2011 | Wang et al. |
| 2012/0010492 A1 | 1/2012 | Thramann et al. |
| 2012/0046535 A1 | 2/2012 | Lin et al. |
| 2012/0050298 A1 | 3/2012 | Hoffman |
| 2012/0053491 A1 | 3/2012 | Nathan et al. |
| 2012/0059298 A1 | 3/2012 | Hoffman et al. |
| 2012/0078319 A1 | 3/2012 | De Ridder |
| 2012/0088986 A1 | 4/2012 | David et al. |
| 2012/0092178 A1 | 4/2012 | Callsen et al. |
| 2012/0098493 A1 | 4/2012 | Budike |
| 2012/0101326 A1 | 4/2012 | Simon et al. |
| 2012/0109013 A1 | 5/2012 | Everett et al. |
| 2012/0136410 A1 | 5/2012 | Rezai et al. |
| 2012/0158094 A1 | 6/2012 | Kramer et al. |
| 2012/0184801 A1 | 7/2012 | Simon et al. |
| 2012/0185020 A1 | 7/2012 | Simon et al. |
| 2012/0211013 A1 | 8/2012 | Otis |
| 2012/0220812 A1 | 8/2012 | Mishelevich |
| 2012/0239112 A1 | 9/2012 | Muraoka |
| 2012/0245483 A1 | 9/2012 | Lundqvist |
| 2012/0259255 A1 | 10/2012 | Tomlinson et al. |
| 2012/0277621 A1 | 11/2012 | Gerber et al. |
| 2012/0289869 A1 | 11/2012 | Tyler |
| 2012/0290036 A1 | 11/2012 | Karamanoglu et al. |
| 2012/0302821 A1 | 11/2012 | Burnett |
| 2012/0310298 A1 | 12/2012 | Besio et al. |
| 2012/0310299 A1 | 12/2012 | Norbert et al. |
| 2012/0310303 A1 | 12/2012 | Popovic et al. |
| 2012/0330182 A1 | 12/2012 | Alberts et al. |
| 2013/0006322 A1 | 1/2013 | Tai |
| 2013/0035745 A1 | 2/2013 | Ahmed et al. |
| 2013/0053817 A1 | 2/2013 | Yun et al. |
| 2013/0060124 A1 | 3/2013 | Zietsma |
| 2013/0066388 A1 | 3/2013 | Bernhard et al. |
| 2013/0066395 A1 | 3/2013 | Simon et al. |
| 2013/0085317 A1 | 4/2013 | Feinstein |
| 2013/0090519 A1 | 4/2013 | Tass |
| 2013/0106684 A1 | 5/2013 | Weast et al. |
| 2013/0116606 A1 | 5/2013 | Cordo |
| 2013/0123568 A1 | 5/2013 | Hamilton et al. |
| 2013/0123666 A1 | 5/2013 | Giuffrida et al. |
| 2013/0131484 A1 | 5/2013 | Pernu |
| 2013/0131770 A1 | 5/2013 | Rezai |
| 2013/0158624 A1 | 6/2013 | Bain et al. |
| 2013/0158627 A1 | 6/2013 | Gozani et al. |
| 2013/0178765 A1 | 7/2013 | Mishelevich |
| 2013/0211471 A1 | 8/2013 | Libbus et al. |
| 2013/0231713 A1 | 9/2013 | De Ridder et al. |
| 2013/0236867 A1 | 9/2013 | Avni et al. |
| 2013/0238049 A1* | 9/2013 | Simon ............... A61N 1/36034 607/42 |
| 2013/0245486 A1 | 9/2013 | Simon et al. |
| 2013/0245713 A1 | 9/2013 | Tass |
| 2013/0253299 A1 | 9/2013 | Weber et al. |
| 2013/0267759 A1 | 10/2013 | Jin |
| 2013/0281890 A1 | 10/2013 | Mishelevich |
| 2013/0289647 A1 | 10/2013 | Bhadra et al. |
| 2013/0296967 A1 | 11/2013 | Skaribas et al. |
| 2013/0297022 A1 | 11/2013 | Pathak |
| 2013/0331907 A1 | 12/2013 | Sumners et al. |
| 2013/0333094 A1 | 12/2013 | Rogers et al. |
| 2013/0338726 A1 | 12/2013 | Machado |
| 2014/0025059 A1 | 1/2014 | Kerr |
| 2014/0031605 A1 | 1/2014 | Schneider |
| 2014/0039573 A1 | 2/2014 | Jindra |
| 2014/0039575 A1 | 2/2014 | Bradley |
| 2014/0046423 A1 | 2/2014 | Rajguru et al. |
| 2014/0058189 A1 | 2/2014 | Stubbeman |
| 2014/0067003 A1 | 3/2014 | Vase et al. |
| 2014/0078694 A1 | 3/2014 | Wissmar |
| 2014/0081345 A1 | 3/2014 | Hershey |
| 2014/0094675 A1 | 4/2014 | Luna et al. |
| 2014/0094873 A1 | 4/2014 | Emborg et al. |
| 2014/0128939 A1 | 5/2014 | Embrey et al. |
| 2014/0132410 A1 | 5/2014 | Chang |
| 2014/0142654 A1 | 5/2014 | Simon et al. |
| 2014/0148872 A1 | 5/2014 | Goldwasser et al. |
| 2014/0148873 A1 | 5/2014 | Kirn |
| 2014/0163444 A1 | 6/2014 | Ingvarsson |
| 2014/0171834 A1 | 6/2014 | DeGoede et al. |
| 2014/0200573 A1 | 7/2014 | Deem et al. |
| 2014/0214119 A1 | 7/2014 | Greiner et al. |
| 2014/0228927 A1 | 8/2014 | Ahmad et al. |
| 2014/0236258 A1 | 8/2014 | Carroll et al. |
| 2014/0246628 A1 | 9/2014 | Anhalt et al. |
| 2014/0249452 A1 | 9/2014 | Marsh et al. |
| 2014/0257047 A1 | 9/2014 | Sillay et al. |
| 2014/0257129 A1 | 9/2014 | Choi et al. |
| 2014/0276194 A1 | 9/2014 | Osorio |
| 2014/0277220 A1 | 9/2014 | Brennan et al. |
| 2014/0296752 A1 | 10/2014 | Edgerton et al. |
| 2014/0296934 A1 | 10/2014 | Gozani et al. |
| 2014/0296935 A1 | 10/2014 | Ferree et al. |
| 2014/0300490 A1 | 10/2014 | Kotz et al. |
| 2014/0309709 A1 | 10/2014 | Gozanl et al. |
| 2014/0316484 A1 | 10/2014 | Edgerton et al. |
| 2014/0324118 A1 | 10/2014 | Simon et al. |
| 2014/0330068 A1 | 11/2014 | Partsch et al. |

(56) References Cited

U.S. PATENT DOCUMENTS

| | | |
|---|---|---|
| 2014/0330335 A1 | 11/2014 | Errico et al. |
| 2014/0336003 A1 | 11/2014 | Franz et al. |
| 2014/0336722 A1 | 11/2014 | Rocon De Lima et al. |
| 2014/0343462 A1 | 11/2014 | Burnet |
| 2014/0350436 A1 | 11/2014 | Nathan et al. |
| 2014/0358040 A1 | 12/2014 | Kim et al. |
| 2014/0364678 A1 | 12/2014 | Harry et al. |
| 2015/0004656 A1 | 1/2015 | Tang et al. |
| 2015/0005852 A1 | 1/2015 | Hershey et al. |
| 2015/0012067 A1* | 1/2015 | Bradley ............ A61N 1/36017 607/60 |
| 2015/0038886 A1 | 2/2015 | Snow |
| 2015/0042315 A1 | 2/2015 | Cen et al. |
| 2015/0044656 A1 | 2/2015 | Eichhorn et al. |
| 2015/0057506 A1 | 2/2015 | Luna et al. |
| 2015/0073310 A1 | 3/2015 | Pracar et al. |
| 2015/0080979 A1 | 3/2015 | Lasko et al. |
| 2015/0100004 A1 | 4/2015 | Goldman et al. |
| 2015/0100104 A1 | 4/2015 | Kiani et al. |
| 2015/0100105 A1 | 4/2015 | Kiani et al. |
| 2015/0148866 A1 | 5/2015 | Bulsen et al. |
| 2015/0148878 A1* | 5/2015 | Yoo ..................... A61N 1/0556 607/148 |
| 2015/0157274 A1 | 6/2015 | Ghassemzadeh et al. |
| 2015/0164377 A1 | 6/2015 | Nathan et al. |
| 2015/0164401 A1 | 6/2015 | Toth et al. |
| 2015/0190085 A1 | 7/2015 | Nathan et al. |
| 2015/0190634 A1 | 7/2015 | Rezai et al. |
| 2015/0196767 A1 | 7/2015 | Zaghloul |
| 2015/0202444 A1 | 7/2015 | Franke et al. |
| 2015/0208955 A1 | 7/2015 | Smith |
| 2015/0216475 A1 | 8/2015 | Luna et al. |
| 2015/0230733 A1 | 8/2015 | Heo et al. |
| 2015/0230756 A1 | 8/2015 | Luna et al. |
| 2015/0277559 A1 | 10/2015 | Vescovi et al. |
| 2015/0297901 A1 | 10/2015 | Kockx |
| 2015/0321000 A1 | 11/2015 | Rosenbluth et al. |
| 2015/0335882 A1 | 11/2015 | Gross et al. |
| 2016/0001096 A1 | 1/2016 | Mishelevich |
| 2016/0008620 A1 | 1/2016 | Stubbeman |
| 2016/0016014 A1 | 1/2016 | Wagner et al. |
| 2016/0022987 A1 | 1/2016 | Zschaeck et al. |
| 2016/0022989 A1 | 1/2016 | Pfeifer |
| 2016/0038059 A1 | 2/2016 | Asada et al. |
| 2016/0045140 A1 | 2/2016 | Kitamura et al. |
| 2016/0089045 A1 | 3/2016 | Sadeghian-Motahar et al. |
| 2016/0106344 A1 | 4/2016 | Nazari |
| 2016/0121110 A1 | 5/2016 | Kent et al. |
| 2016/0128621 A1 | 5/2016 | Machado et al. |
| 2016/0129248 A1 | 5/2016 | Creasey et al. |
| 2016/0158542 A1 | 6/2016 | Ahmed |
| 2016/0158565 A1 | 6/2016 | Lee |
| 2016/0198998 A1 | 7/2016 | Rahimi et al. |
| 2016/0213924 A1 | 7/2016 | Coleman et al. |
| 2016/0220836 A1 | 8/2016 | Parks |
| 2016/0262685 A1 | 9/2016 | Wagner et al. |
| 2016/0263376 A1 | 9/2016 | Yoo et al. |
| 2016/0287879 A1 | 10/2016 | Denison et al. |
| 2016/0039239 A1 | 11/2016 | Yoo et al. |
| 2016/0336722 A1 | 11/2016 | Taxter |
| 2016/0339239 A1 | 11/2016 | Yoo et al. |
| 2016/0361540 A9 | 12/2016 | Simon et al. |
| 2016/0375249 A1 | 12/2016 | Bonnet et al. |
| 2017/0014625 A1 | 1/2017 | Rosenbluth et al. |
| 2017/0027812 A1 | 2/2017 | Hyde et al. |
| 2017/0042467 A1 | 2/2017 | Herr et al. |
| 2017/0056238 A1 | 3/2017 | Yi et al. |
| 2017/0056643 A1 | 3/2017 | Herb et al. |
| 2017/0079597 A1 | 3/2017 | Horne |
| 2017/0080207 A1 | 3/2017 | Perez et al. |
| 2017/0095667 A1 | 4/2017 | Yakovlev et al. |
| 2017/0113045 A1 | 4/2017 | Baldassano et al. |
| 2017/0157398 A1 | 6/2017 | Wong et al. |
| 2017/0165485 A1 | 6/2017 | Sullivan et al. |
| 2017/0132067 A1 | 8/2017 | Wong et al. |
| 2017/0224991 A1 | 8/2017 | Wingeier et al. |
| 2017/0239415 A1 | 8/2017 | Hwang et al. |
| 2017/0246481 A1 | 8/2017 | Mishelevich |
| 2017/0266443 A1 | 9/2017 | Rajguru et al. |
| 2017/0274208 A1 | 9/2017 | Nagel et al. |
| 2017/0287146 A1 | 10/2017 | Pathak et al. |
| 2017/0312505 A1 | 11/2017 | Ahmed |
| 2017/0312512 A1 | 11/2017 | Creasey et al. |
| 2017/0312513 A1 | 11/2017 | Hershey et al. |
| 2017/0361093 A1 | 12/2017 | Yoo et al. |
| 2017/0368329 A1 | 12/2017 | Tyler et al. |
| 2018/0001086 A1 | 1/2018 | Bartholomew et al. |
| 2018/0001088 A1 | 1/2018 | Tass |
| 2018/0021576 A1 | 1/2018 | Wong et al. |
| 2018/0028841 A1 | 2/2018 | Konofagou et al. |
| 2018/0036535 A1 | 2/2018 | Wong et al. |
| 2018/0042654 A1 | 2/2018 | Ingvarsson et al. |
| 2018/0049676 A1 | 2/2018 | Griffiths et al. |
| 2018/0064344 A1 | 3/2018 | Nguyen |
| 2018/0064362 A1 | 3/2018 | Hennings et al. |
| 2018/0064944 A1 | 3/2018 | Grill et al. |
| 2018/0116546 A1 | 5/2018 | Pastoor et al. |
| 2018/0132757 A1 | 5/2018 | Kong et al. |
| 2018/0140842 A1 | 5/2018 | Olaighin et al. |
| 2018/0168905 A1 | 6/2018 | Goodall et al. |
| 2018/0169400 A1 | 6/2018 | Wong et al. |
| 2018/0214694 A1 | 8/2018 | Parramon |
| 2018/0221620 A1 | 8/2018 | Metzger |
| 2018/0235500 A1 | 8/2018 | Lee et al. |
| 2018/0236217 A1 | 8/2018 | Hamner et al. |
| 2018/0264263 A1 | 9/2018 | Rosenbluth et al. |
| 2018/0345020 A1 | 12/2018 | Ironi et al. |
| 2019/0001117 A1 | 1/2019 | Ben-David et al. |
| 2019/0001129 A1 | 1/2019 | Rosenbluth et al. |
| 2019/0001139 A1 | 1/2019 | Mishra et al. |
| 2019/0126047 A1 | 5/2019 | Kassiri Bidhendi et al. |
| 2019/0134393 A1 | 5/2019 | Wong et al. |
| 2019/0143098 A1 | 5/2019 | Kaplan et al. |
| 2019/0143111 A1 | 5/2019 | Hamner et al. |
| 2019/0143113 A1 | 5/2019 | Wong et al. |
| 2019/0167976 A1 | 6/2019 | Byers et al. |
| 2019/0269914 A1 | 9/2019 | Moaddeb et al. |
| 2019/0298998 A1 | 10/2019 | Coleman et al. |
| 2019/0321636 A1 | 10/2019 | Law |
| 2019/0343462 A1 | 11/2019 | Grant et al. |
| 2019/0374771 A1 | 12/2019 | Simon et al. |
| 2020/0023183 A1 | 1/2020 | Ollerenshaw et al. |
| 2020/0038654 A1 | 2/2020 | Doskocil et al. |
| 2020/0046968 A1 | 2/2020 | Herr et al. |
| 2020/0061378 A1 | 2/2020 | Ganguly et al. |
| 2020/0093400 A1 | 3/2020 | Hamner et al. |
| 2020/0139118 A1 | 5/2020 | John et al. |
| 2020/0147373 A1 | 5/2020 | Tamaki et al. |
| 2020/0155847 A1 | 5/2020 | Perez |
| 2020/0171269 A1 | 6/2020 | Hooper et al. |
| 2020/0171304 A1 | 6/2020 | Simon et al. |
| 2020/0179687 A1 | 6/2020 | Wong et al. |
| 2020/0197707 A1 | 6/2020 | Covalin |
| 2020/0215324 A1 | 7/2020 | Mantovani et al. |
| 2020/0221975 A1 | 7/2020 | Basta et al. |
| 2020/0254247 A1 | 8/2020 | Brezel et al. |
| 2020/0254251 A1 | 8/2020 | Wong et al. |
| 2020/0269046 A1 | 8/2020 | Page et al. |
| 2020/0276442 A1 | 9/2020 | Owen |
| 2020/0282201 A1 | 9/2020 | Doskocil |
| 2020/0289813 A1 | 9/2020 | Ito et al. |
| 2020/0289814 A1 | 9/2020 | Hamner et al. |
| 2020/0297999 A1 | 9/2020 | Pal |
| 2020/0316379 A1 | 10/2020 | Yoo et al. |
| 2020/0324104 A1 | 10/2020 | Labuschagne et al. |
| 2020/0338348 A1 | 10/2020 | Honeycutt et al. |
| 2020/0367775 A1 | 11/2020 | Buckley et al. |
| 2020/0405188 A1 | 12/2020 | Sharma et al. |
| 2020/0406022 A1 | 12/2020 | Sharma et al. |
| 2021/0016079 A1 | 1/2021 | Ekelem et al. |
| 2021/0031026 A1 | 2/2021 | Simon et al. |
| 2021/0031036 A1 | 2/2021 | Sharma et al. |
| 2021/0052897 A1 | 2/2021 | Bhadra et al. |
| 2021/0052900 A1 | 2/2021 | Pepin et al. |

(56) References Cited

U.S. PATENT DOCUMENTS

| | | |
|---|---|---|
| 2021/0060337 A1 | 3/2021 | Wybo et al. |
| 2021/0069507 A1 | 3/2021 | Gozani et al. |
| 2021/0101007 A1 | 4/2021 | Hamner et al. |
| 2021/0162212 A1 | 6/2021 | Kern et al. |
| 2021/0169684 A1 | 6/2021 | Black et al. |
| 2021/0187279 A1 | 6/2021 | Bouton et al. |
| 2021/0205619 A1 | 7/2021 | Wong et al. |
| 2021/0213283 A1 | 7/2021 | Yoo et al. |
| 2021/0220650 A1 | 7/2021 | Kassiri Bidhendi et al. |
| 2021/0244940 A1 | 8/2021 | Liberatore et al. |
| 2021/0244950 A1 | 8/2021 | Ironi et al. |
| 2021/0252278 A1 | 8/2021 | Hamner et al. |
| 2021/0260379 A1 | 8/2021 | Charlesworth et al. |
| 2021/0266011 A1 | 8/2021 | Chen et al. |
| 2021/0283400 A1 | 9/2021 | Hamner et al. |
| 2021/0289814 A1 | 9/2021 | Hamner et al. |
| 2021/0299445 A1 | 9/2021 | Rajguru et al. |
| 2021/0330547 A1 | 10/2021 | Moaddeb et al. |
| 2021/0353181 A1 | 11/2021 | Roh |
| 2021/0379374 A1 | 12/2021 | Hamner et al. |
| 2021/0379379 A1 | 12/2021 | Campean et al. |
| 2021/0402172 A1 | 12/2021 | Ross et al. |
| 2022/0001164 A1 | 1/2022 | Sharma et al. |
| 2022/0016413 A1 | 1/2022 | John et al. |
| 2022/0031245 A1 | 2/2022 | Bresler |
| 2022/0054820 A1 | 2/2022 | Turner |
| 2022/0054831 A1 | 2/2022 | McBride |
| 2022/0088373 A1 | 3/2022 | Burnett |
| 2022/0126095 A1 | 4/2022 | Rajguru et al. |
| 2022/0143402 A1 | 5/2022 | Oppenheim et al. |
| 2022/0212007 A1 | 7/2022 | Rajguru et al. |
| 2022/0218991 A1 | 7/2022 | Moaddeb et al. |
| 2022/0220276 A1 | 7/2022 | Ziebell et al. |
| 2022/0233860 A1 | 7/2022 | Hamner et al. |
| 2022/0266011 A1 | 8/2022 | Hamner et al. |
| 2022/0266012 A1 | 8/2022 | Hamner et al. |
| 2023/0009158 A1 | 1/2023 | Liberatore |
| 2023/0191126 A1 | 6/2023 | Kent et al. |
| 2023/0201584 A1 | 6/2023 | Rajguru et al. |
| 2024/0189594 A1 | 6/2024 | Hamner et al. |

FOREIGN PATENT DOCUMENTS

| | | |
|---|---|---|
| CN | 1135722 | 11/1996 |
| CN | 1547483 | 11/2004 |
| CN | 1826154 | 8/2006 |
| CN | 101022849 | 8/2007 |
| CN | 101115524 | 1/2008 |
| CN | 101365373 | 2/2009 |
| CN | 101687093 | 3/2010 |
| CN | 101801453 | 8/2010 |
| CN | 102089031 | 6/2011 |
| CN | 102481394 | 5/2012 |
| CN | 202724457 | 2/2013 |
| CN | 103517732 | 1/2014 |
| CN | 103889503 | 6/2014 |
| CN | 104144729 | 11/2014 |
| CN | 104168951 | 11/2014 |
| CN | 104519960 | 4/2015 |
| CN | 105142714 A | 12/2015 |
| CN | 105457158 | 4/2016 |
| CN | 105848710 | 8/2016 |
| CN | 106413805 | 2/2017 |
| CN | 106687161 | 5/2017 |
| CN | 106794347 | 5/2017 |
| CN | 107949421 | 4/2018 |
| CN | 108697890 | 10/2018 |
| CN | 108348746 | 10/2021 |
| CN | 108778411 | 6/2022 |
| DE | 102008042373 | 4/2010 |
| DE | 102009004011 | 7/2010 |
| EP | 0 000 759 | 2/1979 |
| EP | 0 725 665 | 1/1998 |
| EP | 1 062 988 | 12/2000 |
| EP | 1 558 333 | 5/2007 |
| EP | 1727591 | 4/2009 |
| EP | 2 383 014 | 11/2011 |
| EP | 2291115 | 9/2013 |
| EP | 2 801 389 | 11/2014 |
| EP | 3 020 448 | 5/2016 |
| EP | 2029222 | 3/2017 |
| EP | 2780073 | 9/2017 |
| EP | 1951365 | 10/2017 |
| EP | 3154627 | 4/2018 |
| EP | 2827771 | 5/2018 |
| EP | 3184143 | 7/2018 |
| EP | 3075412 | 12/2018 |
| EP | 3349712 | 7/2019 |
| EP | 3503960 | 3/2020 |
| EP | 3352846 | 7/2020 |
| EP | 3493874 | 8/2020 |
| EP | 3409200 | 9/2020 |
| EP | 3427793 | 11/2020 |
| EP | 3641876 | 4/2021 |
| EP | 3352843 | 6/2021 |
| EP | 3679979 | 6/2021 |
| EP | 3402404 | 7/2021 |
| EP | 3562541 | 7/2021 |
| EP | 3675795 | 8/2021 |
| EP | 3100765 | 1/2022 |
| EP | 4108292 | 12/2022 |
| ES | 2222819 | 3/2006 |
| ES | 2272137 | 6/2008 |
| GB | 2496449 | 5/2013 |
| JP | 2010-527256 | 1/1900 |
| JP | 63-500644 | 3/1988 |
| JP | 2002-200178 | 7/2002 |
| JP | 2003-501207 | 1/2003 |
| JP | 2003-533299 | 11/2003 |
| JP | 2004-512104 | 4/2004 |
| JP | 2006-503658 | 2/2006 |
| JP | 2008-018235 | 1/2008 |
| JP | 2009-034328 | 2/2009 |
| JP | 2009-512516 | 3/2009 |
| JP | 2009-529352 | 8/2009 |
| JP | 2010-506618 | 3/2010 |
| JP | 2010-512926 | 4/2010 |
| JP | 2010-246745 | 11/2010 |
| JP | 2012-005596 | 1/2012 |
| JP | 2012-055650 | 3/2012 |
| JP | 2012-217565 | 11/2012 |
| JP | 2013-017609 | 1/2013 |
| JP | 2013-094305 | 5/2013 |
| JP | 5439921 B2 | 3/2014 |
| JP | 2015-514460 | 5/2015 |
| JP | 2016-511651 | 4/2016 |
| JP | 2018-038597 | 3/2018 |
| KR | 20130104446 | 9/2013 |
| WO | WO 1987/01024 | 2/1987 |
| WO | WO 94/000187 | 1/1994 |
| WO | WO 94/017855 | 8/1994 |
| WO | WO 96/032909 | 10/1996 |
| WO | WO 98/043700 | 10/1998 |
| WO | WO 99/019019 | 4/1999 |
| WO | WO 00/015293 | 3/2000 |
| WO | WO 2000/076436 | 12/2000 |
| WO | WO 2001/087411 | 11/2001 |
| WO | WO 02/017987 | 3/2002 |
| WO | WO 02/34327 | 5/2002 |
| WO | WO 2004/037344 | 5/2004 |
| WO | WO 2004/108209 | 12/2004 |
| WO | WO 2005/007029 | 5/2005 |
| WO | WO 05/122894 | 12/2005 |
| WO | WO 2006/021820 | 3/2006 |
| WO | WO 2006/092007 | 9/2006 |
| WO | WO 2006/102724 | 10/2006 |
| WO | WO 2007/092290 | 8/2007 |
| WO | WO 07/112092 | 10/2007 |
| WO | WO 2008/045598 | 4/2008 |
| WO | WO 2008/062395 | 5/2008 |
| WO | WO 2008/106174 | 9/2008 |
| WO | WO 09/153730 | 12/2009 |
| WO | WO 2010/014260 | 2/2010 |
| WO | WO 10/111321 | 9/2010 |

(56) References Cited

FOREIGN PATENT DOCUMENTS

| | | |
|---|---|---|
| WO | WO 10/141155 | 12/2010 |
| WO | WO 11/119224 | 9/2011 |
| WO | WO 11/144883 | 11/2011 |
| WO | WO 2011/149656 | 12/2011 |
| WO | WO 12/040243 | 3/2012 |
| WO | WO 13/071307 | 5/2013 |
| WO | WO 13/074809 | 5/2013 |
| WO | WO 2013/173727 | 11/2013 |
| WO | WO 14/043757 | 3/2014 |
| WO | WO 14/053041 | 4/2014 |
| WO | WO 2014/070999 | 5/2014 |
| WO | WO 2014/089549 | 6/2014 |
| WO | WO-2014093964 A1 * | 6/2014 ........... A61N 1/0551 |
| WO | WO 2014/113813 | 7/2014 |
| WO | WO 14/146082 | 9/2014 |
| WO | WO 14/151431 | 9/2014 |
| WO | WO 14/153201 | 9/2014 |
| WO | WO 14/207512 | 12/2014 |
| WO | WO 15/033152 | 3/2015 |
| WO | WO 15/039206 | 3/2015 |
| WO | WO 15/039244 | 3/2015 |
| WO | WO 15/042365 | 3/2015 |
| WO | WO 15/079319 | 6/2015 |
| WO | WO 15/095880 | 6/2015 |
| WO | WO 2015/085880 | 6/2015 |
| WO | WO 15/128090 | 9/2015 |
| WO | WO 2015/138981 | 9/2015 |
| WO | WO 15/164706 | 10/2015 |
| WO | WO 2015/187712 | 12/2015 |
| WO | WO 16/007093 | 1/2016 |
| WO | WO 16/019250 | 2/2016 |
| WO | WO 16/094728 | 6/2016 |
| WO | WO 16/102958 | 6/2016 |
| WO | WO 16/110804 | 7/2016 |
| WO | WO 16/128985 | 8/2016 |
| WO | WO 16/149751 | 9/2016 |
| WO | WO 16/166281 | 10/2016 |
| WO | WO 16/179407 | 11/2016 |
| WO | WO 2016/176668 | 11/2016 |
| WO | WO 16/189422 | 12/2016 |
| WO | WO 16/195587 | 12/2016 |
| WO | WO 2016/201366 | 12/2016 |
| WO | WO 17/004021 | 1/2017 |
| WO | WO 17/010930 | 1/2017 |
| WO | WO 2017/023864 | 2/2017 |
| WO | WO 2017/044904 | 3/2017 |
| WO | WO 2017/053847 | 3/2017 |
| WO | WO 17/062994 | 4/2017 |
| WO | WO 17/086798 | 5/2017 |
| WO | WO 17/088573 | 6/2017 |
| WO | WO 17/199026 | 11/2017 |
| WO | WO 2017/199026 | 11/2017 |
| WO | WO 17/208167 | 12/2017 |
| WO | WO 17/209673 | 12/2017 |
| WO | WO 17/210729 | 12/2017 |
| WO | WO 17/221037 | 12/2017 |
| WO | WO 2018/009680 | 1/2018 |
| WO | WO 18/028170 | 2/2018 |
| WO | WO 18/028220 | 2/2018 |
| WO | WO 18/028221 | 2/2018 |
| WO | WO 2018/039458 | 3/2018 |
| WO | WO 18/093765 | 5/2018 |
| WO | WO 18/112164 | 6/2018 |
| WO | WO 2018/106839 | 6/2018 |
| WO | WO 2018119220 | 6/2018 |
| WO | WO 2018/187241 | 10/2018 |
| WO | WO 19/005774 | 1/2019 |
| WO | WO 19/014250 | 1/2019 |
| WO | WO 19/028000 | 2/2019 |
| WO | WO 2019/046180 | 3/2019 |
| WO | WO 2019/082180 | 6/2019 |
| WO | WO 2019/143790 | 7/2019 |
| WO | WO 2019/169240 | 9/2019 |
| WO | WO 2019/202489 | 10/2019 |
| WO | WO 2019/213433 | 11/2019 |
| WO | WO 2020/006048 | 1/2020 |
| WO | WO 2020/068830 | 4/2020 |
| WO | WO 2020/069219 | 4/2020 |
| WO | WO 2020/086726 | 4/2020 |
| WO | WO 2020/131857 | 6/2020 |
| WO | WO 2020/185601 | 9/2020 |
| WO | WO 2021/005584 | 1/2021 |
| WO | WO 2021/055716 | 3/2021 |
| WO | WO 2021/062345 | 4/2021 |
| WO | WO 2021/127422 | 6/2021 |
| WO | WO 2021/228128 | 11/2021 |
| WO | WO 2021/236815 | 11/2021 |
| WO | WO 2021/252292 | 12/2021 |
| WO | WO 2022/221858 | 10/2022 |
| WO | WO 2023/283568 | 1/2023 |
| WO | WO 2023/014499 | 2/2023 |
| WO | WO 2023/015158 | 2/2023 |
| WO | WO 2023/015159 | 3/2023 |

OTHER PUBLICATIONS

Barbaud et al.; Improvement in essential tremor after pure sensory stroke due to thalamic infarction; European neurology; 46; pp. 57-59; Jul. 2001.

Barrios et al.: BCI algorithms for tremor identification, characterization and tracking; Seventh Framework Programme, EU; Contract No. FP7-ICT-2007-224051 (v3.0); 57 pgs.; Jul. 10, 2011.

Bartley et al.; Neuromodulation for overactive bladder; Nature Reviews Urology; 10; pp. 513-521; Sep. 2013.

Benabid et al.; A putative generalized model of the effects and mechanism of action of high frequency electrical stimulation of the central nervous system; Acta Neural Belg; 105(3); pp. 149-157; Sep. 2005.

Bergquist et al.: Motor unit recruitment when neuromuscular electrical stimulation is applied over a nerve trunk compared with a muscle belly: quadriceps femoris, Journal of Applied Physiology; vol. 113, No. 1, pp. 78-89; Jul. 2012.

Bergquist et al.; Motor unit recruitment when neuromuscular electrical stimulation is applied over a nerve trunk compared with a muscle belly: triceps surae, Journal of Applied Physiology; vol. 110, No. 3, pp. 627-637; Mar. 2011.

Bijelic et al.: E Actitrode®: The New Selective Stimulation Interface for Functional Movements in Hemiplegic Patients; Serbian Journal of Electrical Engineering; 1(3); pp. 21-28; Nov. 2004.

Birdno et al.; Pulse-to-pulse changes in the frequency of deep brain stimulation affect tremor and modeled neuronal activity.; Journal of Neurophysiology; 98; pp. 1675-1684; Jul. 2007.

Birdno et al.; Response of human thalamic neurons to high-frequency stimulation.; PloS One; 9(5); 10 pgs.; May 2014.

Birgersson et al.; Non-invasive bioimpedance of intact skin: mathematical modeling and experiments; Physiological Measurement; 32(1); pp. 1-18; Jan. 2011.

Bohling et al.; Comparison of the stratum corneum thickness measured in vivo with confocal Raman spectroscopy and confocal reflectance microscopy; Skin research and Technology; 20(1); pp. 50-47; Feb. 2014.

Bonaz, B., V. Sinniger, and S. Pellissier. "Vagus nerve stimulation: a new promising therapeutic tool in inflammatory bowel disease." Journal of internal medicine 282.1 (2017): 46-63.

Bowman et al.; Effects of waveform parameters on comfort during transcutaneous neuromuscular electrical stimulation; Annals of Biomedical Engineering; 13(1); pp. 59-74; Jan. 1985.

Bratton et al.; Neural regulation of inflammation: no neural connection from the vagus to splenic sympathetic neurons; Exp Physiol 97.11 (2012); pp. 1180-1185.

Brittain et al.; Tremor suppression by rhythmic transcranial current stimulation; Current Biology; 23; pp. 436-440; Mar. 2013.

Britton et al.; Modulation of postural tremors at the wrist by supramaximal electrical median nerve shocks in ET, PD, and normal subjects mimicking tremor; J Neurology, Neurosurgery, and Psychiatry; 56(10); pp. 1085-1089; Oct. 1993.

Buschbacher et al.; Manual of nerve conduction series; 2nd edition; Demos Medical Publishing, LLC; 2006.

(56) References Cited

OTHER PUBLICATIONS

Cagnan et al.; Phase dependent modulation of tremor amplitude in essential tremor through thalamic stimulation; Brain; 136(10); pp. 3062-3075; Oct. 2013.
Campero et al.; Peripheral projections of sensory fasicles in the human superificial radial nerve; Brain; 128(Pt 4); pp. 892-895; Apr. 2005.
Chen et al.; A web-based system for home monitoring of patients with Parkinson's disease using wearable sensors; IEEE Trans on Bio-Medical Engineering; 58(3); pp. 831-836; Mar. 2011.
Choi, Jong Bo, et al. "Analysis of heart rate variability in female patients with overactive bladder." Urology 65.6 (2005): 1109-1112.
Clair et al.; Postactivation depression and recovery of reflex transmission during repetitive electrical stimulation of the human tibial nerve, Journal of Neurophysiology; vol. 106, No. 1; pp. 184-192; Jul. 2011.
Clar et al.; Skin impedance and moisturization; J. Soc. Cosmet. Chem.; 26; pp. 337-353; 1975; presented at IFSCC Vilith Int'l Congresson Cosmetics Quality and Safety in London on Aug. 26-30, 1974.
Constandinou et al.; A Partial-Current-Steering Biphasic Stimulation Driver for Vestibular Prostheses; IEEE Trans on Biomedical Circuits and Systems; 2(2); pp. 106-113; Jun. 2008.
Daneault et al.; Using a smart phone as a standalone platform for detection and monitoring of pathological tremors; Frontiers in Human Neuroscience; vol. 6, article 357; 12 pgs.; Jan. 2012.
Deuschl et at; Consensus statement of the Movement Disorder Society on Tremor. Ad Hoc Scientific Committee., Movement Disorders, vol. 13 Suppl 3, pp. 2-23; (year of pub. sufficiently earlier than effective US filing date and any foreign priority date) 1998.
Di Giovangiulio et al.; The Neuromodulation of the intestinal immune system and its relevance in inflammatory bowel disease; Fronteir's in Immunology; vol. 6; Article 590; Nov. 2015.
Dideriksen et al.; EMG-based characterization of pathological tremor using the iterated Hilbert transform; IEEE transactions on Biomedical Engineering; 58(10); pp. 2911-2921; Oct. 2011.
Dosen et al.: Tremor suppression using electromyography and surface sensory electrical stimulation; Converging Clinical and Engineering Research on Neurorehabilitation; vol. 1 (Siosystems & Biorobotics Series); pp. 539-543; Feb. 2013.
Doucet et al.; Neuromuscular electrical stimulation for skeletal muscle function; The Yale Journal of Biology and Medicine; 85(2); pp. 201-215; Jun. 2012.
Fuentes et al.; Restoration of locomotive function in Parkinson's disease by spinal cord stimulation: mechanistic approach, Eur J Neurosci, vol. 32, pp. 1100-1108; Oct. 2010 (author manuscript; 19 pgs.).
Fuentes et al.; Spinal cord stimulation restores locomotion in animal models of Parkinson's disease; Science; 323; pp. 1578-1582; Mar. 2009.
Gallego et al.; A neuroprosthesis for tremor management through the control of muscle co-contraction; Journal of Neuroengineering and Rehabilitation; vol. 10; 36; (13 pgs); Apr. 2013.
Gallego et al; A soft wearable robot for tremor assessment and suppression; 2011 IEEE International Conference on Robotics and Automation; Shanghai International Conference Center; pp. 2249-2254; May 9-13, 2011.
Gallego et al.; Real-time estimation of pathological tremor parameters from gyroscope data.; Sensors; 10(3); pp. 2129-2149; Mar. 2010.
Gao; Analysis of amplitude and frequency variations of essential and Parkinsonian tremors; Medical & Biological Engineering & Computing; 42(3); pp. 345-349; May 2004.
Garcia et al.; Modulation of brainstem activity and connectivity by respiratory-gated auricular vagal afferent nerve stimulation in migraine patients; PAIN; International Association for the Study of Pain; 2017.
Garcia-Rill, E., et al. "Arousal, motor control, and Parkinson's disease." Translational neuroscience 6.1 pp. 198-207 (2015).
Giuffrida et al.; Clinically deployable Kinesia technology for automated tremor assessment.; Movement Disorders; 24(5); pp. 723-730; Apr. 2009.
Gracanin et al.; Optimal stimulus parameters for minimum pain in the chronic stimulatin of innervated muscle; Archives of Physical Medicine and Rehabilitation; 56(6); pp. 243-249; Jun. 1975.
Haeri et al.; Modeling the Parkinson's tremor and its treatments; Journal of Theorectical Biology; 236(3); pp. 311-322; Oct. 2005.
Halon En et al.; Contribution of cutaneous and muscle afferent fibres to cortical SEPs following median and radial nerve stimulation in man; Electroenceph. Clin. Neurophysiol.; 71(5); pp. 331-335; Sep.-Oct. 1988.
Hao et al.; Effects of electrical stimulation of cutaneous afferents on corticospinal transmission of tremor signals in patients with Parkinson's disease; 6th International Conference on Neural Engineering; San Diego, CA; pp. 355-358; Nov. 2013.
Hauptmann et al.; External trial deep brain stimulation device for the application of desynchronizing stimulation techniques; Journal of Neural Engineering; 6; 12 pgs.; Oct. 2009.
Heller et al.; Automated setup of functional electrical stimulation for drop foot using a novel 64 channel prototype stimulator and electrode array: Results from a gait-lab based study; Medical Engineering & Physic; 35(1); pp. 74-81; Jan. 2013.
Henry Dreyfuss Associates; The Measure of Man and Woman: Human Factors in Design (Revised Edition); John Wiley & Sons, New York; pp. 10-11 and 22-25; Dec. 2001.
Hernan, Miguel, et al. "Alcohol Consumption and the Incidence of Parkinson's Disease." May 15, 2003. Annals of Neurology. vol. 54. pp. 170-175.
Hua et al.; Posture-related oscillations in human cerebellar thalamus in essential tremor are enabled by voluntary motor circuits; J Neurophysiol; 93(1); pp. 117-127; Jan. 2005.
Huang, et al.; Theta burst stimulation report of the human motor cortex; Neuron, vol. 45, 201-206, Jan. 20, 2005.
Hubeaux, Katelyne, et al. "Autonomic nervous system activity during bladder filling assessed by heart rate variability analysis in women with idiopathic overactive bladder syndrome or stress urinary incontinence." The Journal of urology 178.6 (2007): 2483-2487.
Hubeaux, Katelyne, et al. "Evidence for autonomic nervous system dysfunction in females with idiopathic overactive bladder syndrome." Neurourology and urodynamics 30.8 (2011): 1467-1472.
Inoue, Masahiro, Katsuaki Suganuma, and Hiroshi Ishiguro. "Stretchable human interface using a conductive silicone elastomer containing silver fillers." Consumer Electronics, 2009. ISCE'09. IEEE 13th International Symposium on. IEEE, 2009.
Jacks et al.; Instability in human forearm movements studied with feed-back-controlled electrical stimulation of muscles; Journal of Physiology; 402; pp. 443-461; Aug. 1988.
Jobges et al.; Vibratory proprioceptive stimulation affects Parkinsonian tremor; Parkinsonism & Related Disorders; 8(3); pp. 171-176; Jan. 2002.
Joundi et al.; Rapid tremor frequency assessment with the iPhone accelerometer.; Parkinsonism & Related Disorders; 17(4); pp. 288-290; May 2011.
Kim et al.: Adaptive control of movement for neuromuscular stimulation-assisted therapy in a rodent model; IEEE Trans on Biomedical Engineering,, 56(2); pp. 452-461; Feb. 2009.
Krauss et al.; Chronic spinal cord stimulation in medically intractable orthostatic tremor; J Neurol Neurosurg Psychiatry; 77(9); pp. 1013-1016; Sep. 2006.
Kuhn et al.; Array electrode design for transcutaneous electrical stimulation a simulation study; Medical Engineering & Physics; 31 (8); pp. 945-951; Oct. 2009.
Kuhn et al.; The Influence of Electrode Size on Selectivity and Comfort in Transcutaneous Electrical Stimulation of the Forearm; Neural Systems and Rehabilitation Engineering, IEEE Transactions on; 18(3); pp. 255-262; Jun. 2010.
Kunz, Patrik, et al. "5 KHz transcranial alternating current stimulation: lack of cortical excitability changes when grouped in a theta burst pattern." Frontiers in Human Neuroscience 10 (2016): 683.

(56) References Cited

OTHER PUBLICATIONS

Lagerquist et al.: Influence of stimulus pulse width on M-waves, H-reflexes, and torque during tetanic low-intensity neuromuscular stimulation, Muscle & Nerve, 42(6), pp. 886-893; Dec. 2010.
Laroy et al.; The sensory innervation pattern of the fingers; J. Neurol.; 245 (5); pp. 294-298; May 1998.
Lee et al.; Resetting of tremor by mechanical perturbations: A comparison of essential tremor and parkinsonian tremor; Annals of Nuerology: 10(6); pp. 523-531; Dec. 1981.
Legon et al.; Pulsed ultrasound differentially stimulates somatosensory circuits in humans as indicated by EEG and fMRI; PloS One; 7(12); e51177; 14 pgs.; Dec. 2012.
Liao et al. "A noninvasive evaluation of autonomic nervous system dysfunction in women with an overactive bladder." International Journal of Gynecology & Obstetrics 110.1 (2010): 12-17.
Lourenco et al.; Effects produced in human arm and forearm motoneurones after electrical stimulation of ulnar and median nerves at wrist level; Experimental Brain Research; 178(2); pp. 267-284; Apr. 2007.
Malek et al.; The utility of electromyography and mechanomyography for assessing neuromuscular function: a noninvasive approach; Phys Med Rehabil in N Am; 23(1); pp. 23-32; Feb. 2012.
Mamorita et al.; Development of a system for measurement and analysis of tremor using a three-axis accelerometer; Methods Inf Med; 48(6); pp. 589-594; epub Nov. 2009.
Maneski et al.; Electrical Stimulation for suppression of pathological tremor; Med Biol Eng Comput; 49(10); pp. 1187-1193; Oct. 2011.
Marsden et al.; Coherence between cerebellar thalamus, cortex and muscle in man; Brain; 123; pp. 1459-1470; Jul. 2000.
Marshall, Ryan, et al. "Bioelectrical stimulation for the reduction of inflammation in inflammatory bowel disease." Clinical Medicine Insights: Gastroenterology 8 (2015): CGast-S31779.
McAuley et al.; Physiological and pathological tremors and rhythmic central motor control; Brain; 123(Pt 8); pp. 1545-1567; Aug. 2000.
McIntyre et al.; Finite element analysis of current-density and electric field generated by metal microelectrodes; Annals of Biomedical Engineering; 29(3); pp. 227-235; Mar. 2001.
Meekins et al.; American Association of Neuromuscular & Electrodiagnostic Medicine evidenced- based review: use of surface electromyography in the diagnosis and study of neuromuscular disorders; Muscle Nerve 38(4); pp. 1219-1224; Oct. 2008.
Mehnert, Ulrich, et al. "Heart rate variability: an objective measure of autonomic activity and bladder sensations during urodynamics." Neurourology and urodynamics 28.4 (2009): 313-319.
Miguel et al.; Alcohol consumption and the incidence of Parkinson's disease; Ann. Neurol.; 54(2); pp. 170-175; May 15, 2003.
Miller et al.; Multiplexed microneedle-based biosensor array for characterization of metabolic acidosis; Talanta; 88; pp. 739-742; Jan. 2012 (author manuscript; 13 pgs.).
Miller et al.; Neurostimulation in the treatment of primary headaches; Pract Neurol; Apr. 11, 2016;16:pp. 362-375.
Milne et al.; Habituation to repeated in painful and non-painful cutaneous stimuli: A quantitative psychophysical study; Experimental Brain Research; 87(2); pp. 438-444; Nov. 1991.
Mommaerts et al.; Excitation and nerve conduction; in Comprehensive Human Physiology; Springer Berlin Heidelberg; Chap. 13; pp. 283-294; Mar. 1996.
Mones et al.; The response of the tremor of patients with Parkinsonism to peripheral nerve stimulation; J Neurology, Neurosurgery, and Psychiatry; 32(6); pp. 512-518; Dec. 1969.
Morgante et al.: How many parkinsonian patients are suitable candidates for deep brain stimulation of subthalamic nucleus?; Results of a Questionnaire, Partkinsonism Relat Disord; 13; pp. 528-531; Dec. 2007.
Munhoz et al; Acute effect of transcutaneous electrical nerve stimulation on tremor; Movement Disorders; 18(2); pp. 191-194; Feb. 2003.

Nardone et al.; Influences of transcutaneous electrical stimulation of cutaneous and mixed nerves on subcortical somatosensory evoked potentials; Electroenceph. Clin. Neurophysiol.; 74(1); pp. 24-35; Jan.-Feb. 1989.
Nonis et al.; Evidence of activation of vagal afferents by non-invasive vagus nerve stimulation: An electrophysiological study in healthy volunteers; Cephalalgia; pp. 1285-1293; vol. 37(13); Mar. 28, 2017.
Perez et al.; Patterned Sensory Stimulation Induces Plasticity in Reciprocal Ia Inhibition in Humans; The Journal of Neuroscience; 23(6); pp. 2014-2018; Mar. 2003.
Perlmutter et al.; Deep brain stimulation; Ann Rev Neurosci; 29; pp. 229-257; Jul. 2006.
Popovic-Bijelic, Ana, et al. "Multi-field surface electrode for selective electrical stimulation." Artificial organs 29.6 (2005): 448-452.
Prochazka et al.; Attenuation of pathological tremors by functional electrical stimulation I: Method; Annals of Biomedical Engineering; 20(2); pp. 205-224; Mar. 1992.
Pulliam et al.; Continuous in-home monitoring of essential tremor; Parkinsonism Relat Disord; 20(1); pp. 37-40; Jan. 2014.
Quattrini et al.; Understanding the impact of painful diabetic neuropathy; Diabetes/Metabolism Research and Reviews; 19, Suppl. 1; pp. S2-S8; Jan.-Feb. 2003.
Rocon et al.; Design and validation of a rehabilitation robotic exoskeleton for tremor assessment and suppression; IEEE Trans Neural Sys and Rehab Eng.; 15(3); pp. 367-378; Sep. 2007.
Silverstone et al.; Non-Invasive Neurostimulation in the Control of Familial Essential Tremor Using the Synaptic Neuromodulator; Conference Proceedings, International Functional Electrical Stimulation Society (IFES); Ed. Paul Meadows; 3 pgs.; May 1999.
Singer et al.; The effect of EMG triggered electrical stimulation plus task practice on arm function in chronic stroke patients with moderate-severe arm deficits; Restor Neurol Neurosci; 31(6); pp. 681-691; Oct. 2013.
Straube et al.; Treatment of chronic migraine with transcutaneous stimulation of the auricular branch of the vagal nerve (auricular t-VNS): a randomized, monocentric clinical trial; The Journal of Headache and Pain (2015) 16:63.
Takanashi et al.; A functional MRI study of somatotopic representation of somatosensory stimulation in the cerebellum; Neuroradiology; 45(3); pp. 149-152; Mar. 2003.
Tass et al.; Coordinated reset has sustained aftereffects in Parkinsonian monkeys; Ann Neurol; 72(5); pp. 816-820; Nov. 2012.
Tass et al.; Counteracting tinnitus by acoustic coordinated reset neuromodulation; Restorative neurology and Neuroscience; 30(2); pp. 137-159; Apr. 2012.
Tass; A Model of desynchronizing deep brain stimulation with a demand-controlled coordinated reset of neural subpopulations; Bioi Cybern; 89(2); pp. 81-88; Aug. 2003.
Thomas et al.; A review of posterior tibial nerve stimulation for faecal incontinence; Colorectal Disease; 2012 The Association of Coloproctology of Great Britain and Ireland. 15, pp. 519-526; Jun. 25, 2012.
Toloso et al.; Essential tremor: treatment with propranolol; Neurology; 25(11); pp. 1041; Nov. 1975.
Treager; Interpretation of skin impedance measurements; Nature; 205; pp. 600-601; Feb. 1965.
Valente; Novel methods and circuits for field shaping in deep brain stimulation; Doctoral thesis, UCL (University College London); 222 pgs.; 2011.
Vitton et al.; Transcutaneous posterior tibial nerve stimulation for fecalIncontinence in inflammatory bowel disease patients: a therapeutic option?; Inflamm Bowel Dis; vol. 15, No. 3, Mar. 2009; pp. 402-405.
Von Lewinski et al.; Efficacy of EMG-triggered electrical arm stimulation in chronic hemiparetic stroke patients; Restor Neurol Neurosci; 27(3); pp. 189-197; Jun. 2009.
Wardman et al.; Subcortical, and cerebellar activation evoked by selective stimulation of muscle and cataneous afferents: an fMRI study; Physiol. Rep.; 2(4); pp. 1-16; Apr. 2014.
Wiestler et al.; Integration of sensory and motor representations of single fingers in the human; J. Neurophysiol.; 105(6); pp. 3042-3053; Jun. 2011.

(56) References Cited

OTHER PUBLICATIONS

Woldag et al.; Evidence-based physiotherapeutic concepts for improving arm and hand function in stroke patients R A review; J Neurol; 249(5); pp. 518-528; May 2002.
Woolf et al.; Peripheral nerve injury triggers central sprouting of myelinated afferents; Nature; 355(6355); pp. 75-78; Jan. 1992.
Yarnitsky et al.; Nonpainful remote electrical stimulation alleviates episodic migraine pain; Neurology 88; pp. 1250-1255; Mar. 28, 2017.
Yeh, Kuei-Lin, Po-Yu Fong, and Ying-Zu Huang. "Intensity sensitive modulation effect of theta burst form of median nerve stimulation on the monosynaptic spinal reflex." Neural plasticity 2015 (2015) in 8 pages.
Yilmaz, Ozlem O., et al. "Efficacy of EMG-biofeedback in knee osteoarthritis." Rheumatology international 30.7 (2010): 887-892.
Zhang et al.; Neural oscillator based control for pathological tremor suppression via functional electrical stimulation; Control Engineering Practice; 19(1); pp. 74-88; Jan. 2011.
Zorba et al.; Overactive bladder and the pons; Rize University, Medical Faculty, Department of Urology; 123-124; Undated.
Zwarts et al.; Multichannel surface EMG: basic aspects and clinical utility; Muscle Nerve; 28(1); pp. 1-17; Jul. 2003.
International Search Report and Written Opinion dated Nov. 16, 2017 in application No. PCT/US17/48424.
U.S. Appl. No. 17/107,435 (published as U.S. Pub. No. 2021/0100999), filed Nov. 30, 2020.
PCT, PCT/US2019/039193 (published as PCT Pub. No. WO 2020/006048), Jun. 26, 2019.
U.S. Appl. No. 14/271,669 (published as U.S. Pub. No. 2014/0336722), filed Nov. 13, 2014.
PCT, PCT/US2015/033809 (published as WO 2015/187712), Jun. 2, 2015.
U.S. Appl. No. 15/354,943 (now U.S. Pat. No. 9,802,041), filed Nov. 17, 2016.
U.S. Appl. No. 15/721,475 (now U.S. Pat. No. 10,179,238), filed Sep. 29, 2017.
U.S. Appl. No. 15/721,480 (now U.S. Pat. No. 10,173,060), filed Sep. 29, 2017.
U.S. Appl. No. 16/242,983 (now U.S. Pat. No. 10,549,093), filed Jan. 8, 2019.
U.S. Appl. No. 16/247,310 (now U.S. Pat. No. 10,561,839), filed Jan. 14, 2019.
U.S. Appl. No. 16/780,758 (now U.S. Pat. No. 10,905,879), filed Feb. 3, 2020.
U.S. Appl. No. 16/792,100 (now U.S. Pat. No. 10,960,207), filed Feb. 14, 2020.
U.S. Appl. No. 17/164,576 (published as U.S. Pub. No. 2021/0330974), filed Feb. 1, 2021.
U.S. Appl. No. 17/216,372 (published as U.S. Pub. No. 2021/0308460), filed Mar. 29, 2021.
PCT, PCT/US2016/037080 (published as WO 2016/201366), Jun. 10, 2016.
U.S. Appl. No. 15/580,631 (now U.S. Pat. No. 10,765,856), filed Dec. 7, 2017.
U.S. Appl. No. 17/013,396 (published as U.S. Pub. No. 2021/0052883), filed Sep. 4, 2020.
PCT, PCT/US2017/014431 (published as WO 2017/132067), Jan. 20, 2017.
U.S. Appl. No. 16/071,056 (now U.S. Pat. No. 11,344,722), filed Jul. 18, 2018.
U.S. Appl. No. 17/663,004, filed May 11, 2022.
PCT, PCT/US2018/025752 (published as WO 2018/187241), Apr. 2, 2018.
U.S. Appl. No. 16/500,377 (now U.S. Pat. No. 11,331,480), filed Apr. 2, 2018.
U.S. Appl. No. 17/663,010, filed May 11, 2022.
PCT, PCT/US2016/045038 (published as WO 2017/023864), Aug. 1, 2016.
U.S. Appl. No. 15/748,616 (published as U.S. Pub. No. 2020/0093400), filed Jan. 29, 2018.
PCT, PCT/US2016/053513 (published as WO 2017/053847), Sep. 23, 2016.
U.S. Appl. No. 15/762,043 (now U.S. Pat. No. 10,603,482), filed Mar. 21, 2018.
U.S. Appl. No. 16/833,388 (published as U.S. Pub. No. 2020/0289814), filed Mar. 27, 2020.
PCT, PCT/US2017/040920 (published as WO 2018/009680), Jul. 6, 2017.
U.S. Appl. No. 16/241,846, filed Jan. 7, 2019.
U.S. Appl. No. 17/080,544 (published as U.S. Pub. No. 2021/0113834), filed Oct. 26, 2020.
PCT, PCT/US2017/048424 (published as WO 2018/039458), Aug. 24, 2017.
U.S. Appl. No. 16/327,780 (published as U.S. Pub. No. 2021/0283400), filed Feb. 22, 2019.
PCT, PCT/US2019/013966 (published as WO 2019/143790), Jan. 17, 2019.
U.S. Appl. No. 16/962,810 (published as U.S. Pub. No. 2021/0252278), filed Jan. 17, 2019.
PCT, PCT/US2019/030458 (published as WO 2019/213433), May 2, 2019.
U.S. Appl. No. 17/052,483 (published as U.S. Pub. No. 2021/0244940), filed Jan. 17, 2019.
PCT, PCT/US2019/053297 (published as WO 2020/069219), Apr. 26, 2019.
U.S. Appl. No. 17/279,048 (published as U.S. Pub. No. 2021/0402172), filed Mar. 23, 2021.
PCT, PCT/US2019/057674 (published as WO 2020/086726), Oct. 23, 2019.
U.S. Appl. No. 17/287,471 (published as U.S. Pub. No. 2021/0379374), filed Apr. 21, 2021.
Fiorentino, M., A. E. Uva, and M. M. Foglia. "Self calibrating wearable active running asymmetry measurement and correction." Journal of Control Engineering and Applied Informatics 13.2 (2011): 3-8. (Year: 2011).
Krishnamoorthy et al; Gait Training After Stroke: A pilot study combining a gravity balanced orthosis, functional electrical stimulation and visual feedback, Journal of Neurologic Physical Therapy, vol. 32, No. 4, pp. 192-202, 2008.
Popovi Maneski et al.; Electrical stimulation for the suppression of pathological tremor; Medical & Biological Engineering & Computing; 49(10); pp. 1187-1193; Oct. 2011.
Sigrist et al; Augmented visual, auditory, haptic and multimodal feedback in motor learning; A review. Psychonomic Bulletin & Review, 20(1), pp. 21-53 (2012).
Solomonow, Met al. "Studies Toward Spasticity Suppression With High Frequency Electrical Stimulation". Orthopedics, vol. 7, No. 8, 1984, pp. 1284-1288. Slack, Inc., https://doi.org/10.3928/0147-7447-19840801-11 (Year: 1998).
Tracey; The inflammatory reflex; Nature; vol. 420; pp. 853-859; Dec. 19/26, 2002.
Barath et al., 2020, Brain metabolic changes with longitudinal transcutaneous afferent patterned stimulation in essential tremor subjects, Tremor and Other Hyperkinetic Movements, 10(1):52, pp. 1-10.
Brillman et al., 2022, Real-world evidence of transcutaneous afferent patterned stimulation for essential tremor, Tremor and Other Hyperkinetic Movements, 12(1):27, pp. 1-11.
Ferreira et al., 2019, MDS evidence-based review of treatments for essential tremor, Movement Disorders, 34(7):950-958.
Gupta et al., 2021, Exploring essential tremor: results from a large online survey, Clinical Parkinsonism & Related Disorders, 5:100101, 4 pp.
Haubenberger et al., 2018, Essential Tremor, The New England Journal of Medicine, 378:1802-1810 and Supplementary Appendix.
Hellwig et al., Feb. 17, 2001, Tremor-correlated cortical activity in essential tremor, The Lancet, 357:519-523.
Hernandez-Martin et al., 2021, High-fidelity transmission of high-frequency burst stimuli from peripheral nerve to thalamic nuclei in children with dystonia, Scientific Reports, 11:8498, 9 pp.
Isaacson et al., 2020, Prospective home-use study on non-invasive neuromodulation therapy for essential tremor, Tremor and Other Hyperkinetic Movements, 10(1):29, pp. 1-16.

(56) References Cited

OTHER PUBLICATIONS

Lin et al., 2018, Noninvasive neuromodulation inessential tremor demonstrates relief in a sham-controlled pilot trial, Movement Disorders, 33(7):1182-1183.
Llinas et al., Dec. 21, 1999, Thalamocortical dysrhythmia: a neurological and neuropsychiatric syndrome characterized by magnetoencephalography, PNAS, 96(26):15222-15227.
Lyons et al., 2021, Essential tremor in adult patients, International Essential Tremor Foundation, 16 pp.
Pahwa et al., 2018, An acute randomized controlled trial of noninvasive peripheral nerve stimulation in essential tremor, Neuromodulation, 22:537-545.
Peng et al., 2015, Flexible dry electrode based on carbon nanotube/polymer hybrid micropillars for biopotential recording, Sensor and Actuatora A: Physical, 235:48-65.
Perez-Reyes, Jan. 2003, Molecular physiology of low-voltage-activated T-type calcium channels, Physiol. Rev. 83:117-161.
Wallerberger, Apr. 4, 2019, Efficient Estimation of Autocorrelation Spectra, ArXiv.org, https://arxiv.org/abs/1810.05079.
Cala Trio Health Care Professional Guide (Jul. 2020).
Cala Trio Health Care Professional Guide (Nov. 2019).
Chang, M.D., Qwang-Yuen et al., Effect of Electroacupuncture and Transcutaneous Electrical Nerve Stimulation at Hegu (LI.4) Acupuncture Point on the Cutaneous Reflect, 27 Acupuncture & Electro-Therapeutics Res., Int. J. 191-202 (2002).
Javidan, et al., Attenuation of Pathological Tremors by Functional Electrical Stimulation II: Clinical Evaluation, 20 Annals of Biomedical Engineering 225 (1992).
Knutson et al., Neuromuscular Electrical Stimulation for Motor Restoration in Hemiplegia. Phys Med Rehabil Clin N A,. Nov. 2015; 26(4):729-745. Published online Aug. 14, 2015. Doi: 10.1016/j.pmr.2015.06.002.

\* cited by examiner

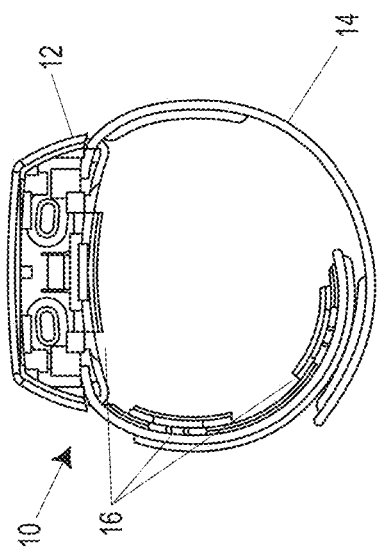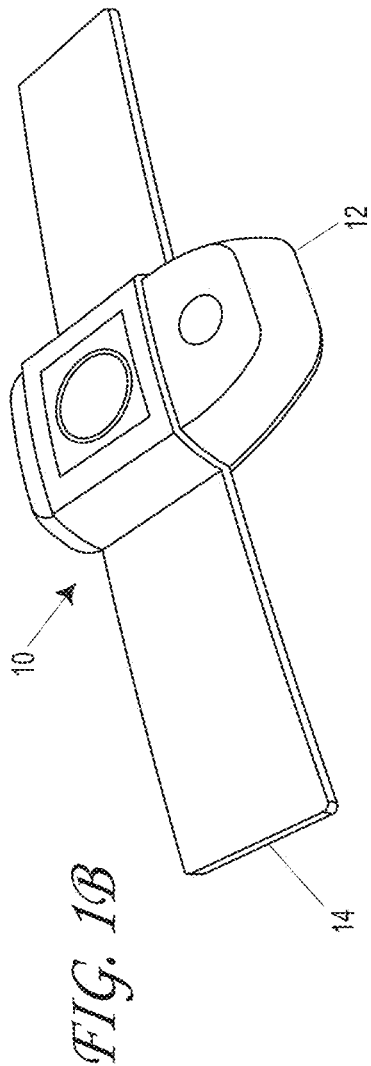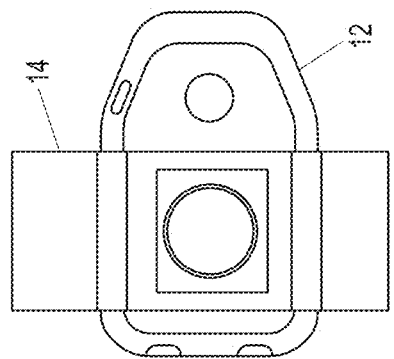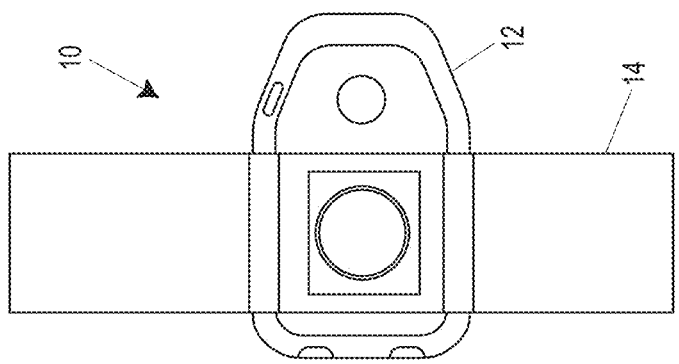

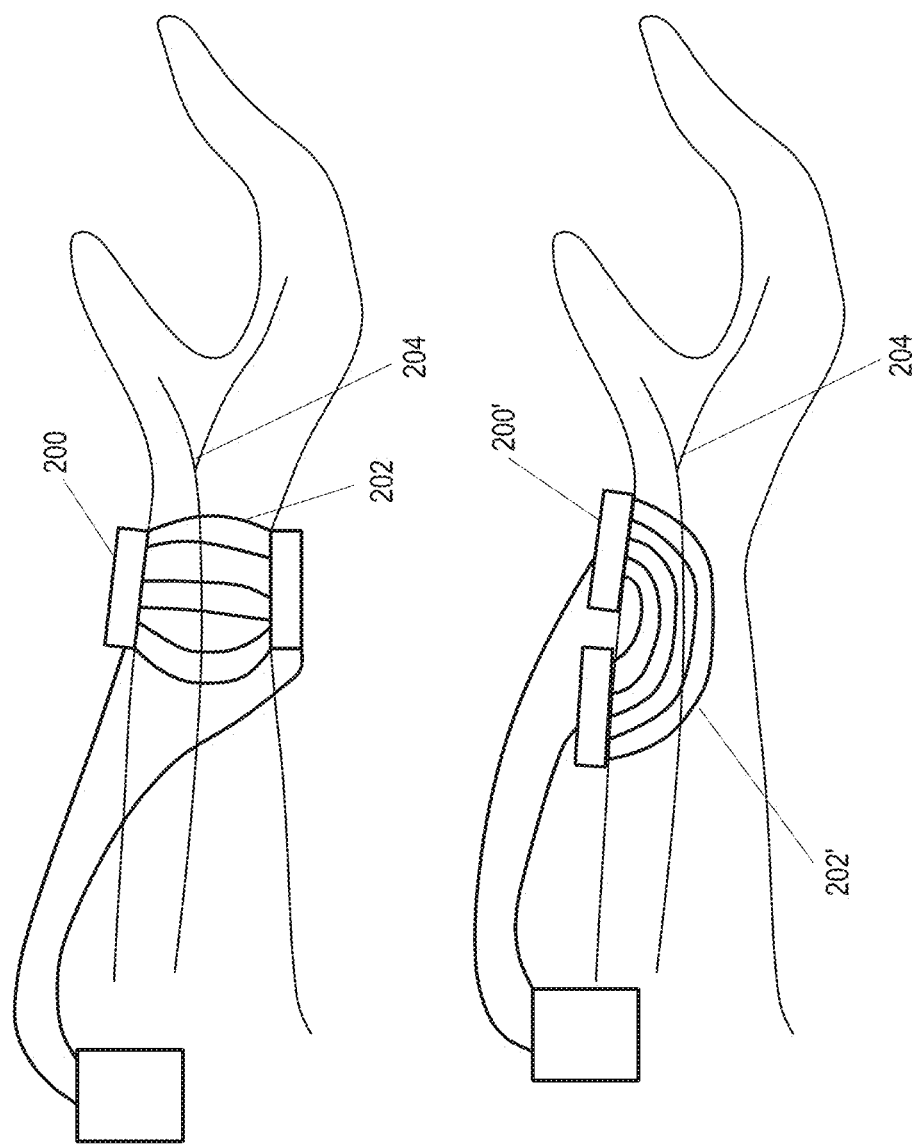

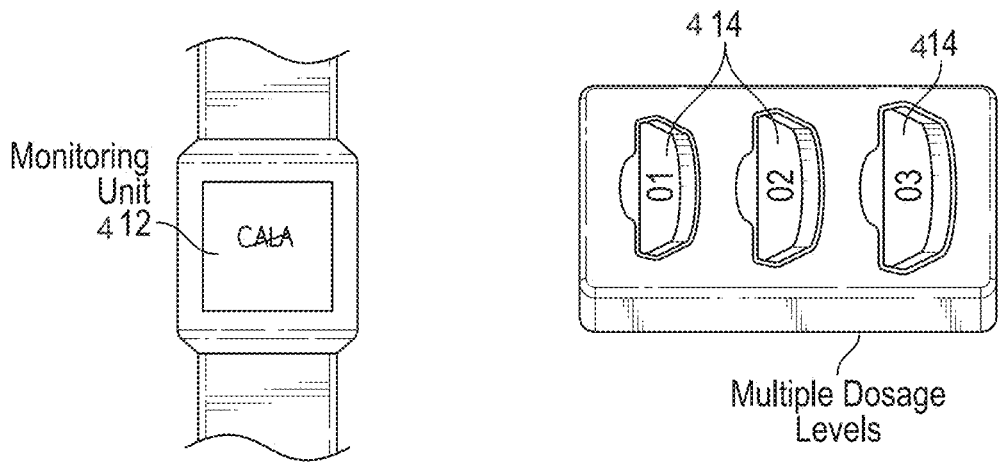
FIG. 4A
FIG. 4B
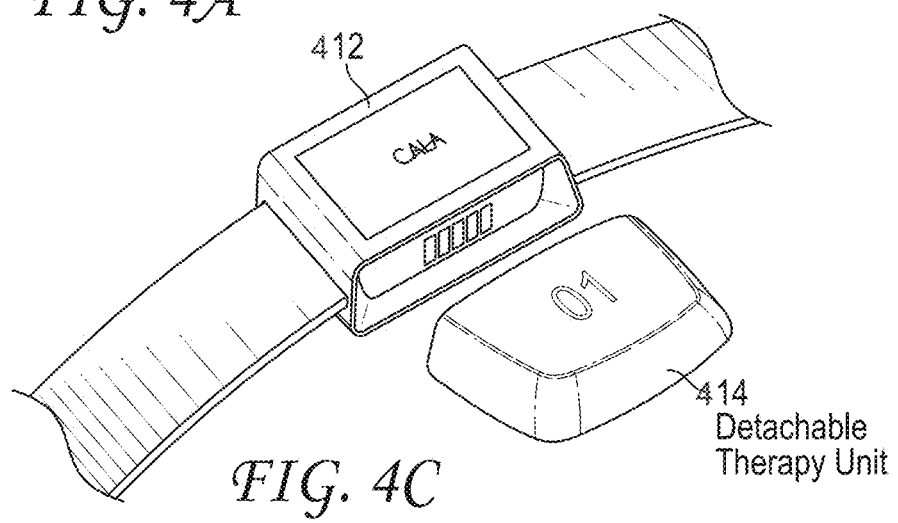
FIG. 4C
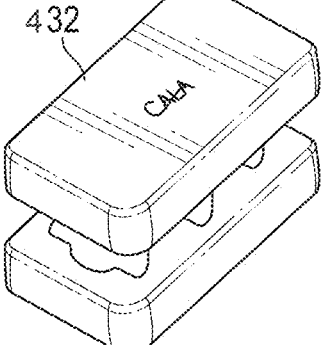
FIG. 4D

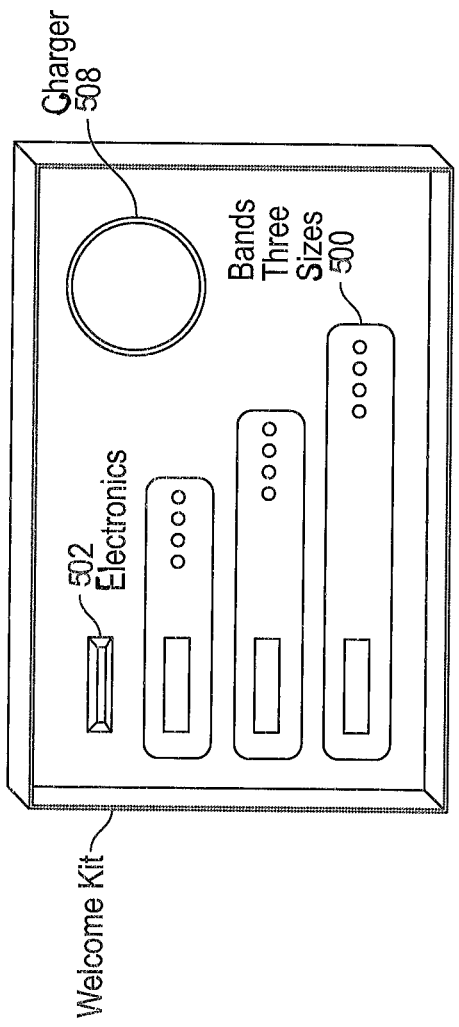
FIG. 5B
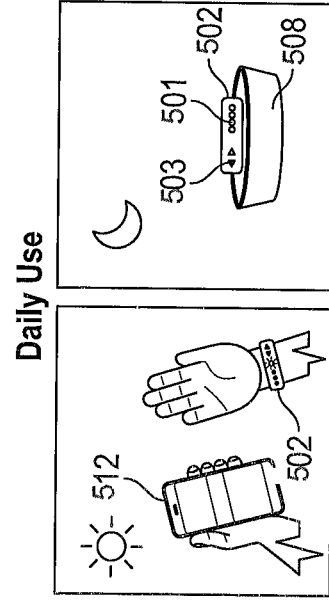
FIG. 5E
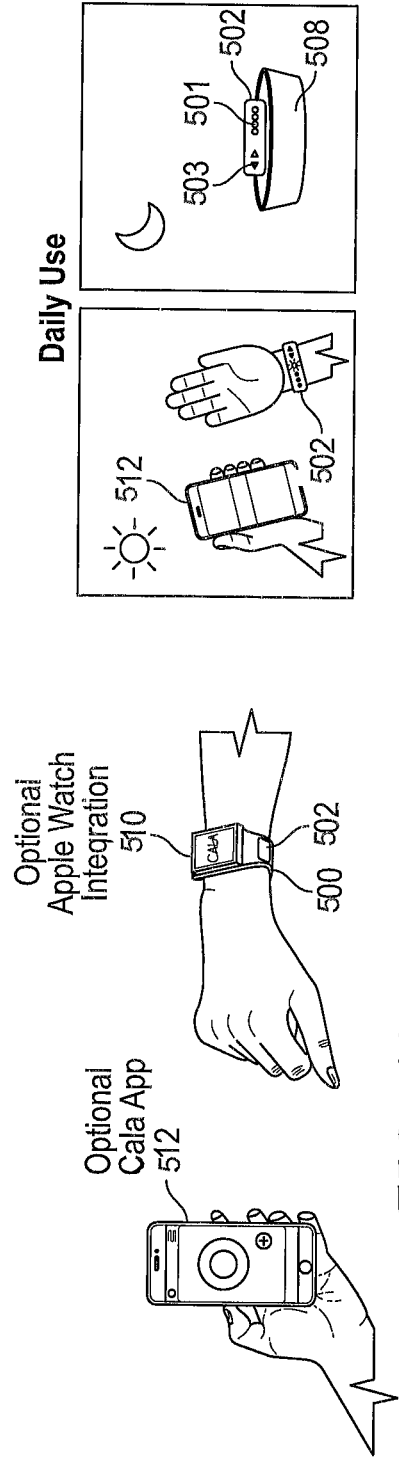
FIG. 5D
FIG. 5C

POSTERIOR VIEW
LEFT - SUPERFICIAL MUSCULATURE
RIGHT - YANG SUPERFICIAL MERIDIANS
ARM YANG MERIDIANS & SHICHEN    LEG YANG MERIDIANS & SHICHEN
LI - LARGE INTESTINE 1 - 3 PM    ST- STOMACH MERIDIAN 7 - 9 AM
SI - SMALL INTESTINE 1 - 3 PM    BL - BLADDER MERIDIAN 3 - 5 PM
TW - TRIPLE WARMER 9 - 11 PM    GB - GALL BLADDER MERIDIAN 11 PM - 1 AM
GV - GOVERNING VESSEL (CENTERLINE)

SYSTEMS AND METHODS FOR TREATING CARDIAC DYSFUNCTION THROUGH PERIPHERAL NERVE STIMULATION

INCORPORATION BY REFERENCE TO ANY PRIORITY APPLICATIONS

This application is the U.S. National Stage of PCT/US2017/048424 filed on Aug. 24, 2017, which in turn claims the benefit under 35 U.S.C. § 119(e) as a nonprovisional application of U.S. Prov. App. No. 62/379,253 filed Aug. 25, 2016 and U.S. Prov. App. No. 62/423,169 filed on Nov. 16, 2016, both of which are incorporated by reference in their entireties. Any and all applications for which a foreign or domestic priority claim is identified in the Application Data Sheet as filed with the present application are hereby incorporated by reference under 37 CFR 1.57.

BACKGROUND

Field of the Invention

Embodiments of the invention relate generally to the treatment of cardiac dysfunction, including dysrhythmias and hypertension, and more specifically to systems and methods of treating cardiac dysrhythmias, including atrial fibrillation, as well as hypertension through noninvasive peripheral nerve stimulation.

Description of the Related Art

The main function of the heart to pump oxygenated blood throughout the body and deoxygenated blood back to the lungs. Pumping blood is achieved by coordinated contraction of four chambers within the heart on a regular and continuous basis. An intrinsic conduction system originates and conducts a rhythmic electrical signal within the heart that drives coordinated contraction. However, to respond to external factors, heart rate and contractility are regulated by the autonomic nervous system and endocrine system. Specifically, the autonomic nervous system can regulate heart rate, blood pressure, respiration rate, body temperature, and other visceral activities within the body to maintain stability.

A variation in the normal beating pattern or rhythm of the heart is called a cardiac dysrhythmia or arrhythmia; hereafter arrhythmia and dysrhythmia are used synonymously. Cardiac dysrhythmia may occur at the level of atria, ventricles or arise from junctions where the electrical impulse starts. These broad groupings based on the origin of the malfunction of the beat are further classified into subgroups based on the exact pattern of the abnormal heart beat. Atrial arrhythmia may manifest as, for example, atrial flutter, atrial fibrillation, multi-focal atrial tachycardia or atrial premature contractions. Ventricular arrhythmia may manifest as, for example, premature ventricular contractions, ventricular tachycardia, torsades de pointes, or as ventricular fibrillation. Junctional arrhythmias may present in the form of a supraventricular tachycardia such as PSVT or as premature junctional contractions. Heart block, partial (first degree, second degree (Mobitz I and Mobitz II)) or third degree-complete, which is a condition of bradycardia is also a type of arrhythmia.

Cardiac dysrhythmia is prevalent in more than 5% of the population in US and results in significant mortality and morbidity. Cardiac dysrhythmia is associated with and a major risk factor for stroke, heart failure and hypertension. Because cardiac dysrhythmia is so prevalent, much research and development has focused on finding new and improved ways of reducing blood pressure.

Depending on the type of dysrhythmia, therapy could be administration of medications and/or electrical manipulations and/or surgery. The anti-arrhythmic medications are often combined with anti-clotting or anti-coagulant drugs. Other than medications, certain people have benefited positively by applying electrical stimulations through electrodes, either internally or externally. Electrical stimulation via cardioversion and defibrillation via an external defibrillator or automatic implantable cardioverter-defibrillator (AICD) can be first-line therapy in treatment of ventricular fibrillation, which is a life-threatening specific symptom of cardiac dysrhythmia. Temporary or permanent cardiac pacing with pacemakers is another therapy for certain arrhythmias. Surgical options include catheter ablation, which is often used for treating atrial fibrillation. However, for many patients, the efficacy of these treatments is either not sufficient or decreases over time. Also, anti-arrhythmic medications can have several short and long-term side effects and/or drug-drug interactions, so new systems and methods for treating cardiac dysfunction are needed.

Hypertension, which is a condition of having long term high blood pressure, is associated with and is a major risk factor for many cardiovascular diseases, such as coronary artery disease, stroke, heart failure, and peripheral vascular disease, as well as other diseases such as vision loss and chronic kidney disease. These diseases, particularly the cardiovascular diseases, account for a large percentage of the mortality and morbidity in the United States and the rest of the world. Because hypertension is so prevalent, with estimates that over 1 billion adults suffer from hypertension, much research and development has focused on finding new and improved ways of reducing blood pressure.

Ventricular dyssynchrony is a difference in the timing, or lack of synchrony, of contractions in different ventricles in the heart. Large differences in timing of contractions can reduce cardiac efficiency and is correlated with heart failure, of which hypertension is one of the leading preventable causes. Thus, measurement of dyssynchrony could be used as an effective outcome measure of a hypertension therapy.

Treatments include lifestyle modification such as exercise, dietary changes, and weight loss. Other treatments primarily include various types of medications. Often, these treatments are used in combination. However, for many patients, the efficacy of these treatments is either not sufficient or decreases over time.

Therefore, it would be desirable to provide additional ways of treating cardiac dysfunction including hypertension and/or arrhythmias that can be used instead of or in combination with other hypertension and/or arrhythmia treatments.

SUMMARY

Some embodiments of the present invention relate generally to the treatment of cardiac dysrhythmias and/or hypertension, and more specifically to systems and methods of treating hypertension and/or cardiac dysrhythmias, including but not limited to atrial fibrillation, through noninvasive peripheral nerve stimulation. In some embodiments, disclosed herein is a system for treating cardiac dysrhythmia in a patient. The system can include a peripheral nerve stimulator including a pulse generator and at least two electrodes configured to deliver electrical stimulation to a nerve, acupressure point, or meridian in the patient's limbs. The stimulation can be sufficient in some embodiments to reduce one or more of: blood pressure, the occurrence rate of cardiac arrhythmia, duration of cardiac arrhythmia, and cardioversion. The system can also include one, two, or more sensors. The stimulator and/or the sensor could be implantable within a patient or wearable. The stimulator and/or the sensor could be percutaneous or transcutaneous in some embodiments.

In some embodiments, systems and methods for treatment of cardiac dysfunction can include any number of features as disclosed herein in the specification.

In some embodiments, disclosed herein is a transcutaneous method for treating cardiac arrhythmias and/or hypertension with selective activation. The method can include, for example, positioning a first peripheral nerve effector on a patient's skin on an extremity of the patient; delivering a first electrical nerve stimulation signal transcutaneously to the first peripheral nerve effector to stimulate a first peripheral nerve sufficient to modify at least one brain or spinal cord autonomic feedback loop relating to the cardiac arrhythmia or hypertension. The first electrical nerve stimulation signal can preferentially, or selectively only activate on or more of A-alpha, A-beta, A-delta, B, or C-fibers of the first peripheral nerve. The first peripheral nerve could be an upper extremity nerve, such as, for example, the median nerve, the radial nerve, the medial cutaneous nerve, the lateral cutaneous nerve, the musculocutaneous nerve, or the ulnar nerve; or a lower extremity nerve such as, for example, the tibial nerve, the saphenous nerve, the common peroneal nerve, the femoral nerve, the sacral nerve, the sciatic nerve, and the sural nerve. The first electrical nerve stimulation signal could include burst or continuous stimulation, and of a selected waveform that could a biphasic square waveform or sinusoidal in some cases. The pulse width could be, for example, between about 50 us and about 100 µs, between about 150 us and about 200 µs, between about 300 us and about 400 µs, or other ranges included any two of the aforementioned values. In some embodiments, the electrical stimulation signal could have a frequency of about 5 Hz, about 250 Hz, or about 2,000 Hz. In some embodiments, the first peripheral nerve effector can include at least first and second electrodes. The electrodes can be substantially aligned along the length of the nerve axon in some cases. In some embodiments, the method can include positioning a second peripheral nerve effector on a patient's skin on the extremity of the patient; and delivering a second electrical nerve stimulation signal transcutaneously to the second peripheral nerve effector to stimulate a second peripheral nerve sufficient to modify at least one brain or spinal cord autonomic feedback loop and balance parasympathetic or sympathetic nervous system activity of the patient. The second peripheral nerve could be different from the first peripheral nerve, and selected from, for example, any of the nerves described elsewhere herein. The method can also include receiving an input relating to autonomic nervous system activity of the patient, including, for example, receiving data from a sensor that measures heart rate variability of the patient; and/or receiving data from a sensor that measures at least one of electrodermal activity, thermometry, and ECG information of the patient. The method can also include positioning any number of the peripheral nerve effectors over one or more of: the C6, C7, C8, T1, T2, T3, T4, T5, T6, T7, T8, T9, T10, T11, T12, L1, L2, L3, L4, L5, S1, S2, S3, and/or S4 dermatomes. In some embodiments, a peripheral nerve effector can be positioned on an extremity of the patient offset from one or more nerves, such as the median nerve, radial nerve, or ulnar nerve for example, and targeting a target nerve, such as a cutaneous nerve. The arrhythmia to be treated can be, for example, atrial fibrillation, atrial flutter, supraventricular tachycardia, or ventricular tachycardia. In some embodiments, an electrical nerve stimulation signal can preferentially activate, or selectively activate only one of A-alpha, A-beta, A-delta, B, or C-fibers of the first peripheral nerve.

Also disclosed herein in some embodiments is a wearable transcutaneous system for treating cardiac arrhythmias or hypertension with selective activation. The system can include any number of the following features, or others disclosed elsewhere in the specification. The system can include, for example, a controller; a first peripheral nerve effector configured to be positioned on a patient's skin on an extremity of the patient; and/or at least one biomedical sensor or data input source configured to provide feedback information. The controller can be configured to generate a first electrical nerve stimulation signal transcutaneously to the first peripheral nerve effector to stimulate a first peripheral nerve sufficient to modify at least one brain or spinal cord autonomic feedback loop relating to the cardiac arrhythmia or hypertension. The first electrical nerve stimulation signal can preferentially or selectively activate one or more of A-alpha, A-beta, A-delta, or C-fibers of the first peripheral nerve. The system can also include a second peripheral nerve effector configured to be positioned on the patient's skin on the extremity of the patient. The controller can be configured to generate a second electrical nerve stimulation signal transcutaneously to the second peripheral nerve effector to stimulate a second peripheral nerve sufficient to modify at least one brain or spinal cord autonomic feedback loop relating to the cardiac arrhythmia or hypertension. The second electrical nerve stimulation signal can preferentially activate one or more of A-alpha, A-beta, A-delta, B, or C-fibers of the second peripheral nerve. The feedback information can include, for example, heart rate variability and/or galvanic skin response. The first peripheral nerve could be an upper extremity nerve, such as, for example, the median nerve, the radial nerve, the medial cutaneous nerve, the lateral cutaneous nerve, the musculocutaneous nerve, or the ulnar nerve; or a lower extremity nerve such as, for example, the tibial nerve, the saphenous nerve, the common peroneal nerve, the femoral nerve, the sacral nerve, the sciatic nerve, and the sural nerve. The first electrical nerve stimulation signal could include burst or continuous stimulation, and of a selected waveform that could a biphasic square waveform or sinusoidal in some cases. The pulse width could be, for example, between about 50 µs and about 100 µs, between about 150 µs and about 200 µs, between about 300 µs and about 400 µs, or other ranges included any two of the aforementioned values. In some embodiments, the electrical stimulation signal could have a frequency of about 5 Hz, about 250 Hz, or about 2,000 Hz. In some embodiments, the first peripheral nerve effector can include at least first and second electrodes. The electrodes can be substantially aligned along the length of the nerve axon in some cases. In some embodiments, the system can include a second peripheral nerve effector configured to be positioned on a patient's skin on the extremity of the patient; and configured to deliver a second electrical nerve stimulation signal transcutaneously to the second peripheral nerve effector to stimulate a second peripheral nerve sufficient to modify at least one brain or spinal cord autonomic feedback loop and balance parasympathetic or sympathetic nervous system activity of the patient. The second peripheral nerve could be different from the first peripheral nerve, and selected from, for example, any of the nerves described elsewhere herein. The system can also be configured to receive an input relating to autonomic nervous system activity of the patient, including, for example, receiving data from a sensor that measures heart rate variability of the patient; and/or receiving data from a sensor that measures at least one of electrodermal activity, thermometry, and ECG information of the patient.

Also disclosed herein are methods for treating cardiac arrhythmias or hypertension, that can include one or more of positioning a first peripheral nerve effector on a patient's skin on an upper extremity of the patient to stimulate a first peripheral nerve selected from the group consisting of one of a median nerve, radial nerve, and ulnar nerve of the patient; positioning a second peripheral nerve effector on the patient's skin on the upper extremity of the patient to stimulate a second peripheral nerve different from the first peripheral nerve; delivering a first electrical nerve stimulation signal transcutaneously to the first peripheral nerve effector to stimulate the first peripheral nerve sufficient to modify at least one brain or spinal cord autonomic feedback loop relating to the cardiac arrhythmia or hypertension; and/or delivering a second electrical nerve stimulation signal transcutaneously to the second peripheral nerve effector to stimulate the second peripheral nerve sufficient to modify at least one brain or spinal cord autonomic feedback loop relating to the cardiac arrhythmia or hypertension. The first electrical nerve stimulation signal and the second electrical nerve stimulation signal can be coordinated such that stimulation from the first peripheral nerve effector and stimulation from the second peripheral nerve effector activate the brachial plexus concurrently. The second electrical nerve stimulation signal can occur simultaneously or substantially simultaneously with delivering the first electrical nerve stimulation signal. Delivering the second electrical nerve stimulation signal can be offset temporally from delivering the first electrical nerve stimulation signal, such as between about 1.0 millisecond to about 2.1 milliseconds in some cases. The method can also include performing a nerve conduction study to measure a nerve conduction velocity of the first peripheral nerve and the second peripheral nerve. The offset can be determined from the measured nerve conduction velocity of the first peripheral nerve and the second peripheral nerve. The nerve stimulation signals can be delivered in alternating and/or rhythmic patterns, such as at an alternating frequency of between about 4 Hz and about 12 Hz. The alternating frequency can be timed to a cardiac rhythm event. The nerve stimulation signals can be delivered in a pseudorandom pattern, and/or be adjusted based on feedback received regarding the autonomic balance of the patient. The feedback can include, for example, measured heart rate variability of the patient, such as a ratio of absolute low frequency to absolute high frequency of heart rate variability of the patient. The first peripheral nerve effector and the second peripheral nerve effector span a plurality of dermatomes on the patient, such as any of the dermatomes mentioned herein. The dermatomes can be stimulated at a pre-determined interval.

Also disclosed herein in some embodiments are wearable systems for treating cardiac arrhythmias or hypertension. The system can include any number of the following features, or others disclosed elsewhere in the specification. The systems can include any number of a controller; a first peripheral nerve effector configured to be positioned on a patient's skin on an extremity of the patient; a second peripheral nerve effector configured to be positioned on the patient's skin on the extremity of the patient; and at least one biomedical sensor or data input source configured to provide feedback information. The controller can be configured to generate a first electrical nerve stimulation signal transcutaneously to the first peripheral nerve effector to stimulate a first peripheral nerve sufficient to modify at least one brain or spinal cord autonomic feedback loop relating to the cardiac arrhythmia or hypertension. The controller can also be configured to generate a second electrical nerve stimulation signal transcutaneously to the second peripheral nerve effector to stimulate a second peripheral nerve sufficient to modify at least one brain or spinal cord autonomic feedback loop relating to the cardiac arrhythmia or hypertension. The controller can also be configured to coordinate the first electrical nerve stimulation signal and the second electrical nerve stimulation signal such that stimulation from the first peripheral nerve effector and stimulation from the second peripheral nerve effector activate the brachial plexus concurrently, such as simultaneously or substantially simultaneously with delivering the first electrical nerve stimulation signal. The controller can be configured to deliver the second electrical nerve stimulation signal offset temporally from delivering the first electrical nerve stimulation signal, such as between about 1.0 and about 2.1 milliseconds. The controller can be configured to deliver electrical nerve stimulation signals in alternating, random, pseudorandom, and/or rhythmic patterns, such as at an alternating frequency of between about 4 Hz and about 12 Hz. The rhythmic pattern can be timed or synchronized with a measured heart rhythm event. The controller can be configured to adjust at least one of the first electrical stimulation signal and the second electrical nerve stimulation signal based on feedback received regarding the autonomic balance of the patient. The feedback can be, for example, measured heart rate variability of the patient, e.g., a ratio of absolute low frequency to absolute high frequency of heart rate variability of the patient. The controller can be configured to receive recorded measurements regarding the nerve conduction velocity of the first peripheral nerve and the second peripheral nerve, and coordinate the first electrical nerve stimulation signal and the second electrical nerve stimulation signal based upon the recorded measurements.

In some embodiments, disclosed herein are methods for treating cardiac arrhythmias or hypertension. The methods can include any number of the following: positioning a first peripheral nerve effector on a patient's skin on an upper extremity of the patient to stimulate a first peripheral nerve selected from the group consisting of one of a median nerve, radial nerve, and ulnar nerve of the patient; positioning a second peripheral nerve effector on a tragus of an ear of the patient to stimulate a second peripheral nerve associated with a parasympathetic nervous pathway of the patient; delivering a first electrical nerve stimulation signal transcutaneously to the first peripheral nerve effector to stimulate the first peripheral nerve sufficient to modify at least one brain or spinal cord autonomic feedback loop relating to the cardiac arrhythmia or hypertension; and delivering a second electrical nerve stimulation signal transcutaneously to the second peripheral nerve effector to stimulate the second peripheral nerve sufficient to modify at least one brain or spinal cord autonomic feedback loop relating to the cardiac arrhythmia or hypertension. The first electrical nerve stimulation signal and the second electrical nerve stimulation signal can be configured to balance parasympathetic and sympathetic nervous system activity of the patient. The method can also include monitoring sympathetic and parasympathetic activity in the patient. The method can also include adjusting the first electrical nerve stimulation signal upon identifying abnormal sympathetic activity in the patient. The method can also include adjusting the second electrical nerve stimulation signal upon identifying abnormal parasympathetic activity in the patient.

Also disclosed herein in some embodiments is a wearable system for treating cardiac arrhythmias or hypertension. The system can include any number of the following features, or others disclosed elsewhere in the specification. The system can include a first peripheral nerve effector configured to be positioned on a patient's skin on an extremity of the patient; a second peripheral nerve effector configured to be positioned on a tragus of an ear of the patient; and/or at least one biomedical sensor or data input source configured to provide feedback information. The controller can be configured to generate a first electrical nerve stimulation signal transcutaneously to the first peripheral nerve effector to stimulate a first peripheral nerve sufficient to modify at least one brain or spinal cord autonomic feedback loop relating to the cardiac arrhythmia or hypertension. The controller can also be configured to generate a second electrical nerve stimulation signal transcutaneously to the second peripheral nerve effector to stimulate a second peripheral nerve associated with a parasympathetic nervous pathway of the patient to modify at least one brain or spinal cord autonomic feedback loop relating to the cardiac arrhythmia or hypertension. The controller can also be configured to adjust the first electrical nerve stimulation signal and the second electrical nerve stimulation signal to balance parasympathetic and sympathetic nervous system activity of the patient. The controller can be configured to adjust the first electrical nerve stimulation signal upon identifying abnormal sympathetic and/or parasympathetic activity in the patient.

Also disclosed herein is a method for treating cardiac arrhythmias or hypertension. The method can include any number of assessing at least one of sympathetic and parasympathetic activity of a subject and determining the presence of abnormal sympathetic or parasympathetic activity in the subject; stimulating a first nerve associated operably connected to the brachial plexus sufficient to have a therapeutic effect on cardiac arrhythmias or hypertension if abnormal sympathetic activity is present; and stimulating the tragus of the ear sufficient to have a therapeutic effect on cardiac arrhythmias or hypertension if abnormal parasympathetic activity is present. Stimulation can be in some cases only electrical transcutaneous stimulation, can include exciting or inhibiting nerve activity of the first nerve. Stimulating can involve both the first nerve and the tragus of the ear if both abnormal sympathetic activity and abnormal parasympathetic activity are present. Assessing at least one of sympathetic and parasympathetic activity of a subject comprises measuring HRV in the subject, such as with a wrist-worn device, and also include measuring heart rate and/or electrodermal activity. The first nerve can be, for example, the median, radial, ulnar, median cutaneous, lateral cutaneous, or other nerves as discussed herein.

Also disclosed herein are methods of treating cardiac arrhythmias or hypertension, that can involve electrically stimulating a first peripheral nerve; assessing at least one of sympathetic and parasympathetic activity of a subject and determining abnormal sympathetic or parasympathetic activity in the subject; and adjusting the electrical stimulation based upon assessing the at least one of sympathetic and parasympathetic activity. Adjusting the electrical stimulation can include identifying abnormal sympathetic or parasympathetic activity in the patient, and adjusting the frequency of stimulation of the first nerve, and/or discontinuing electrical stimulation of the first nerve; and initiating electrical stimulation of a second nerve.

Some embodiments involve a method for treating at least one of cardiac arrhythmias and hypertension using combination pharmacotherapy and transcutaneous electrical stimulation, that include any number of the following: administering an amount of a cardiac glycoside to a patient; positioning a first peripheral nerve effector on a patient's skin on an extremity of the patient; and delivering a first electrical nerve stimulation signal transcutaneously to the first peripheral nerve effector to stimulate a first peripheral nerve sufficient to modify at least one brain or spinal cord autonomic feedback loop relating to the cardiac arrhythmia or hypertension. The cardiac glycoside can be digoxin.

Also disclosed herein is a combination pharmacotherapy and electrical stimulation system for treating cardiac arrhythmias or hypertension, that can include, for example, any number of features as disclosed in the specification. The system can include, for example, a wearable device that includes a controller; a first peripheral nerve effector configured to be positioned on a patient's skin on an extremity of the patient; and at least one biomedical sensor or data input source configured to provide feedback information. The controller can be configured to generate a first electrical nerve stimulation signal transcutaneously to the first peripheral nerve effector to stimulate a first peripheral nerve sufficient to modify at least one brain or spinal cord autonomic feedback loop relating to the cardiac arrhythmia or hypertension. The system can also include a cardiac glycoside for administration to the patient, such as digoxin, in a dose such as about or less than about 62.5 mcg, 31.25 mcg, 16 mcg, 8 mcg, or less.

In several embodiments, the embodiments described herein that selectively target one or more fiber types of a peripheral nerve and/or that coordinate stimulation of multiple peripheral nerves such that the action potentials reach the same target location (e.g., in the brachial plexus) at the same time or substantially the same time can have one or more of the following advantages: greater therapeutic benefit with less discomfort; less current use (e.g., less power and improved battery life); increased likelihood of patient compliance due to the foregoing. In several embodiments, the embodiments described herein that include multiple peripheral nerve stimulation to promote sympathovagal balance with at least one peripheral nerve modulating the sympathetic nervous system and at least one peripheral nerve modulating the parasympathetic nervous system can advantageously have the ability to selectively modulate either sympathetic and/or parasympathetic arms of the autonomic nervous system in response to detected sympathetic and/or parasympathetic overactivity. In several embodiments, peripheral nerve stimulation can advantageously have synergistic effects when combined with pharmacotherapy, including cardiac glycosides such as digoxin. The effects can include enhanced response to therapy, a lesser dose of cardiac glycoside needed to achieve the effects and thus lower adverse reactions, and the like.

BRIEF DESCRIPTION OF THE DRAWINGS

Non-limiting novel features of the invention are set forth with particularity in the claims that follow. A better understanding of the features and advantages of some embodiments of the present invention will be obtained by reference to the following detailed description that sets forth illustrative embodiments, in which the principles of the invention are utilized, and the accompanying drawings of which:

FIGS. 1A-1E illustrate various views of an embodiment of a device and system that provides peripheral nerve stimulation, targeting individual nerves, to reduce cardiac dyssynchrony and/or blood pressure.

Figure 2C:
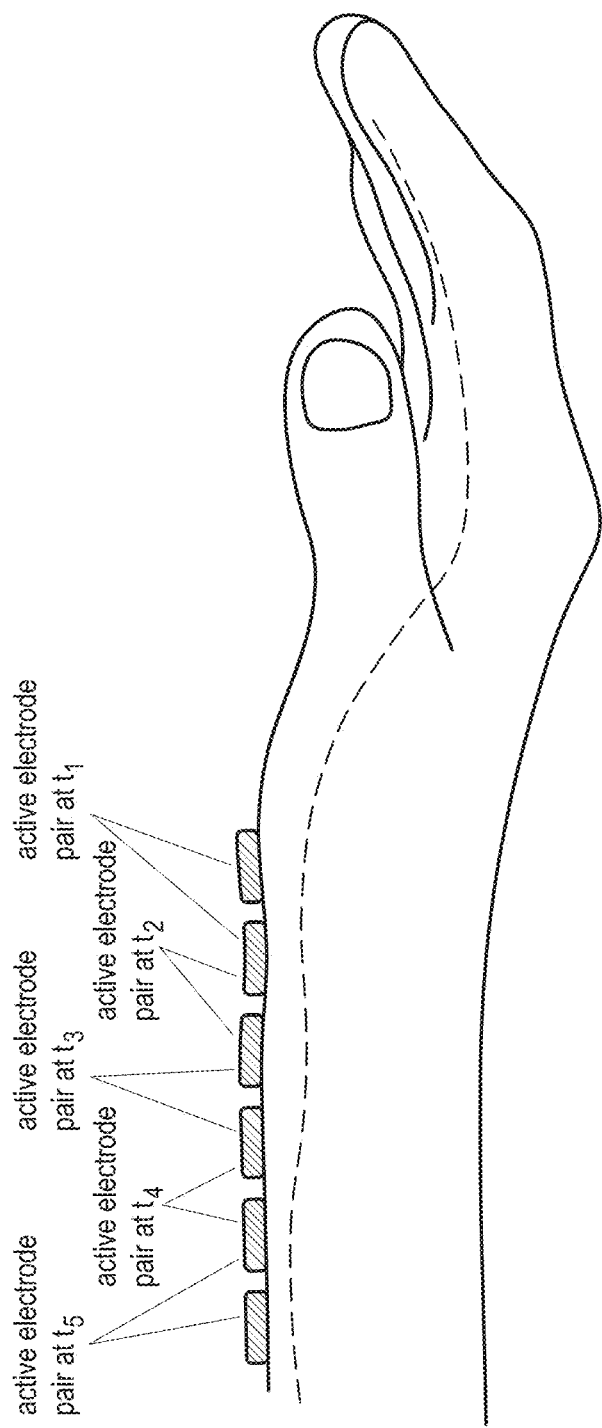
FIG. 2C illustrates an embodiment of a system that can be configured to stimulate multiple dermatomes similarly in a timed manner.
Figure 2D:
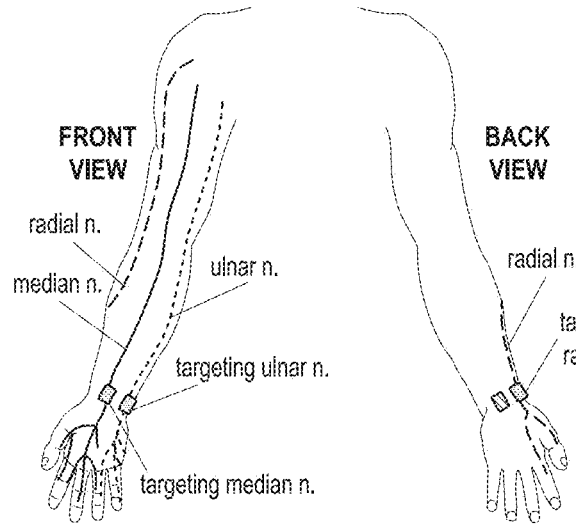
FIGS. 2A and 2B illustrate an embodiment of peripheral nerve stimulation, where the median nerve is stimulated by electrodes placed longitudinally along the nerve (FIG. 2B) versus excitation by an array of electrodes circumferentially distributed around the wrist (FIG. 2A).
Figure 2E:
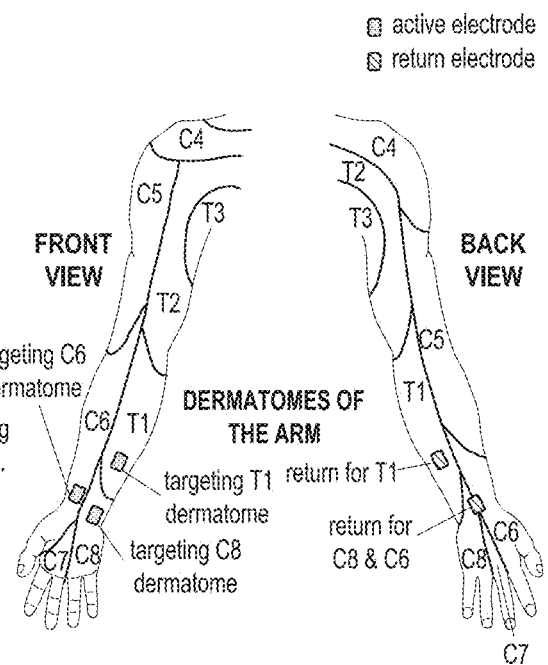
Figure 2F:
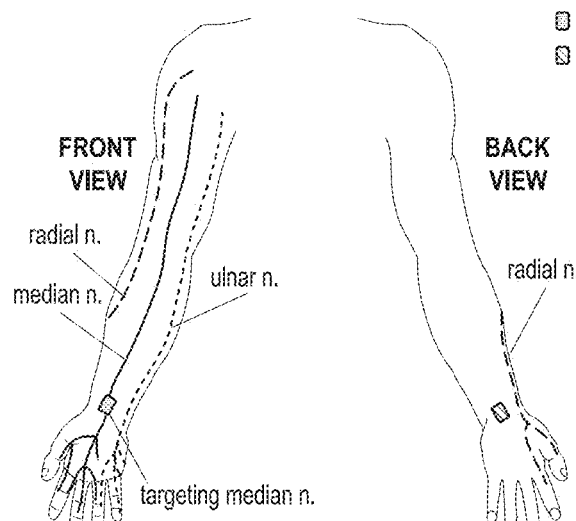
Figure 2G:
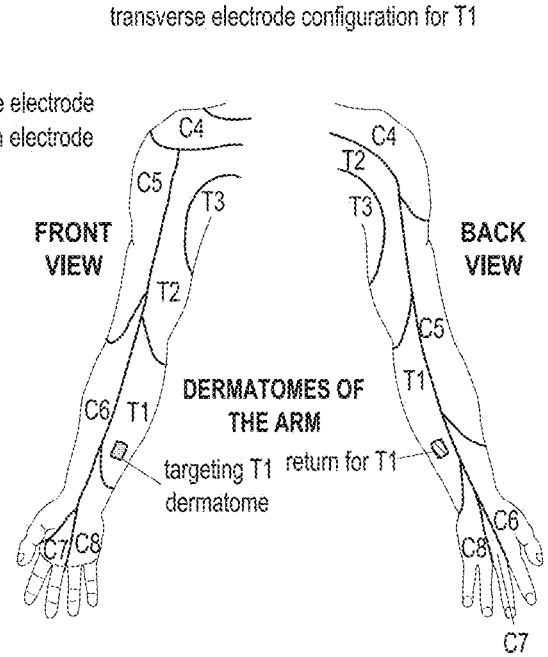
Figure 2H:
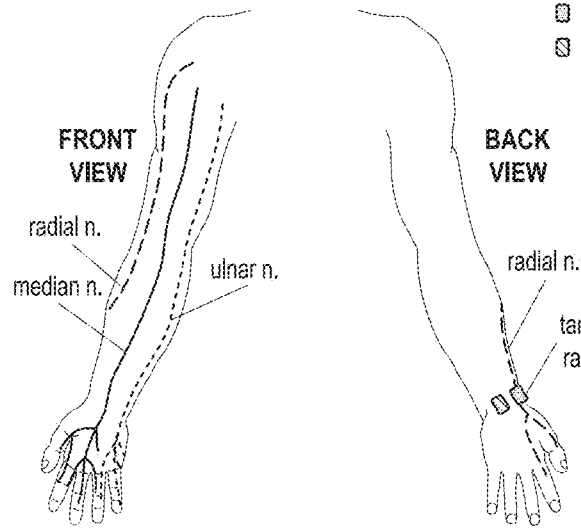
Figure 2I:
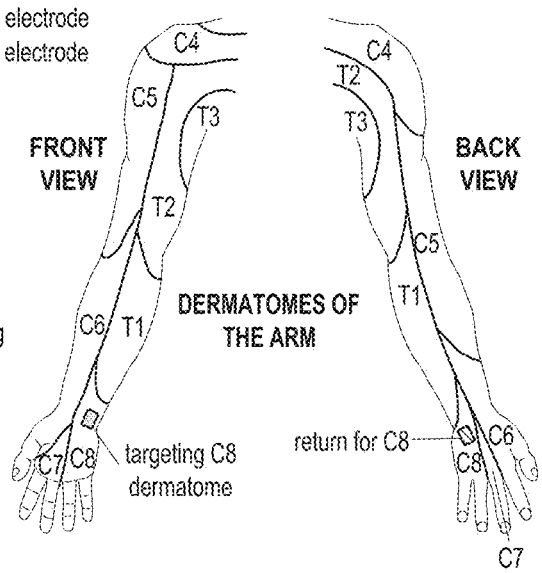
Figure 2J:
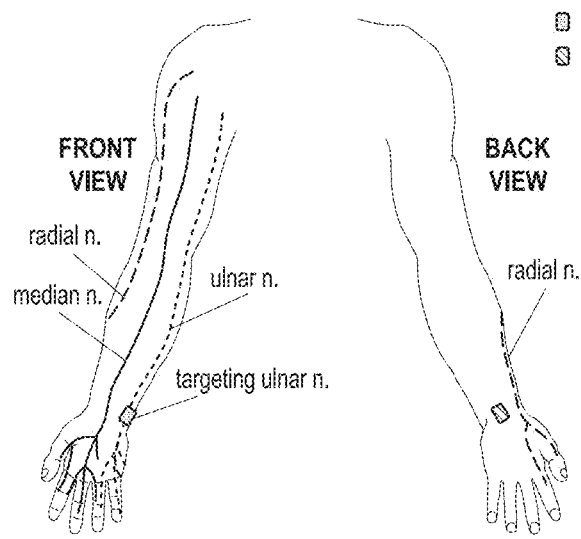
Figure 2K:
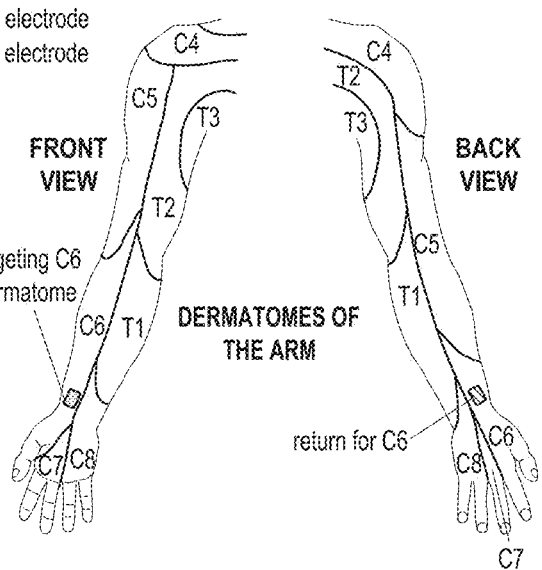
Figure 2L:
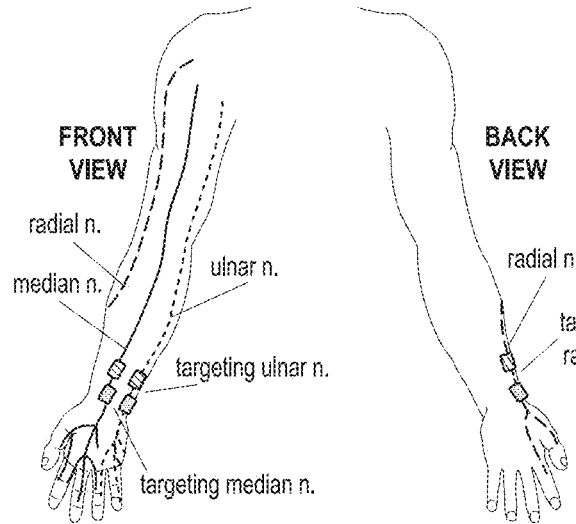
Figure 2M:
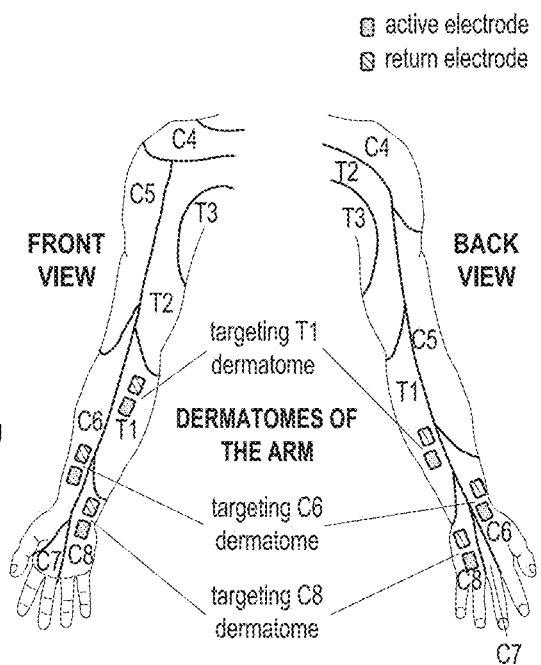
Figure 2N:
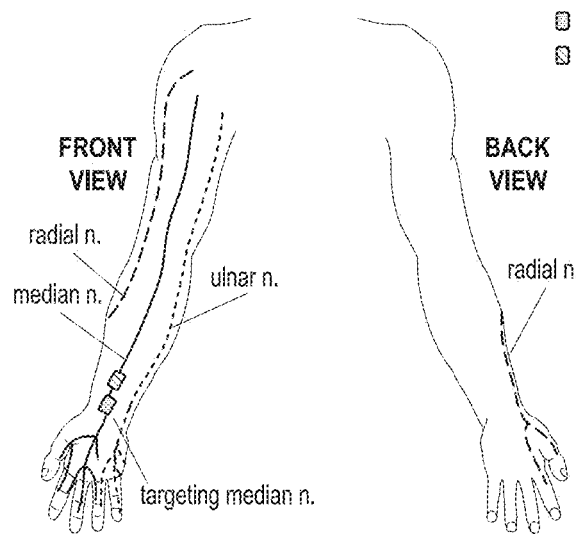
Figure 2O:
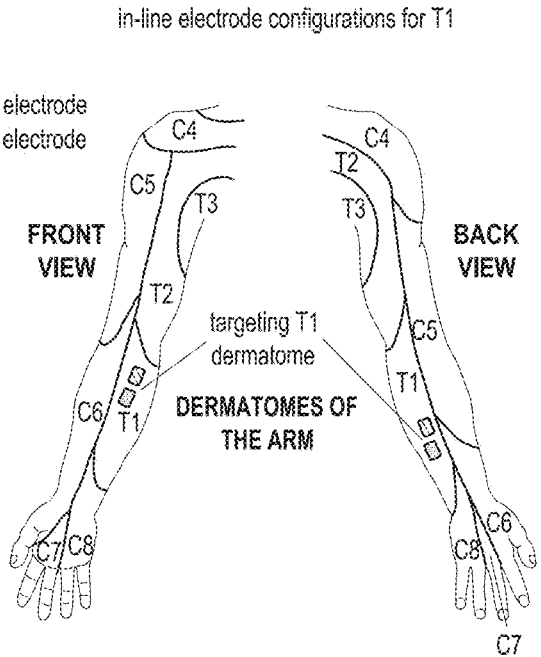
Figures 2P, 2Q:
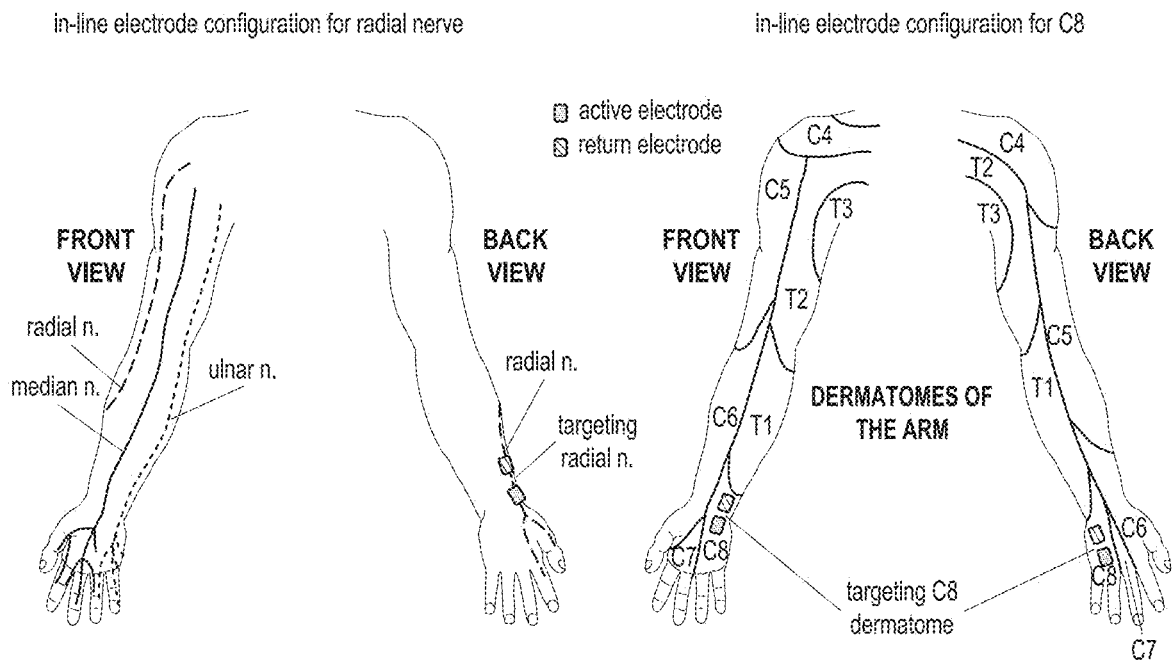
Figures 2R, 2S:
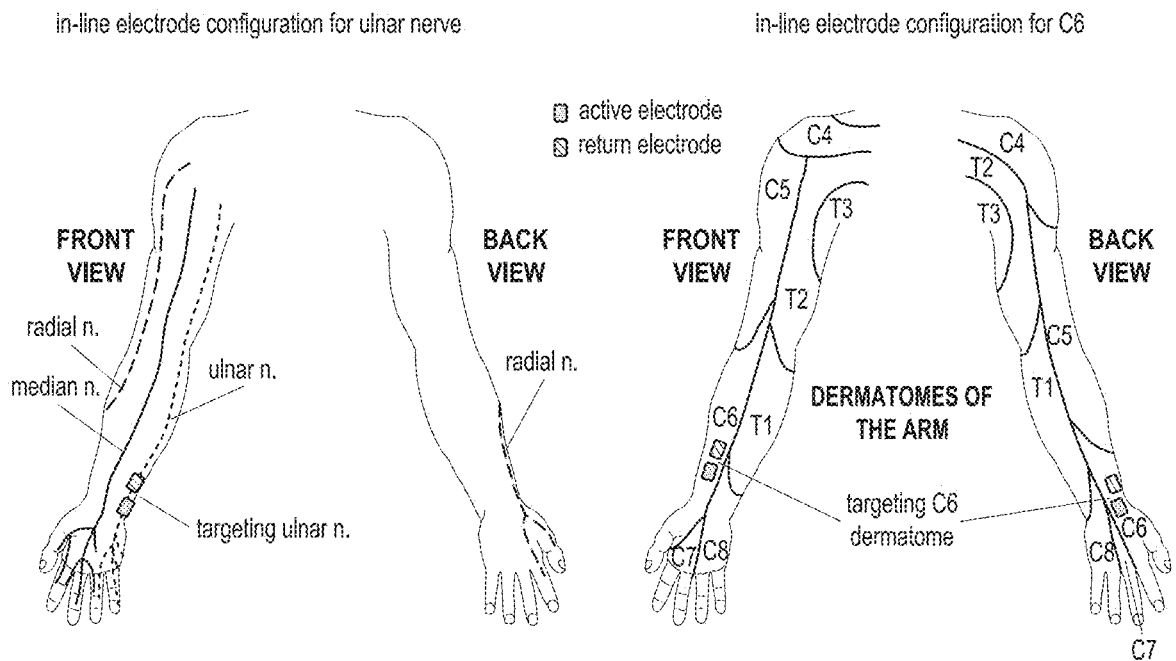

The illustrations of FIGS. 2D-2S depict various options for targeting various nerves and/or dermatomes of the upper extremities.

Figure 2T:
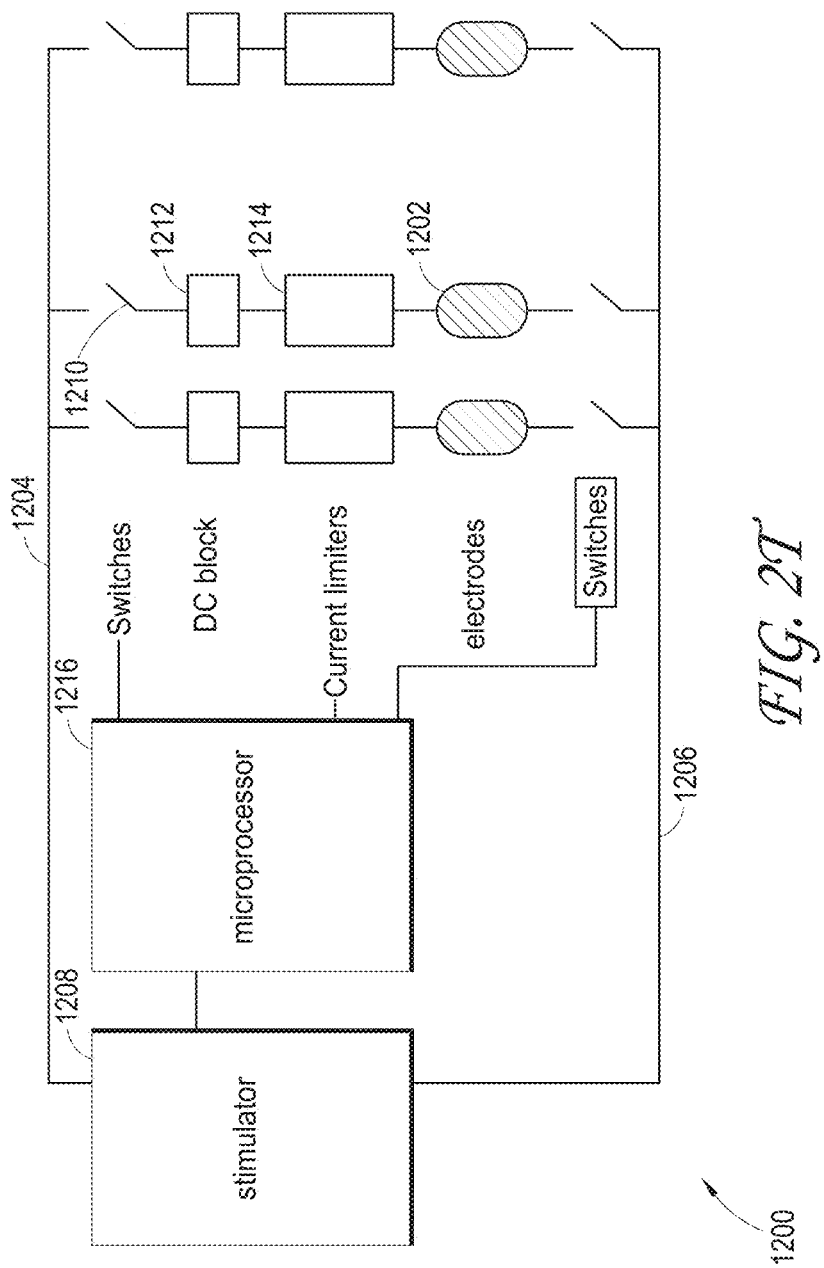

FIG. 2T illustrates a block diagram of a stimulator with a microprocessor and switches, according to some embodiments of the invention.

Figure 2U:
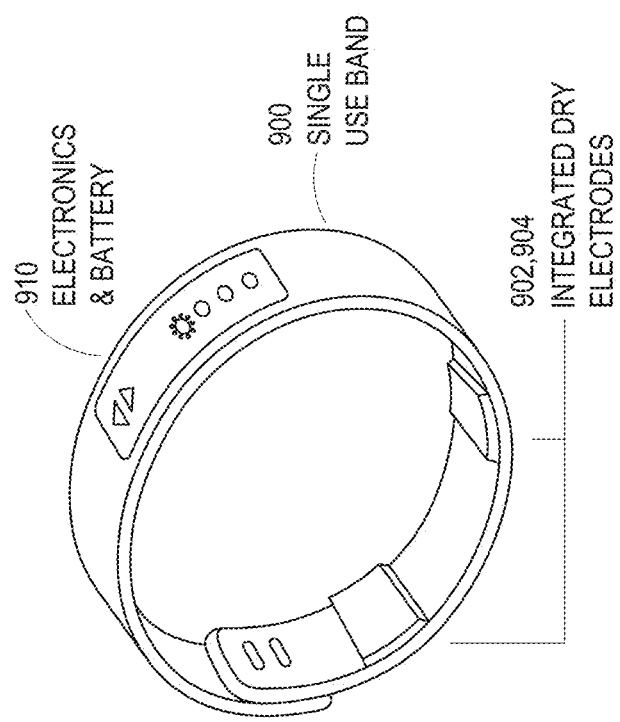

FIG. 2U illustrates an embodiment of a stimulator with electrodes that can be disposed on a wearable band, according to some embodiments of the invention.

Figure 2V:
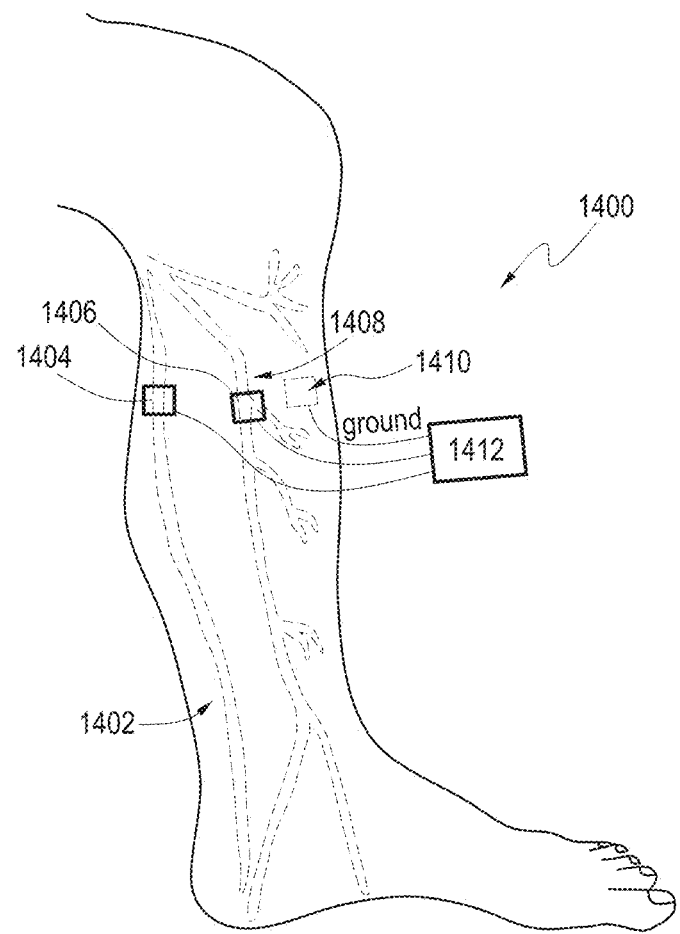

FIG. 2V illustrate a system and method of peripheral nerve stimulation can be provided that targets one, two, or more individual nerves.

Figure 3A:
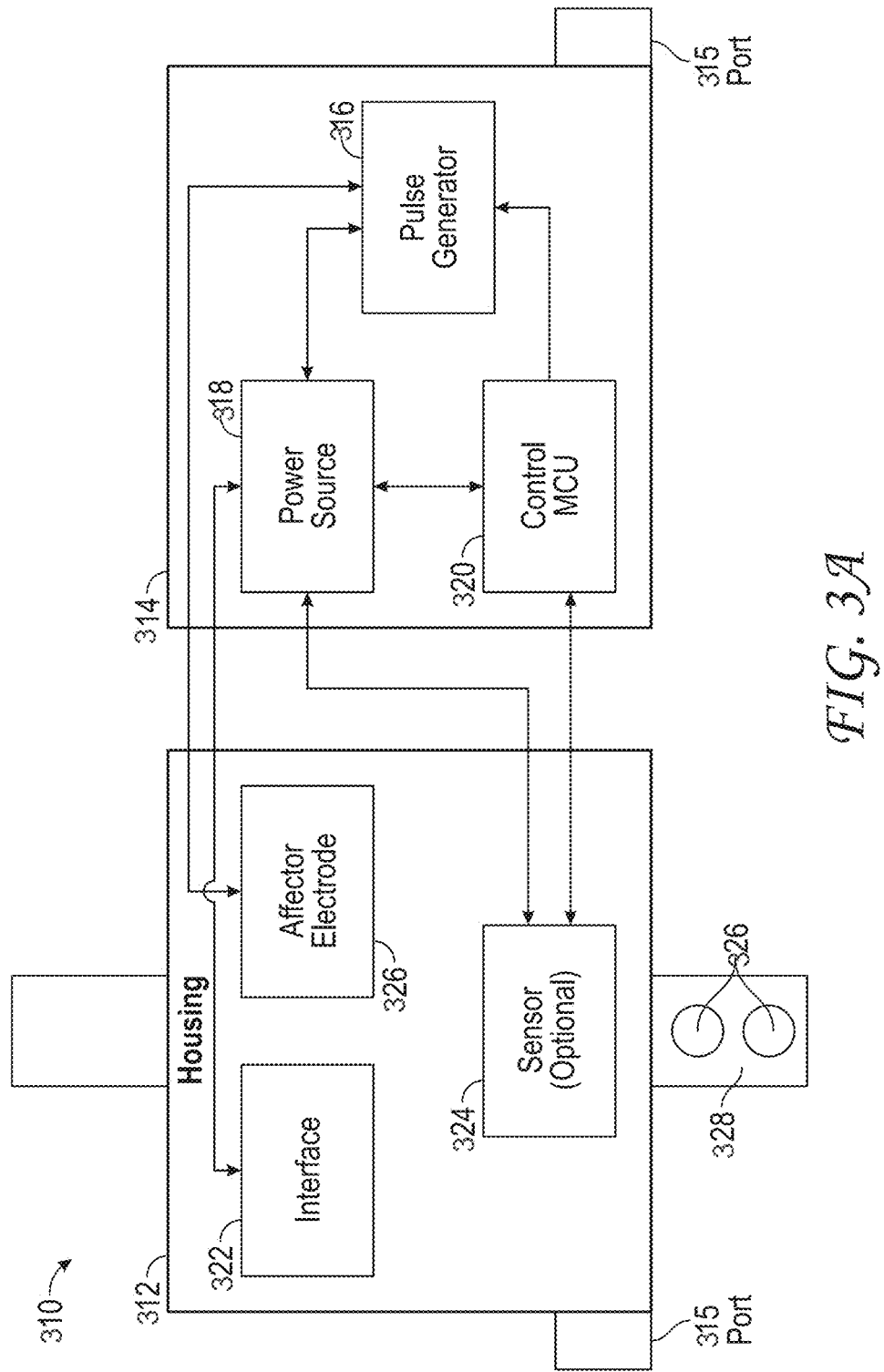
Figure 3B:
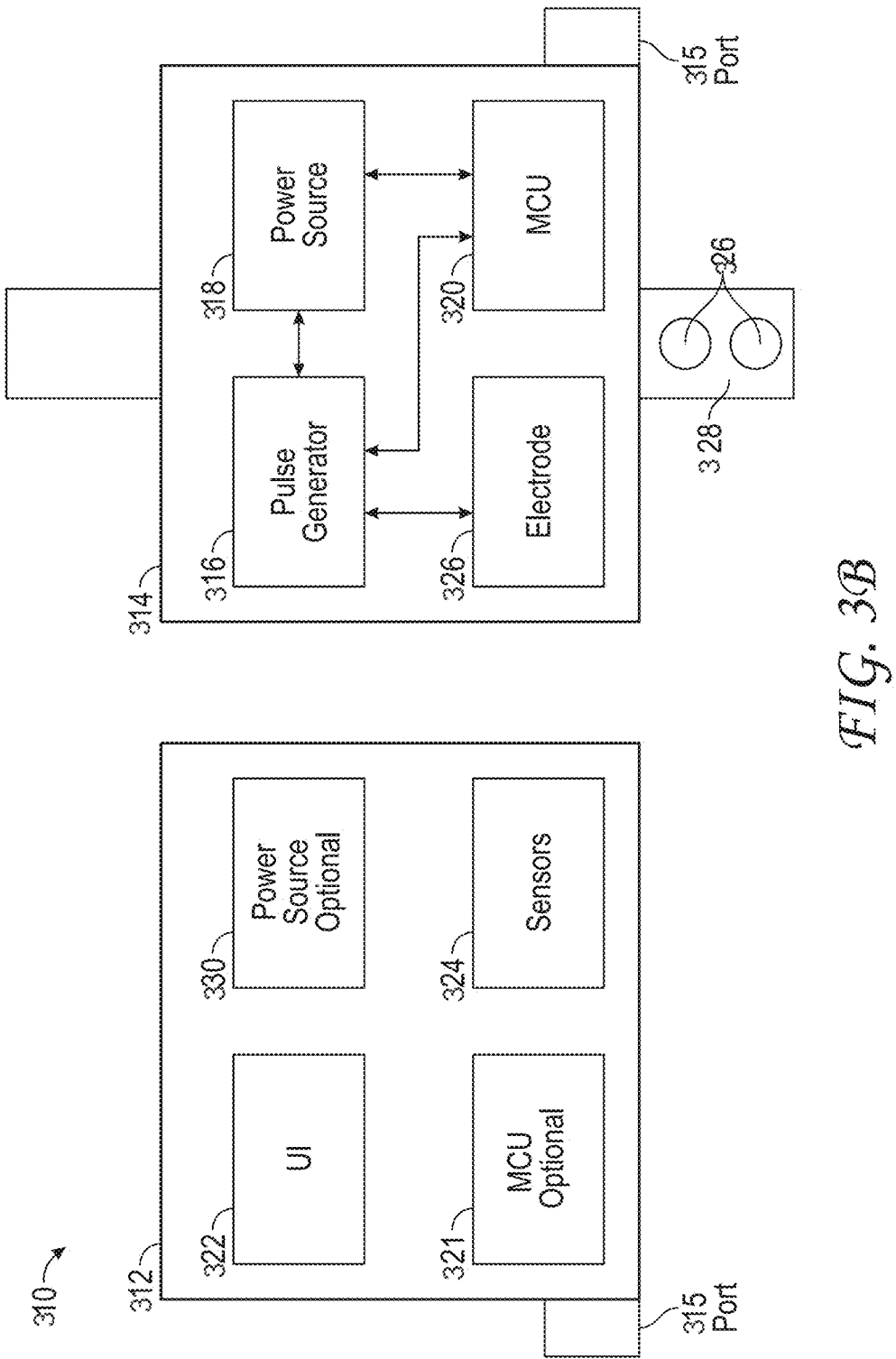

FIGS. 3A and 3B illustrate various embodiments of a monitoring unit and
a therapy unit that form a two part treatment system.

Figure 3C:
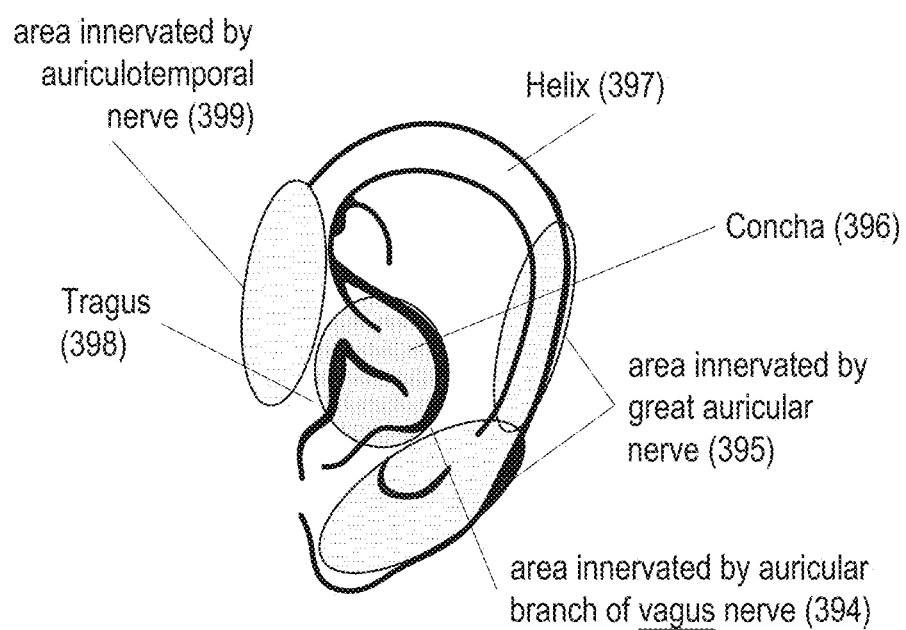

FIG. 3C schematically illustrates selected anatomy relating to the tragus.

Figure 3D:
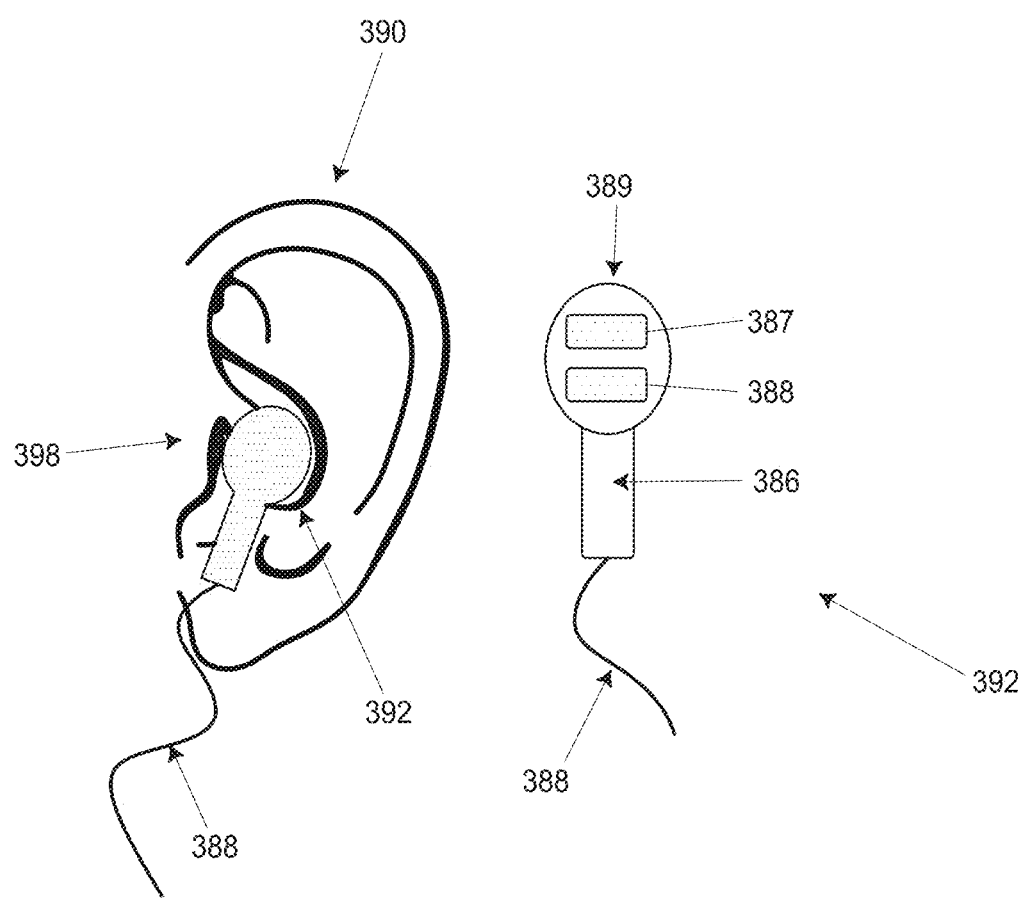

FIG. 3D illustrates an embodiment of a tragus stimulation device.

FIGS. 4A-4D illustrate an embodiment of a two part system with a single monitoring unit and a plurality of therapy units.

FIGS. 5A-5I illustrate another embodiment of a wearable therapy system.

Figure 6:
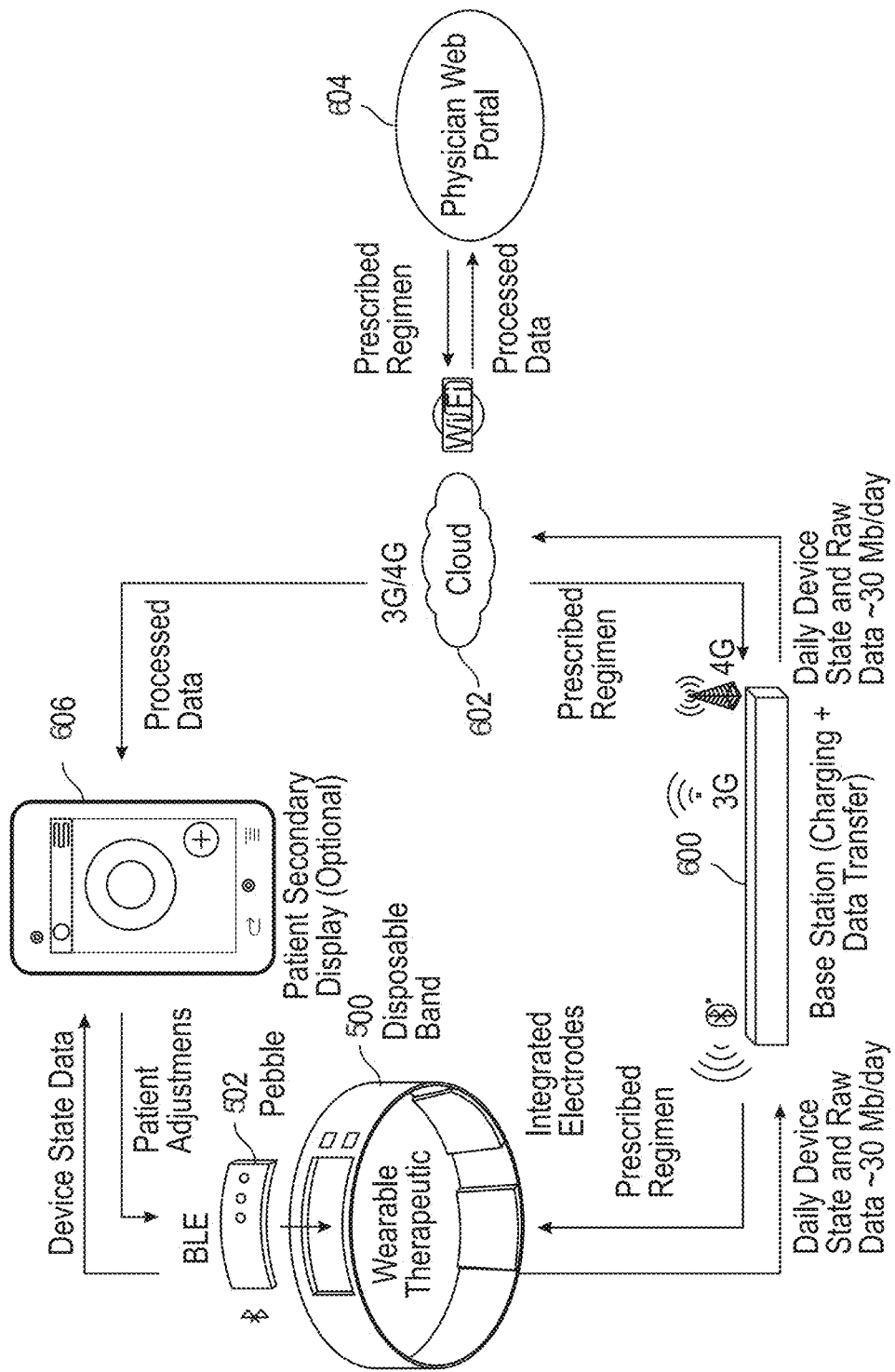

FIG. 6 illustrates an embodiment of the wearable therapy system that uses the cloud to receive and transmit data between the therapy system and a physician.

Figure 7:
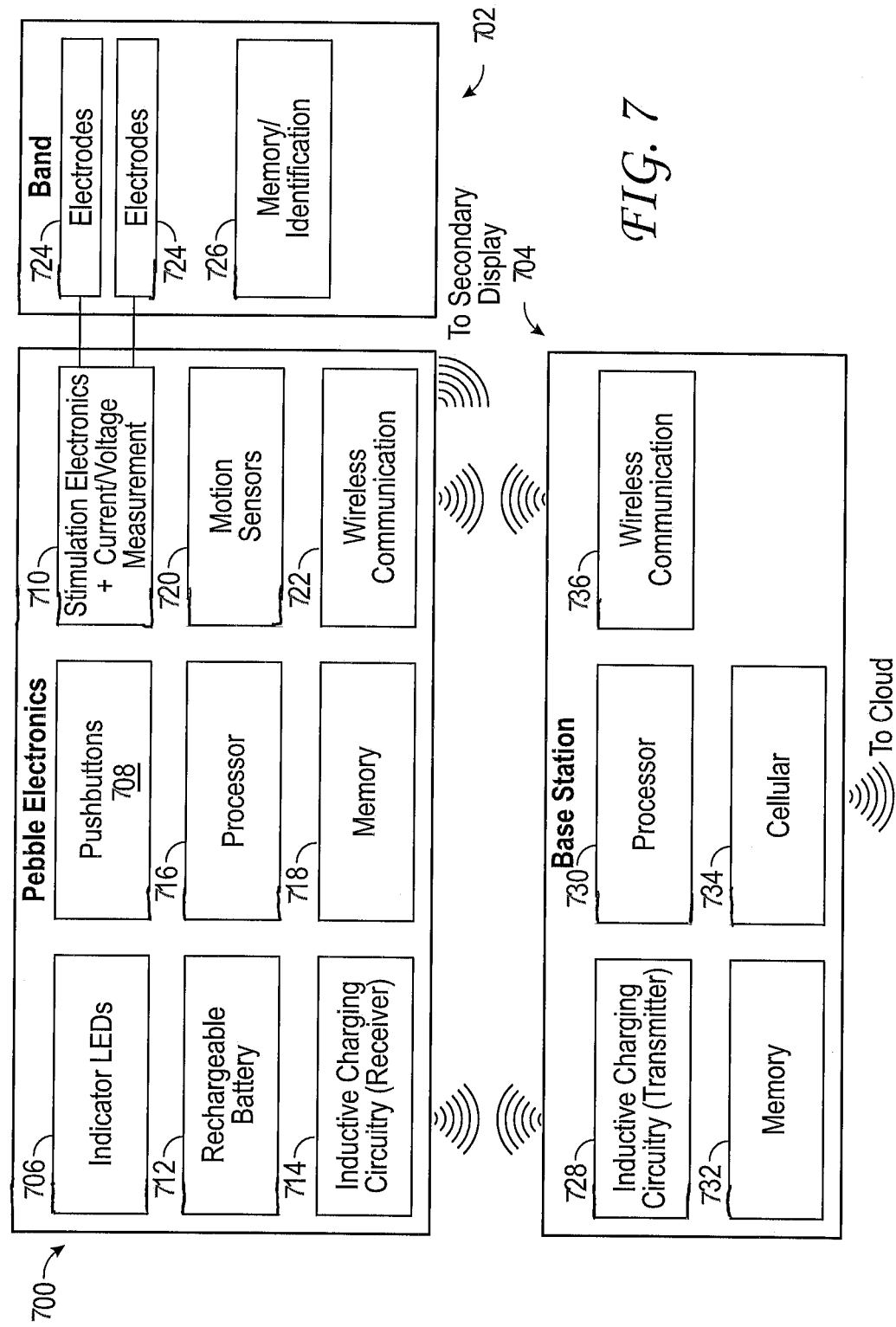

FIG. 7 is a block diagram that illustrates the individual components of the therapy unit, band, and base station shown in FIG. 6.

Figure 8:
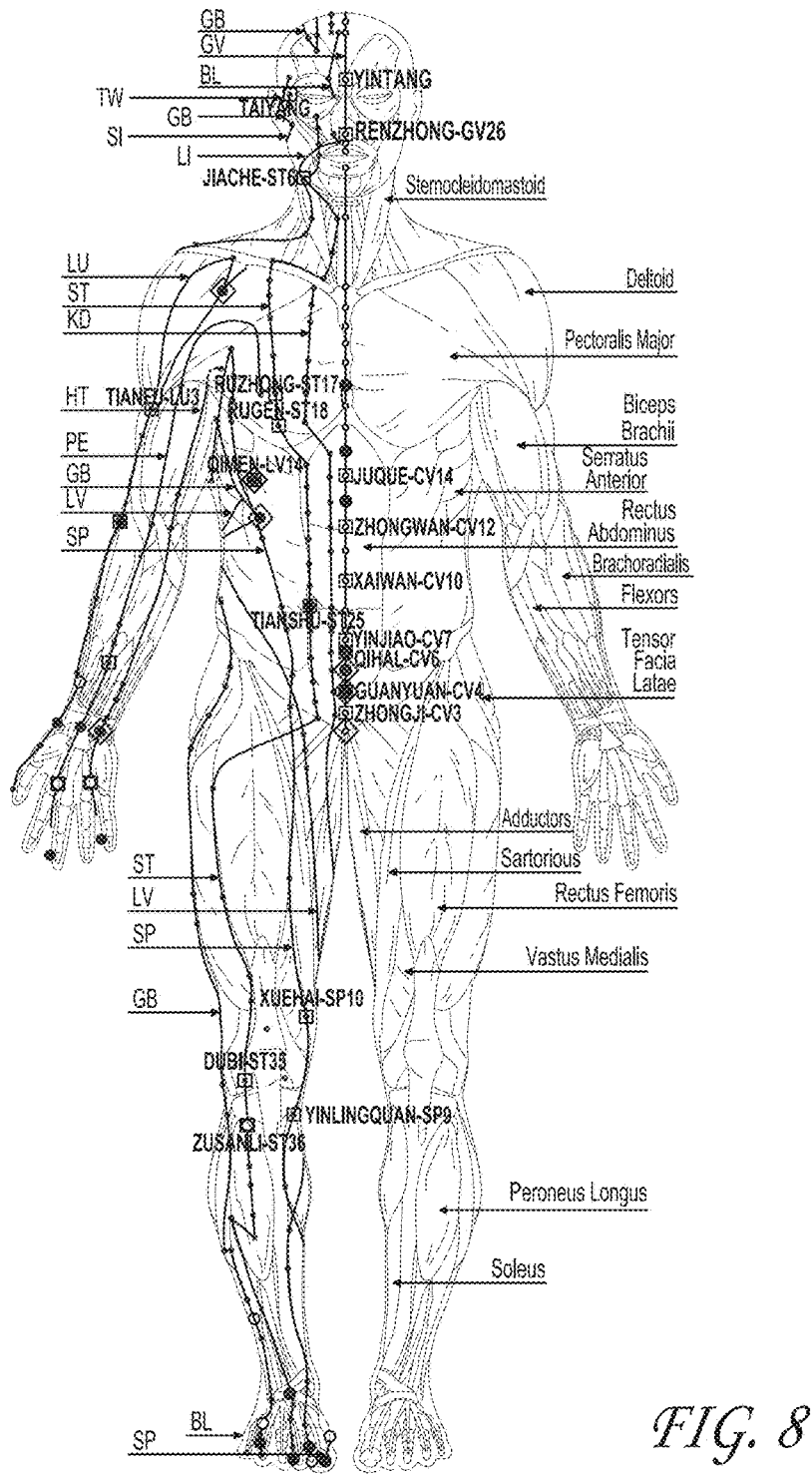
Figure 9:
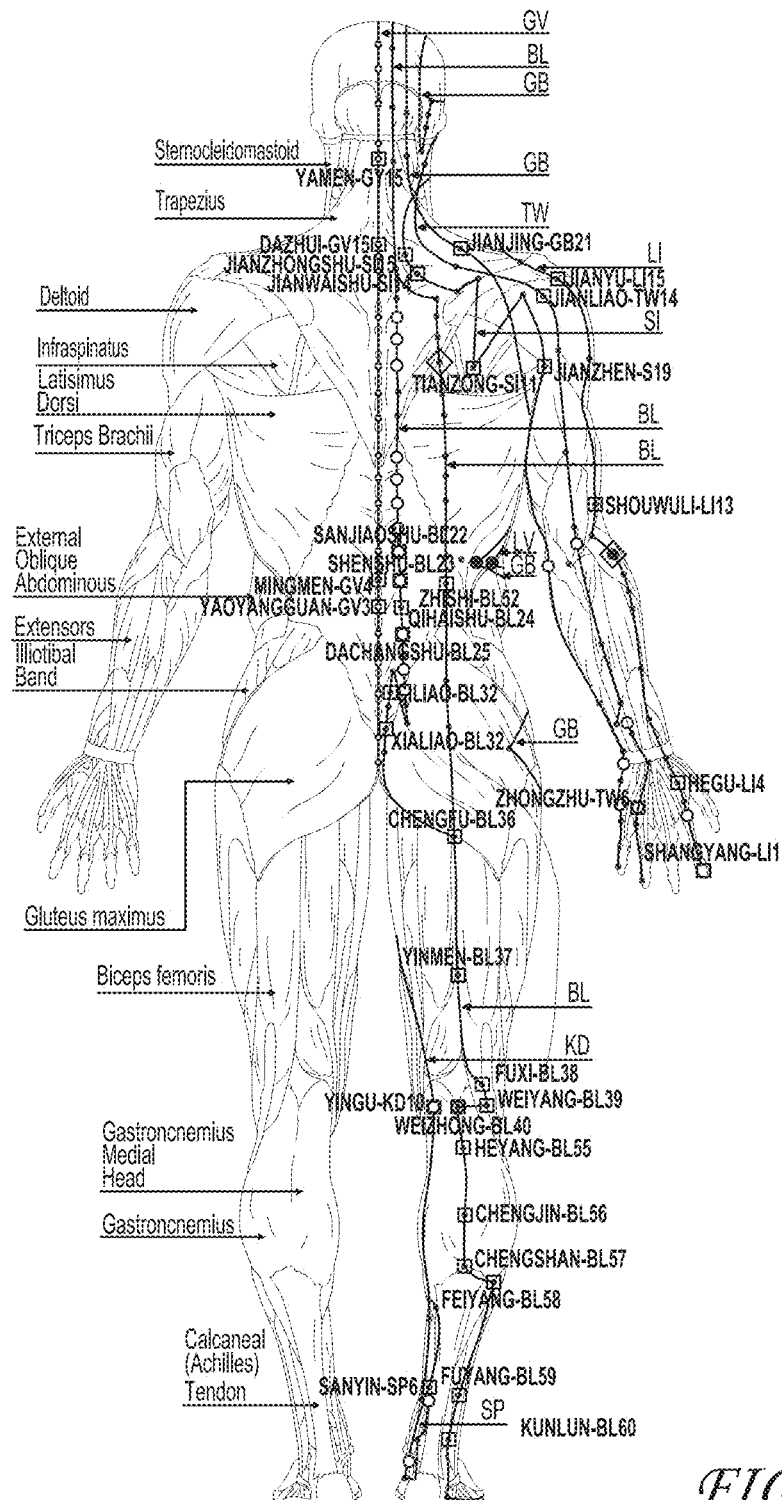

FIGS. 8 and 9 illustrate human body meridian points that can be used as locations for stimulation.

Figure 9A:
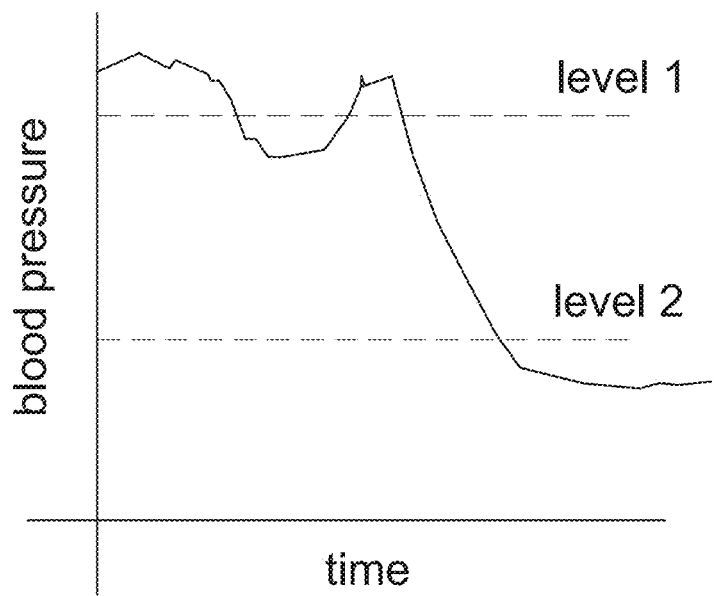

FIG. 9A illustrates a blood pressure profile of a patient along with various blood pressure thresholds that can be used to modulate stimulation.

FIGS. 10A-10D illustrate various locations on the wrist and arm where the stimulator and sensors can be worn.

Figure 11:
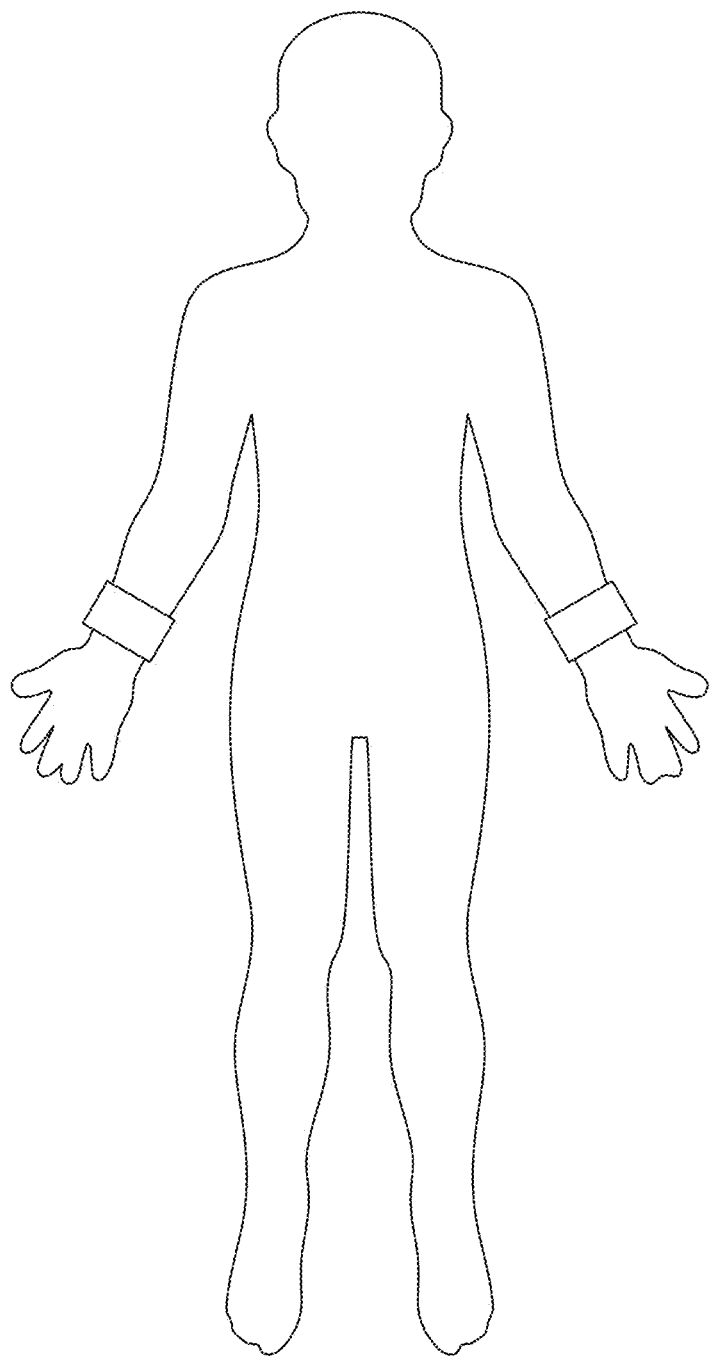

FIG. 11 illustrates an embodiment of bilateral stimulation of nerves in both arms.

Figure 12:
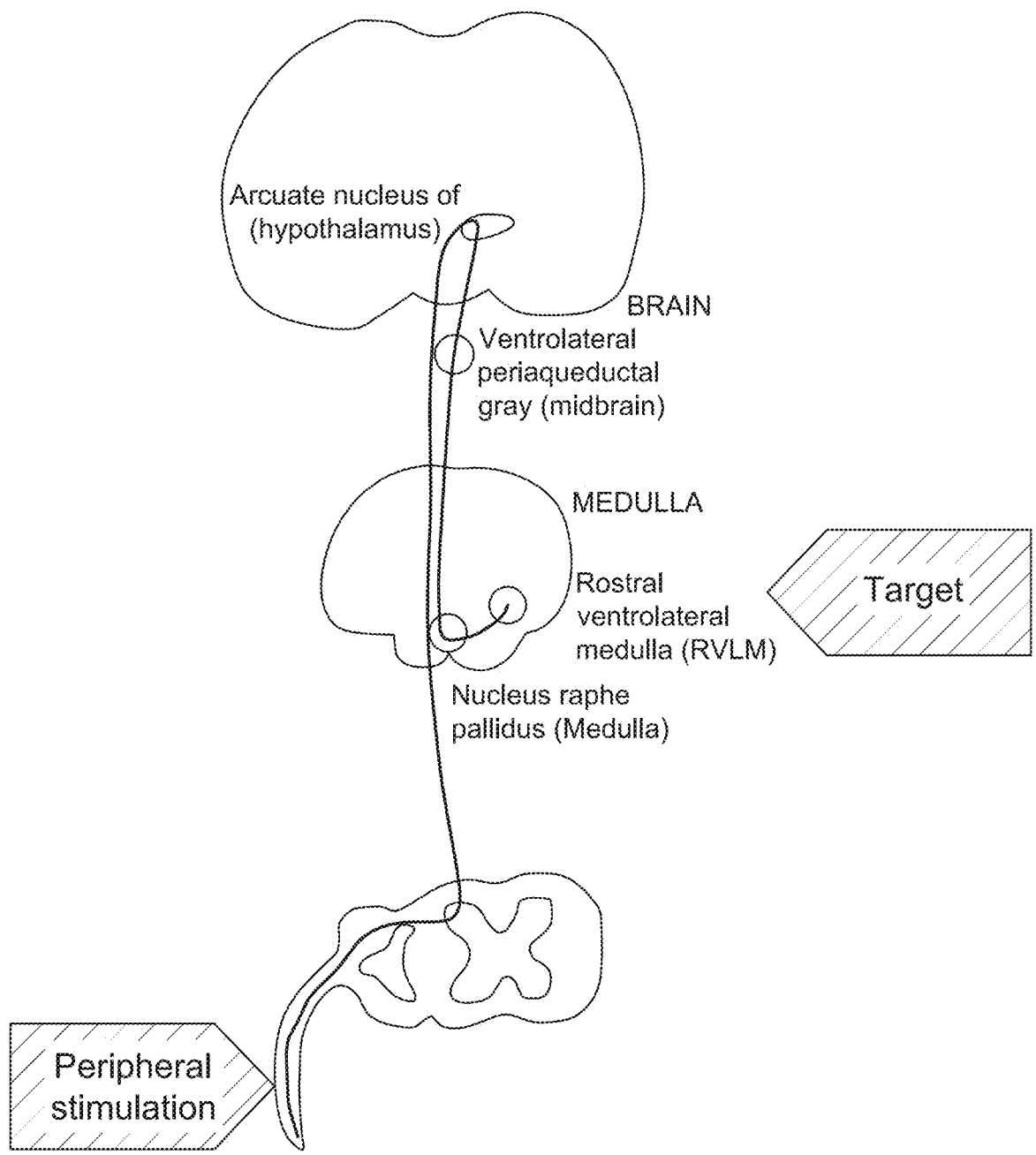

FIG. 12 illustrates a neural circuit where afferent nerves in the periphery, including but not limited to the median nerve, innervate the arcuate nucleus of the hypothalamus. Not to be limited by theory, modulation of the arcuate nucleus can reduce elevated sympathetic outflow via descending input via the ventrolateral peri-acqueductal grey in the midbrain and the nucleus raphe pallidus in the medulla to the rostral ventrolateral medulla (RVLM).

Figure 12A:
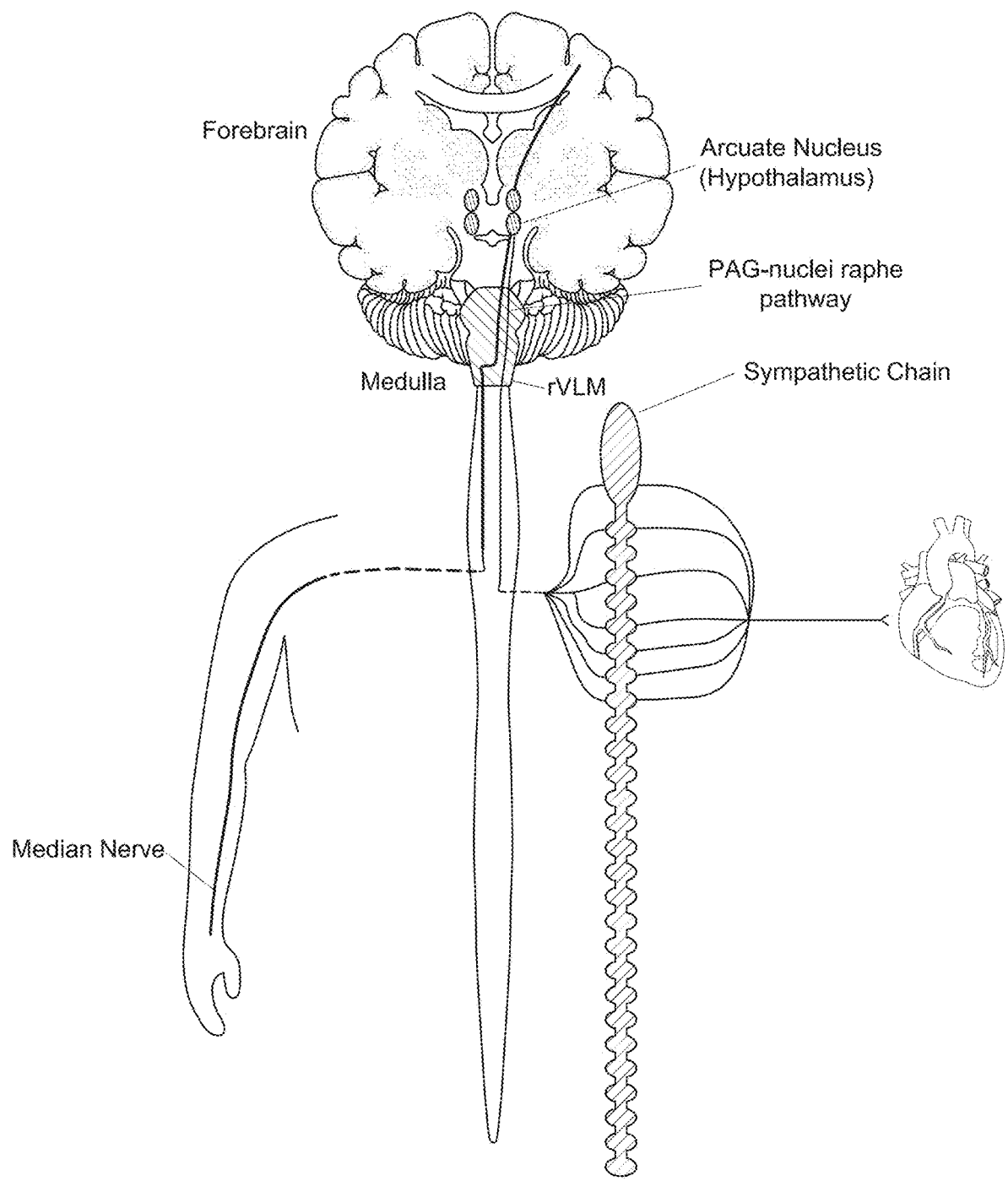

FIG. 12A schematically illustrates a neural pathway associated with the median nerve.

Figure 12B:
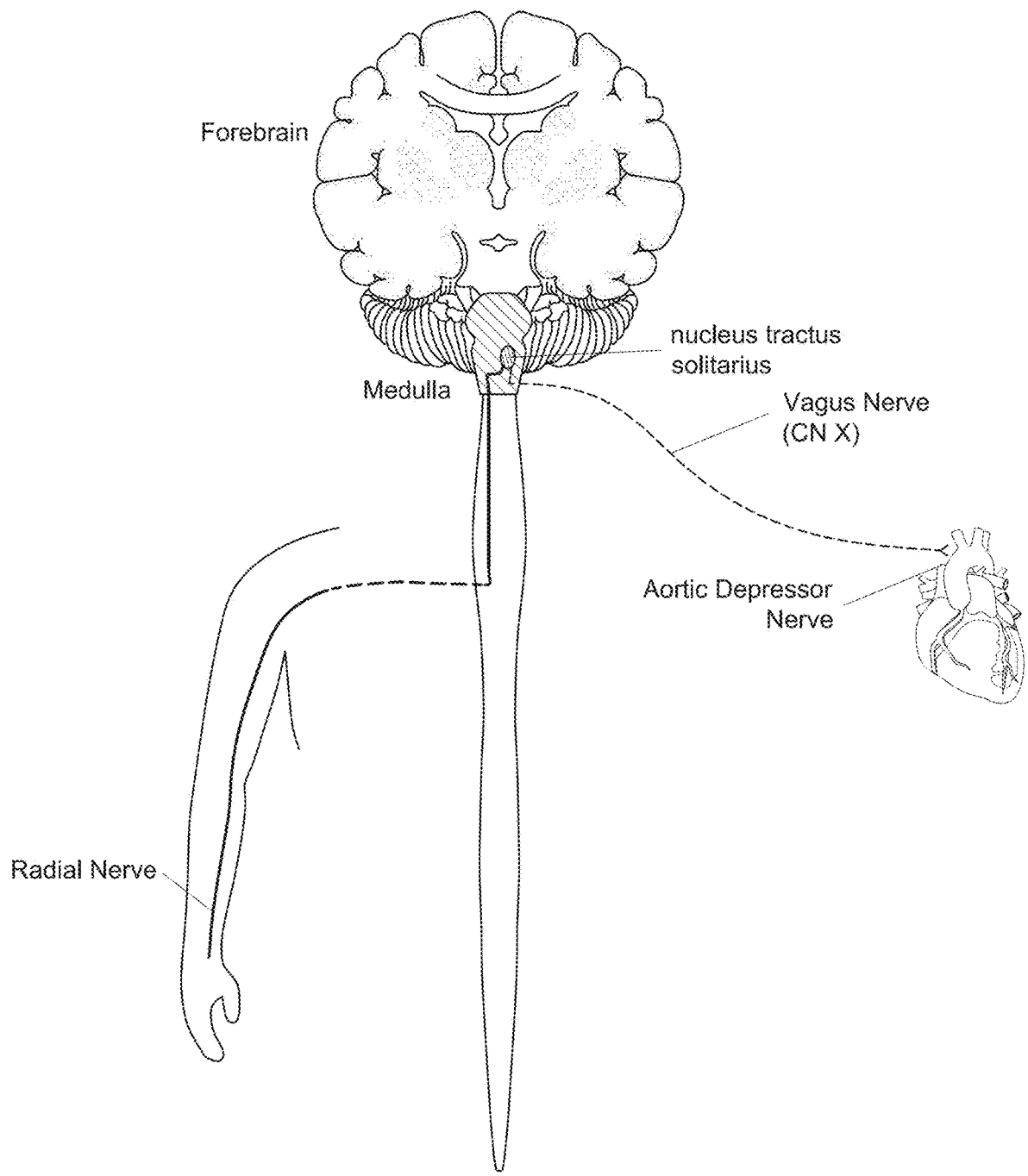

FIG. 12B schematically illustrates a neural pathway associated with the radial nerve.

Figure 13A:
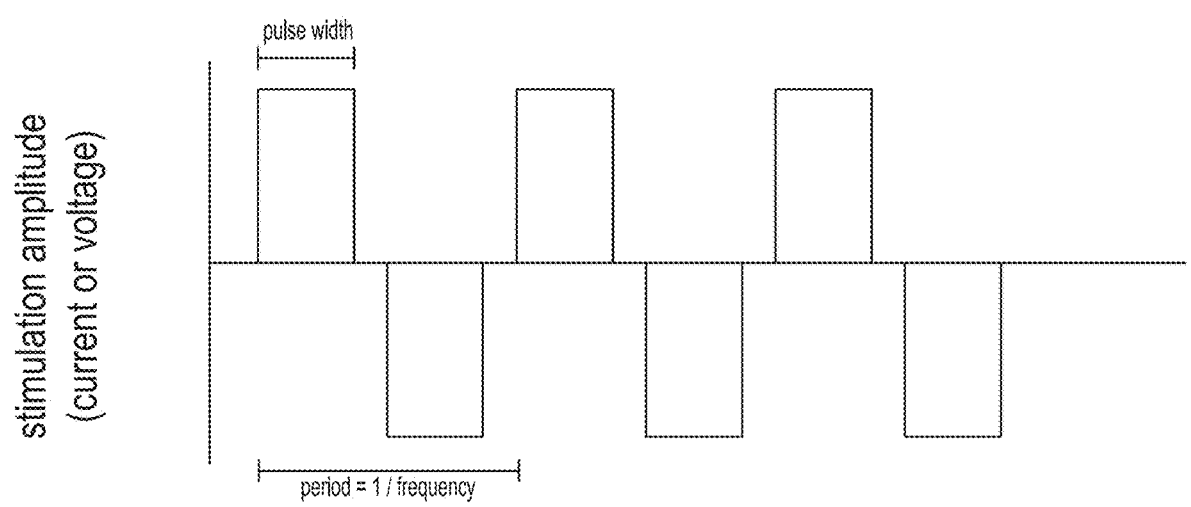
Figure 13B:
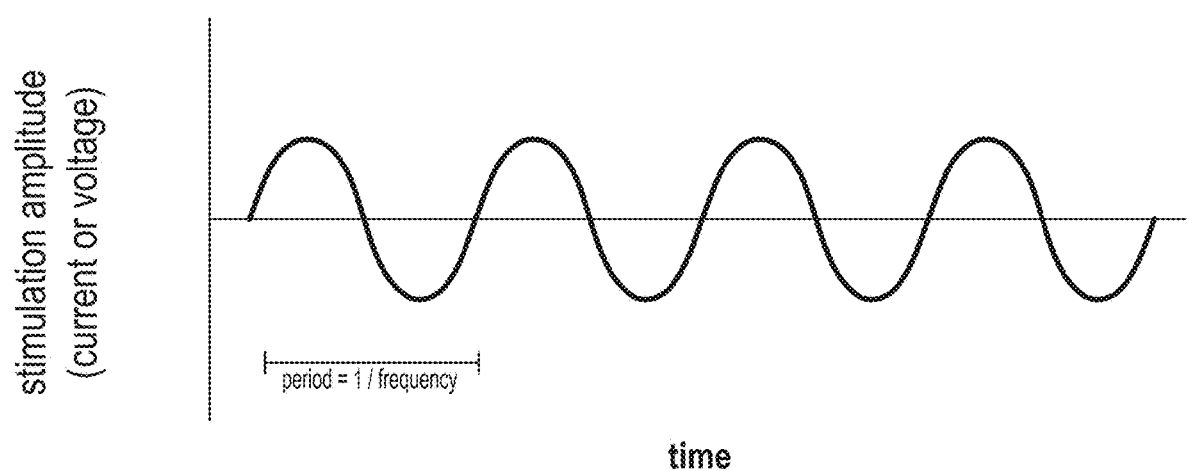

FIGS. 13A and 13B illustrate embodiments of stimulation patterns for selective activation of nerve fibers.

Figure 13C:
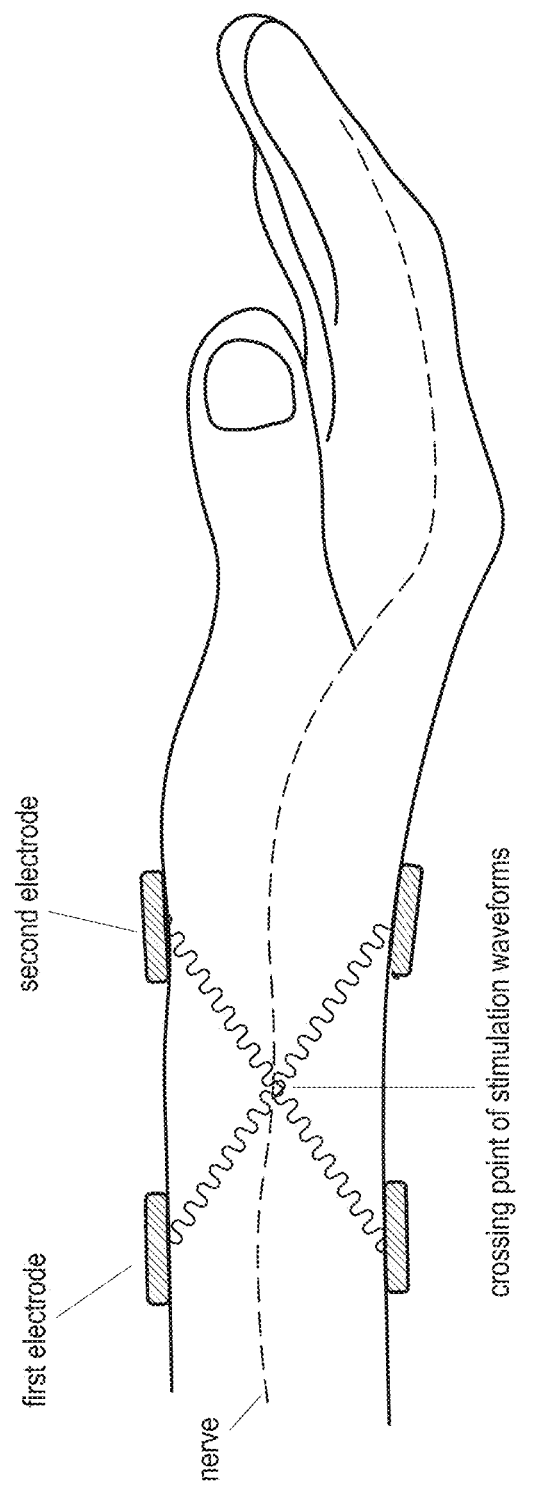
Figure 13D:
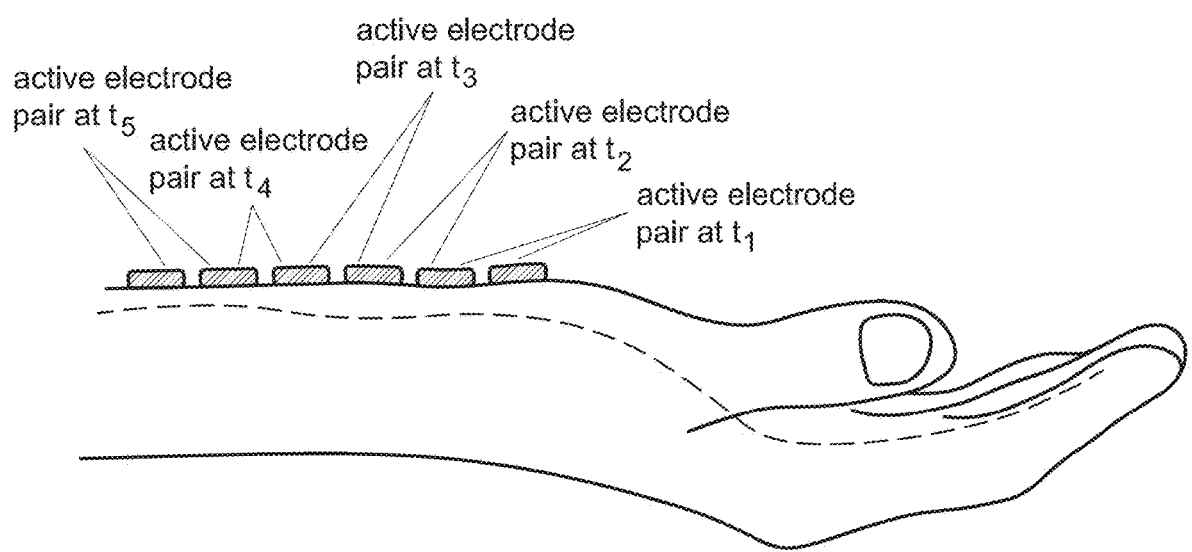

FIGS. 13C and 13D illustrate embodiments of electrode alignments for selective activation of nerve fibers.

Figure 14A:
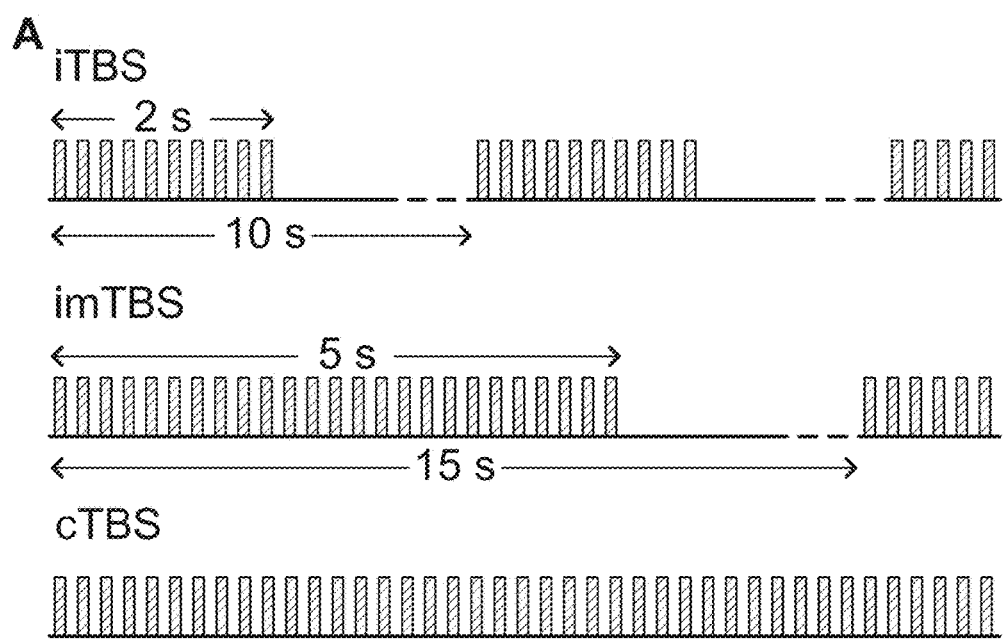
Figure 14B:
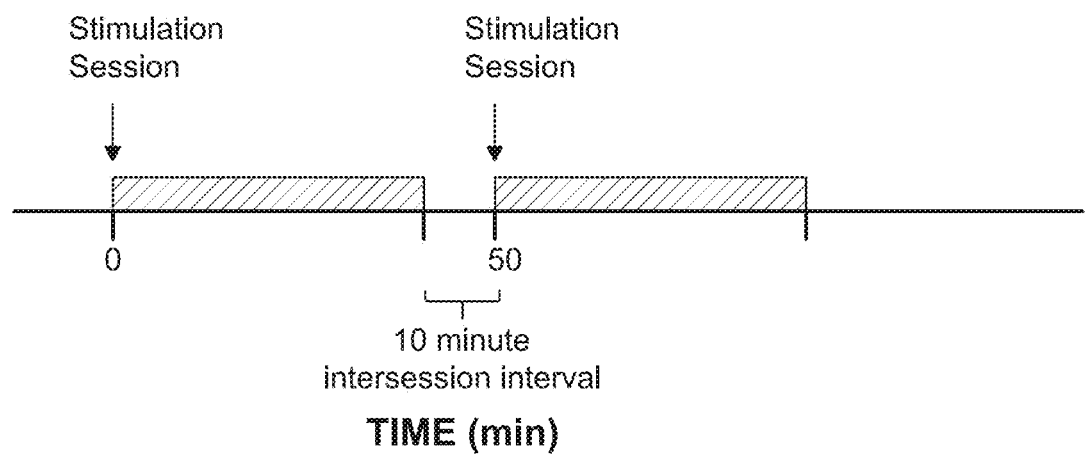
Figure 14C:
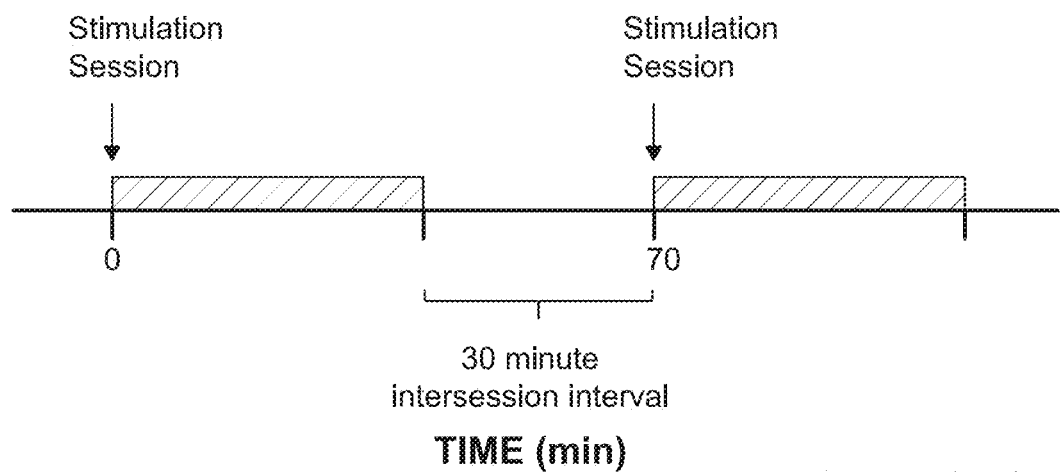

FIGS. 14A-14C illustrate bursting patterns, according to some embodiments of the invention.

Figure 14D:
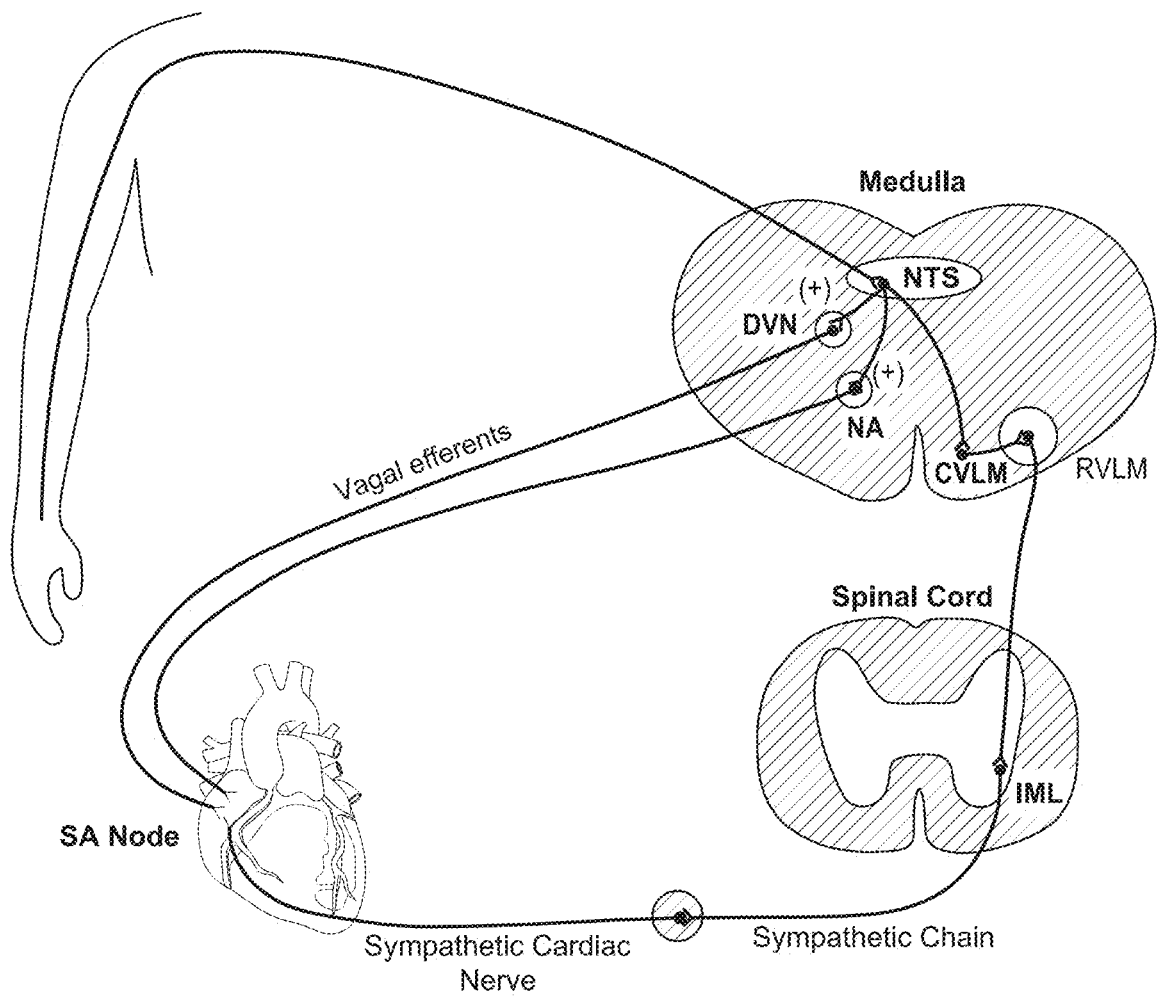

FIG. 14D schematically illustrates an autonomic reflex loop.

Figure 14E:
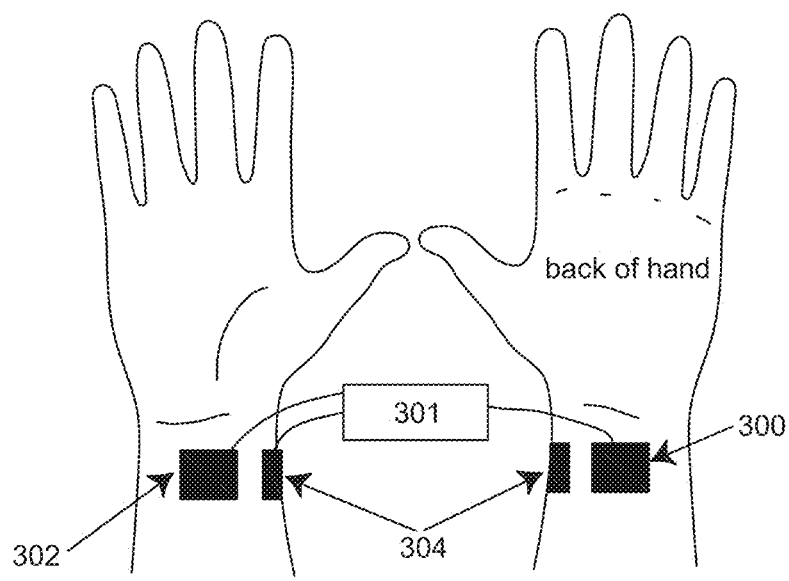
Figures 14F, 14G:
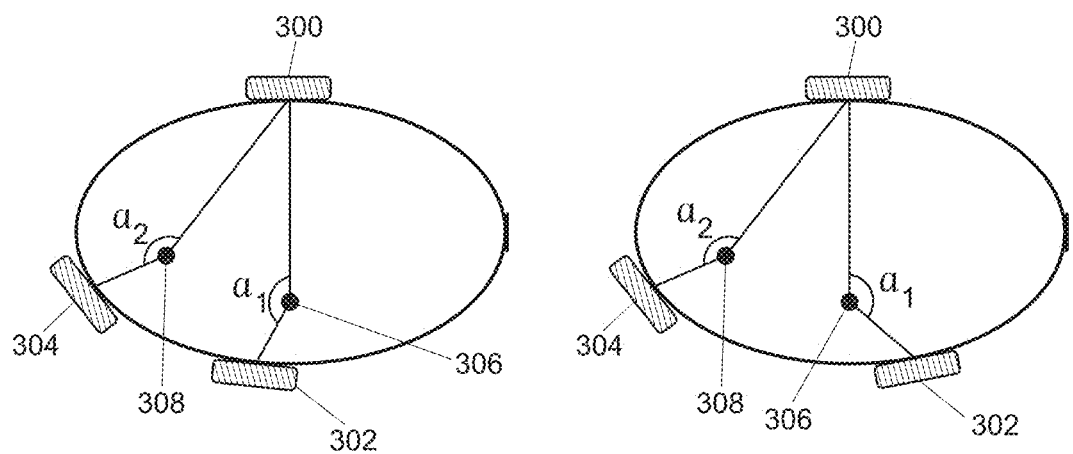

FIGS. 14E-14G illustrate embodiments of electrode configurations for stimulating peripheral nerves, according to some embodiments of the invention.

Figure 15:
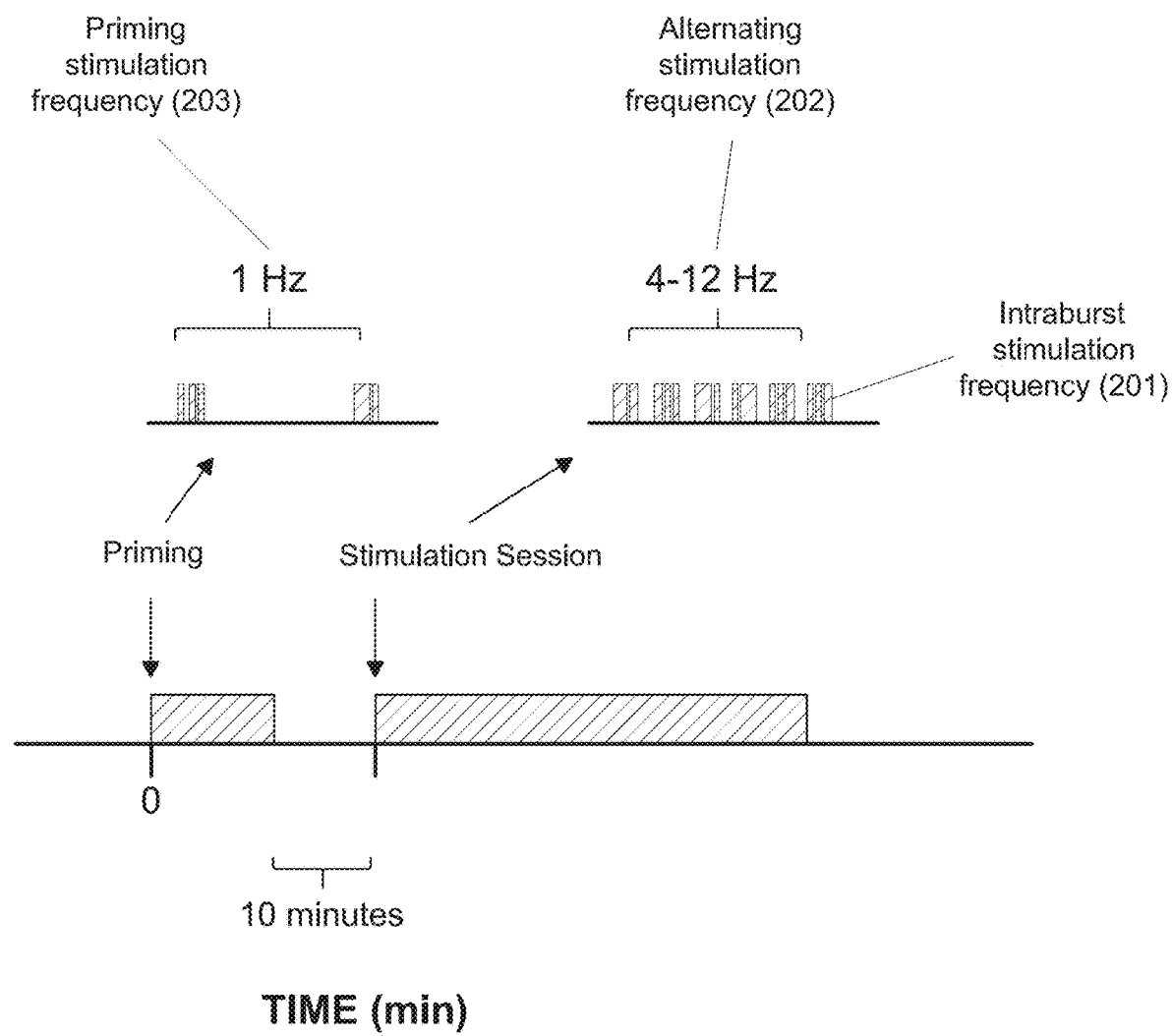

FIG. 15 schematically illustrates a priming sequence according to some embodiments of the invention.

Figure 16A:
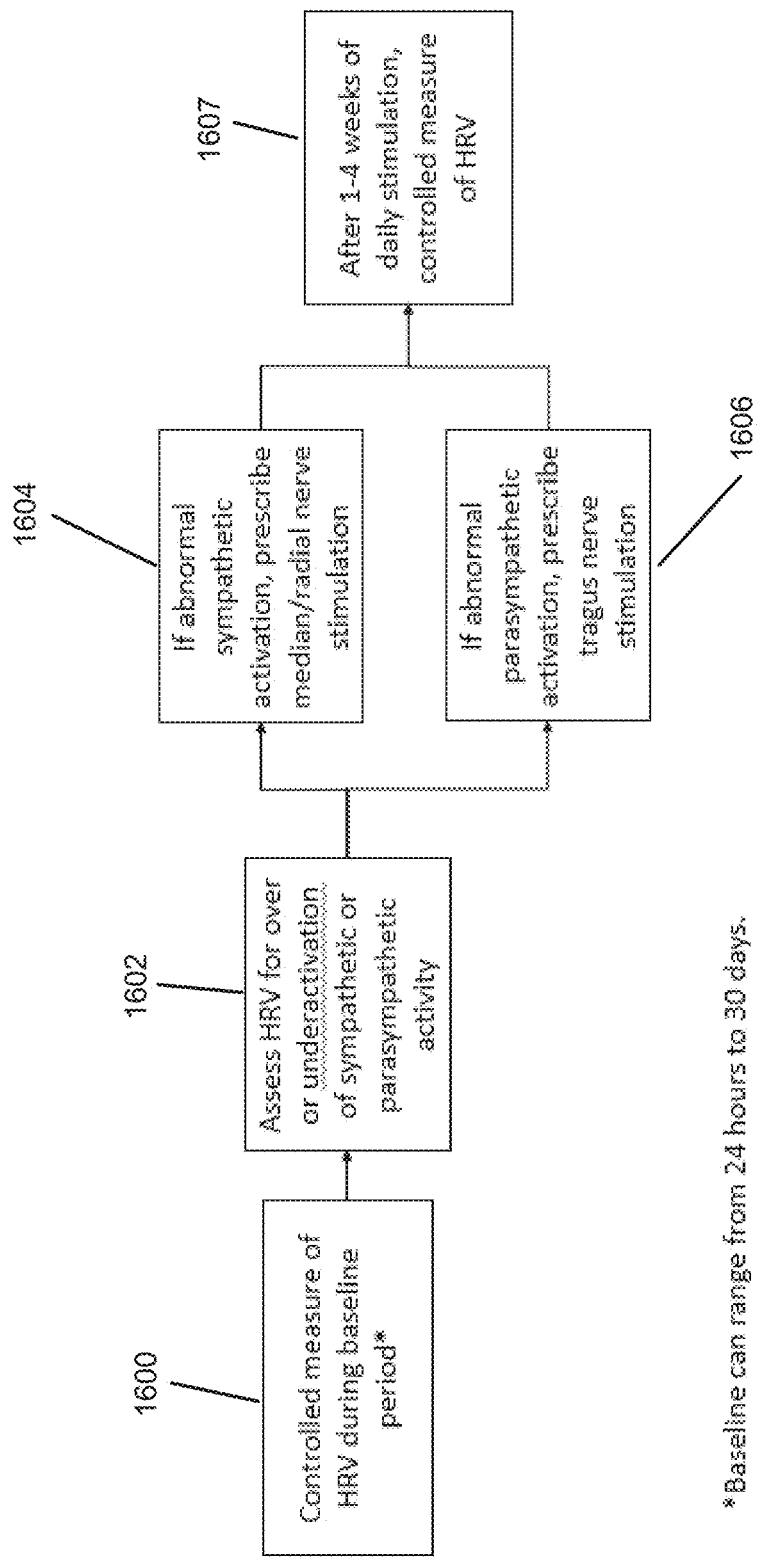
Figure 16B:
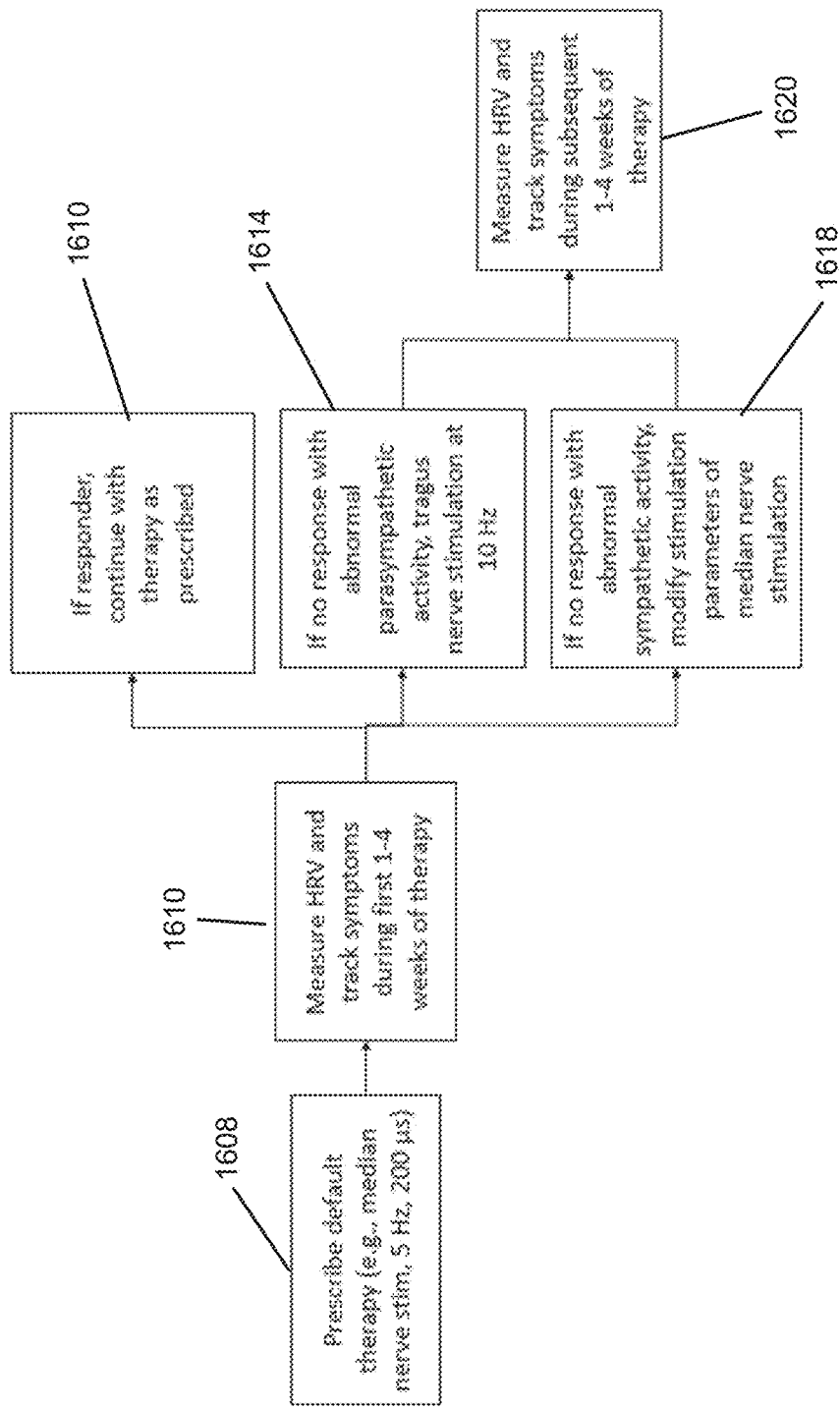
Figure 16C:
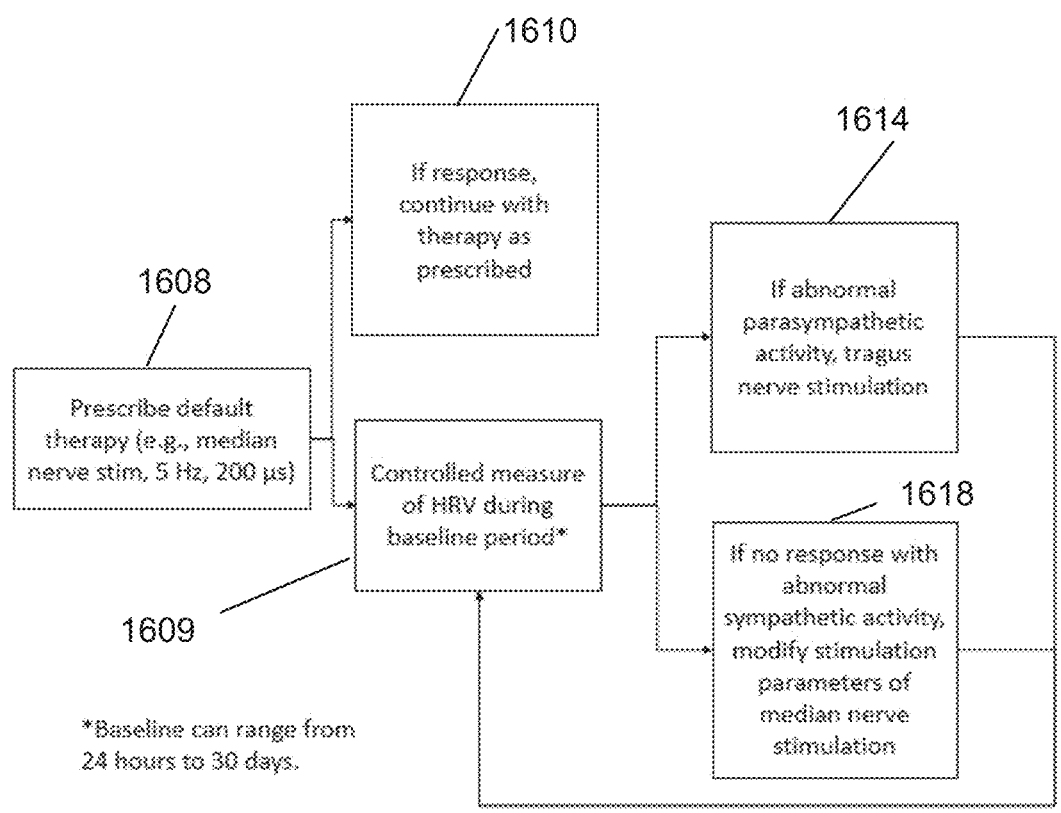

FIGS. 16A-16C are flow charts including potential treatment steps, according to some embodiments of the invention.

Figure 17:
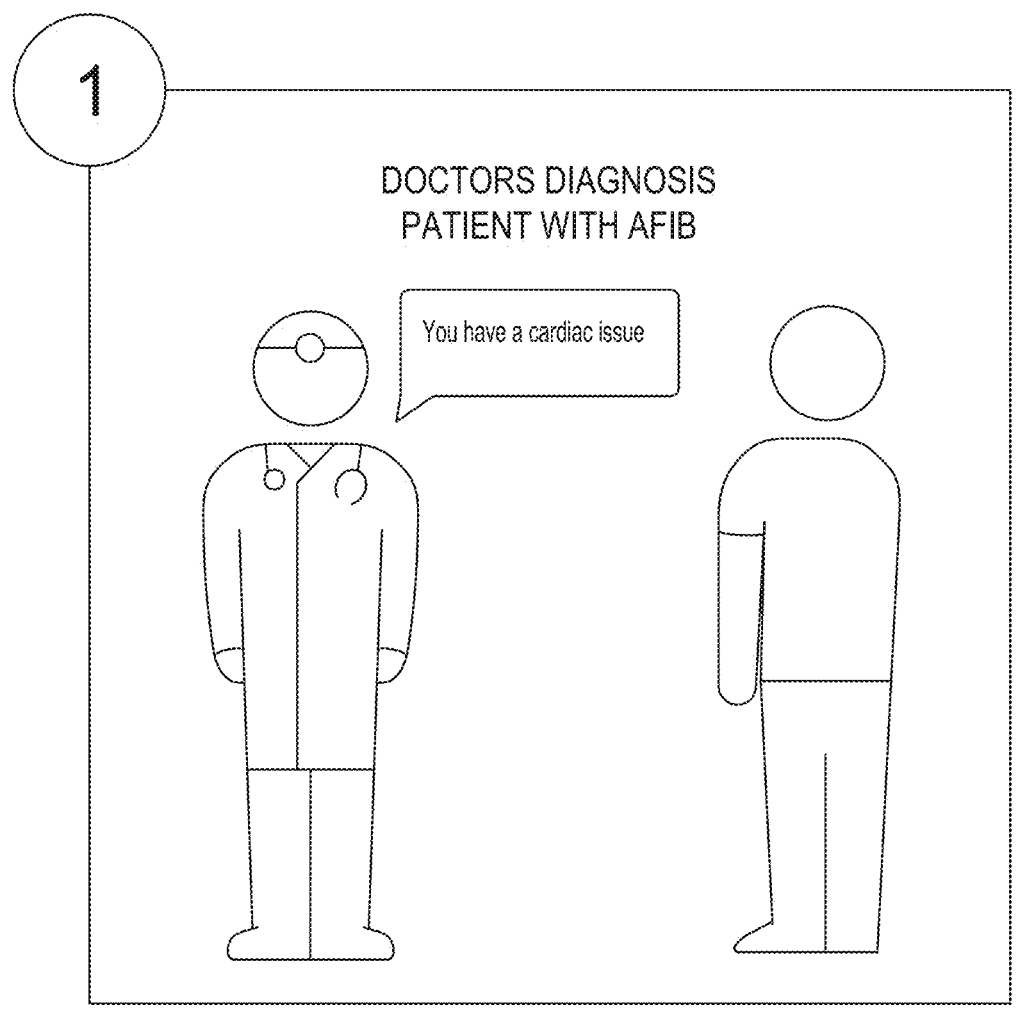
Figure 17:
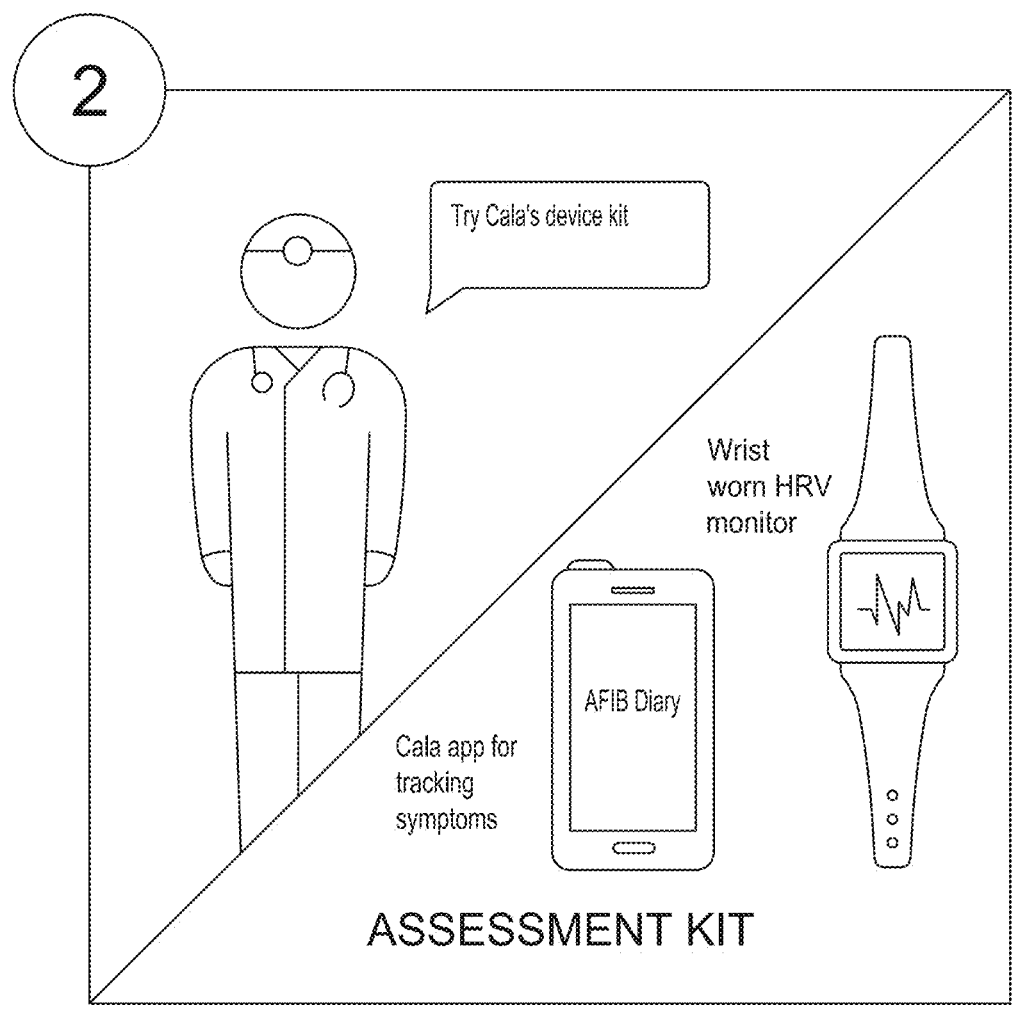
Figure 17:
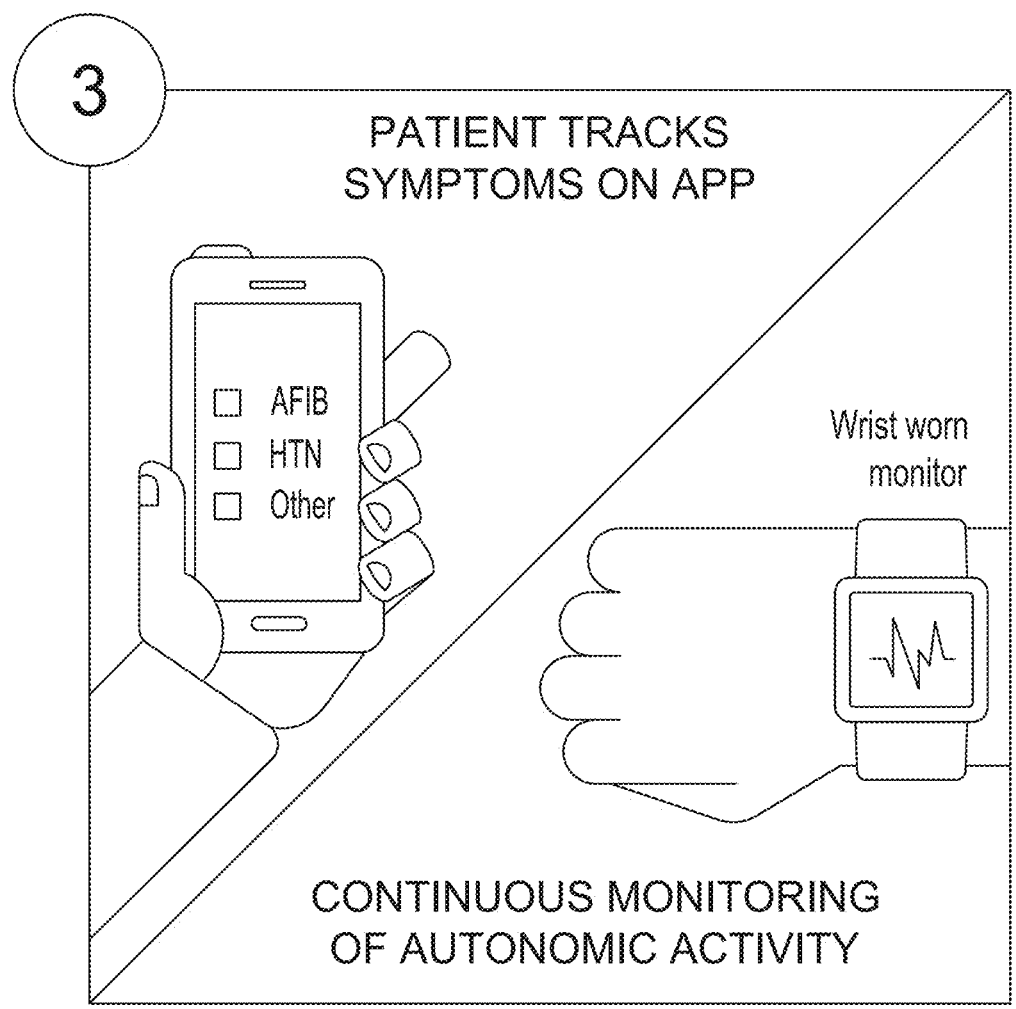
Figure 17:
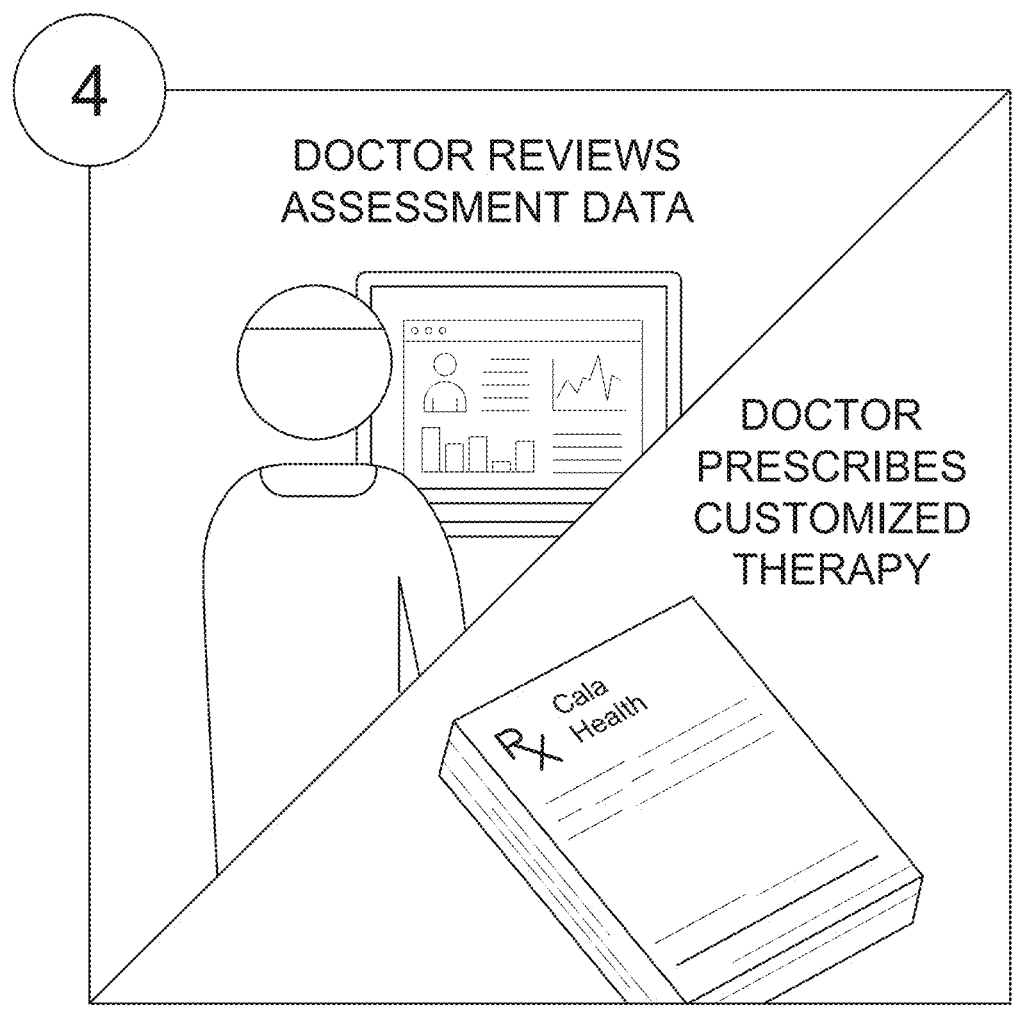

FIG. 17 schematically illustrates a diagnosis, assessment, and prescription flow chart for a subject with cardiac dysfunction, according to some embodiments of the invention.

DETAILED DESCRIPTION

Some cardiac diseases, such as hypertension and cardiac dysrhythmia, can be driven by an imbalance of autonomic activity; that is an imbalance of sympathetic and parasympathetic activity within the autonomic nervous system. This imbalance can arise from overactivity or underactivity of the sympathetic and/or parasympathetic limbs of the autonomic nervous system. Electrical stimulation that affects the autonomic nervous system including systems and methods as disclosed herein can provide therapeutic benefit by restoring balance to the autonomic nervous system, thus reducing the burden of symptoms associated with these cardiac diseases.

Autonomic nerve activity has been shown as an important trigger for cardiac dysrhythmia. Human skin is well innervated with autonomic nerves and stimulation of nerve or meridian points as disclosed herein can potentially help in treatment of cardiac dysrhythmia. For example, afferent nerves in the periphery or distal limbs, including but not limited to median nerve, are connected by neural circuits to the arcuate nucleus of the hypothalamus. Not to be limited by theory, modulation of the arcuate nucleus reduces elevated sympathetic outflow via either or both of the following pathways: descending input into the neuroendocrine or hormonal system from the pituitary gland and descending input via the ventrolateral peri-acqueductal grey in the midbrain and the nucleus raphe pallidus in the medulla to the rostral ventrolateral medulla (RVLM). This pathway may be via the cholinergic mu-receptors.

Figure 1:
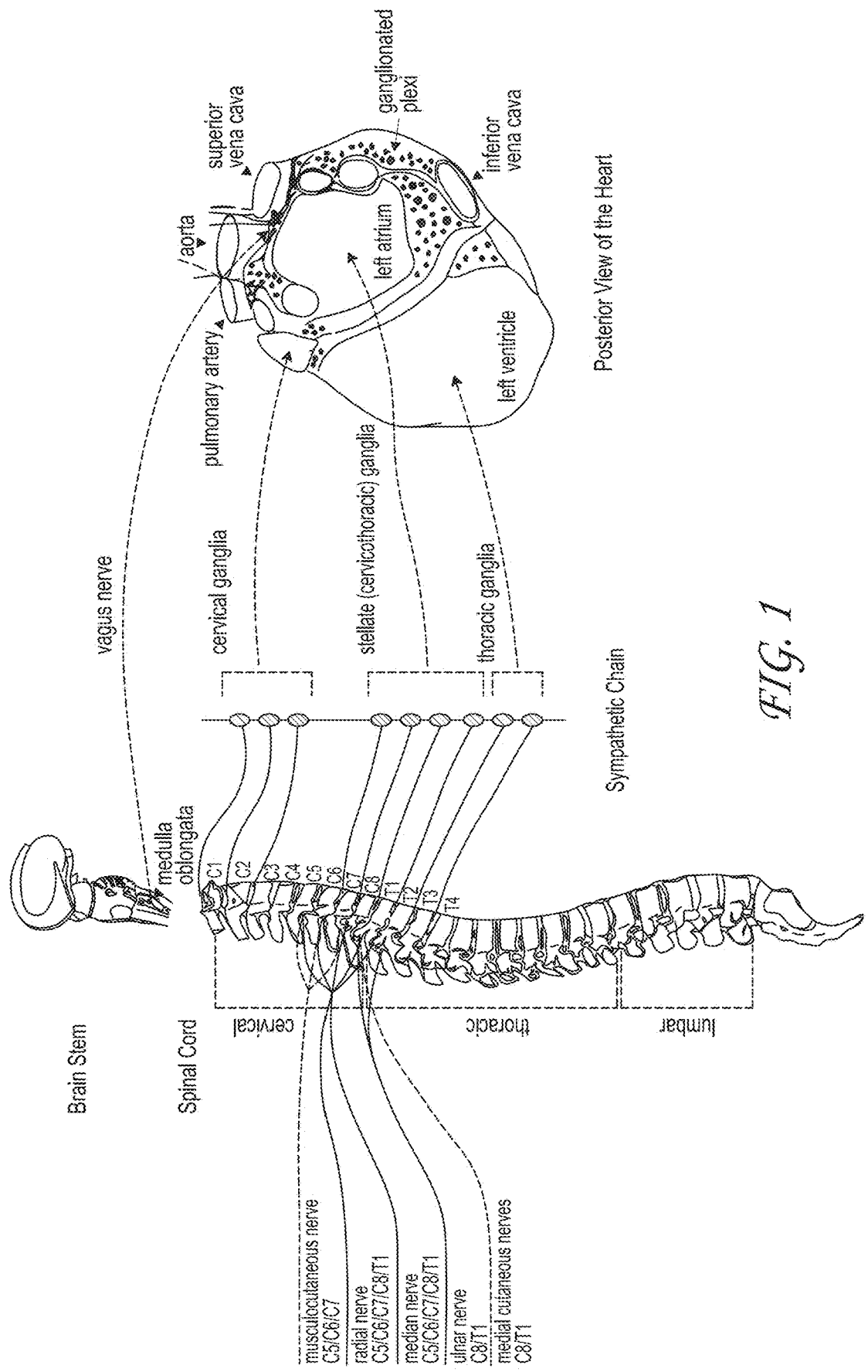
FIG. 1 schematically illustrates relationships between select peripheral nerves, spinal cord levels, the sympathetic chain, and the heart.
Figure 1E:
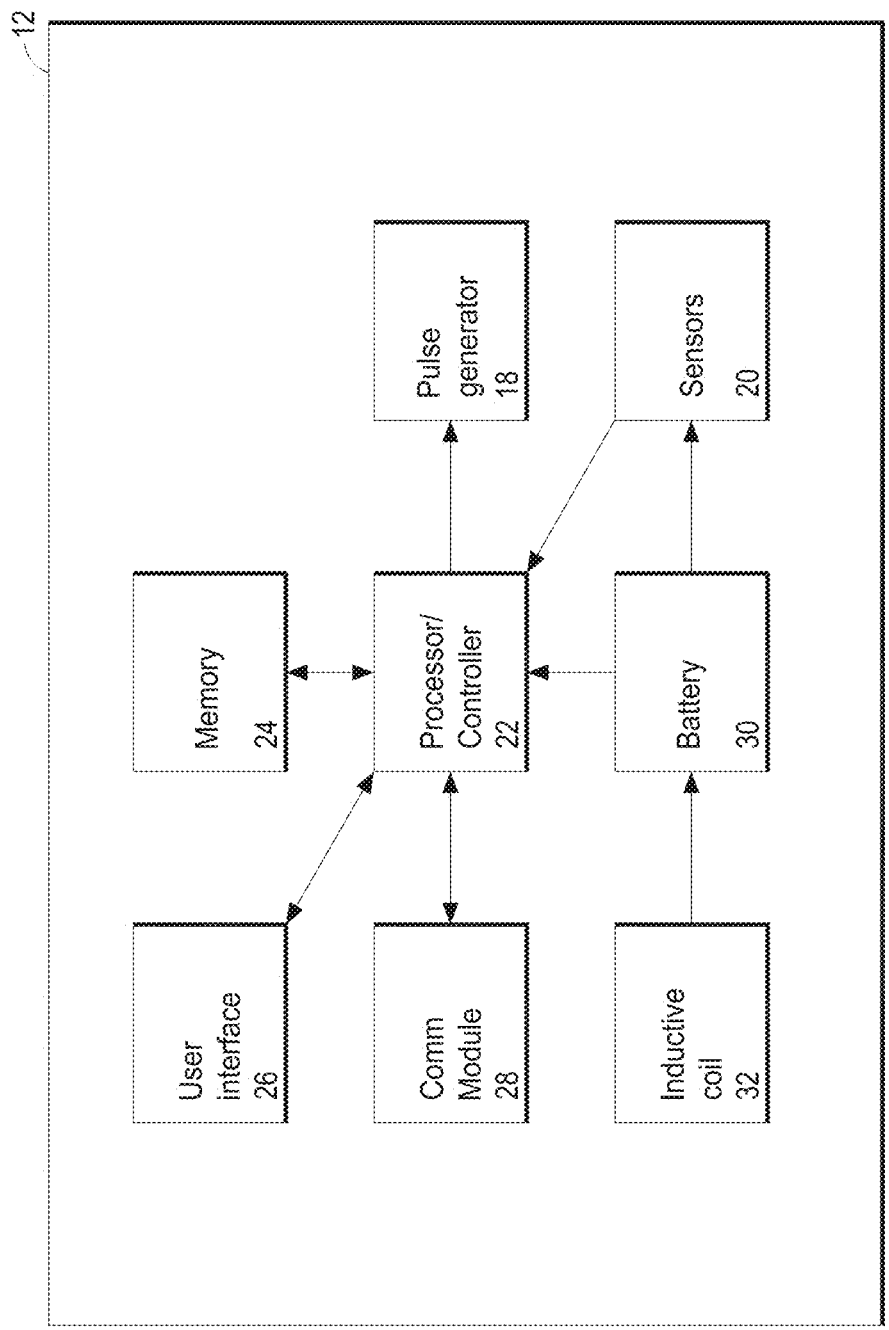

Alternatively or in addition, stimulation of peripheral cutaneous fibers in the arm, leg, neck, or tragus may modulate activity of the stellate ganglion at the level of C8-T1 of the spinal cord to reduce elevated sympathetic outflow and/or increase vagal tone via the carotid sinus nerve. Not to be limited by theory, FIG. 1 schematically illustrates relationships between select peripheral nerves, spinal cord levels, the sympathetic chain, and the heart. Shown on the left side of the figure are peripheral nerves including the musculocutaneous nerve (innervated at C5-C7), the radial nerve (innervated at C5-T1), the median nerve (innervated at C5-T1), the ulnar nerve (innervated at C8-T1), and the medial cutaneous nerves (innervated at C8-T1). The medulla oblongata is operably connected to the vagus nerve, which has parasympathetic effects in, for example, the SA and AV nodes of the heart. The cervical ganglia are paravertebral ganglia of the sympathetic nervous system. Preganglionic nerves from the thoracic spinal cord can enter into the cervical ganglions and synapse with its postganglionic fibers or nerves. The cervical ganglion has three paravertebral ganglia: superior cervical ganglion adjacent to C2 & C3; postganglionic axon projects to target: (heart, head, neck) via a pathway adjacent the carotid arteries; middle cervical ganglion (smallest)—adjacent to C6; targeting the heart and the neck; and the inferior cervical ganglion. The inferior ganglion may be fused with the first thoracic ganglion to form a single structure, the stellate ganglion—adjacent to C7; targeting the heart, lower neck, arm, posterior cranial arteries. Nerves emerging from cervical sympathetic ganglia contribute to the cardiac plexus, for example. The stellate ganglion (or cervicothoracic ganglion) is a sympathetic ganglion formed by the fusion of the inferior cervical ganglion and the first thoracic ganglion. Emerging from the thoracic ganglia are thoracic splanchnic nerves (the cardiopulmonary, the greater, lesser, and least splanchnic nerves) that help provide sympathetic innervation to abdominal structures. As illustrated in FIG. 1, peripheral nerve stimulation can have a substantial clinical effect on the autonomic nervous system, and thus the heart and cardiovascular system.

Alternatively or in addition, and not to be limited by theory, electrical stimulation can invoke a neurohormonal response by myofascial or cutaneous stimulation of acupressure points in the upper and lower extremities, such as Ht7, Pc6, Gb34, Sp6, Ki6, etc. Neurohormonal responses can include changes (increase or decrease) in production of norepinephrine, epinephrine, acetylcholine, and/or inflammatory cytokines. Inflammatory cytokines can include interleukin, high-mobility group-box 1 protein, and/or tumor necrosis factor alpha. Neurohormonal response can also be invoked by afferent and/or efferent nerve stimulation of median, radial, ulnar, or vagus nerve, cutaneous nerves or sympathetic nerves. In one embodiment, one or more of norepinephrine, epinephrine, acetylcholine, and/or inflammatory cytokines are reduced post treatment with the devices disclosed herein by at least about 5%, 10-20%, 20-40%, 40-60% or more (including overlapping ranges therein) compared to pre-treatment.

Alternatively or in addition, and not to be limited by theory, antidromic stimulation of autonomic or visceral efferent nerve fibers in the arm, leg, neck, or tragus may modulate sympathetic outflow and/or modulate vagal tone. Specifically, sympathetic efferents can be specifically stimulated by targeting c-fibers in the periphery of the body.

Alternatively or in addition, and not to be limited by theory, electrical stimulation of peripheral nerves, either somatic, autonomic, afferent, and/or efferent, can reduce sporadic electrical activity of the pulmonary veins, which trigger and maintain cardiac dysrhythmias.

Some embodiments, as shown in FIGS. 1A-1E for example, are related to a device and system that provides peripheral nerve stimulation, targeting individual nerves. Some embodiments involve a device and system 10 that allows customization and optimization of electrical treatment to an individual. In particular, the device 10 described can be configured for electrical stimulation of the median, radial, ulnar, peroneal, saphenous, tibial and/or other nerves or meridians accessible on the limbs for treating cardiac dysrhythmia, including but not limited to atrial fibrillation (such as chronic or paroxysmal atrial fibrillation) and other arrhythmias, and/or reducing cardiac dyssynchrony and/or hypertension. Other non-limiting examples of arrhythmias that can be treated using systems and methods as disclosed herein can include, for example, long QT syndrome, torsades de pointes, premature atrial contractions, wandering atrial pacemaker, multifocal atrial tachycardia, atrial flutter, supraventricular tachycardia (including PSVT), AV nodal reentrant tachycardia, junctional rhythm, junctional tachycardia, premature junctional complex, premature ventricular contractions, accelerated idioventricular rhythm, monomorphic ventricular tachycardia, polymorphic ventricular tachycardia, and ventricular fibrillation. Targeting those specific nerves and utilizing appropriately customized stimulation results in more effective therapy (e.g., reduced arrhythmia episodes such as fibrillations or fibrillation episodes and/or shorter duration of fibrillation episodes; reduced palpitations/sensation of arrhythmias; improved rate control of arrhythmias such as a decrease in heart rate of about or at least about 10%, 20%, 30%, 40%, or more compared to pre-treatment (with or without cessation of the arrhythmia); prevention or reduction in the rate of embolic events such as stroke associated with atrial fibrillation; and/or modulation, e.g., decreasing systolic, diastolic, and/or mean blood pressure). In some embodiments, therapy can prevent or reduce the recurrence rate of fibrillation in people with persistent atrial fibrillation (AF) after pharmaco- or electro-cardioversion; or the number and duration of fibrillation episodes in paroxysmal AF patients, including but not limited to reducing the number of arrhythmia recurrent episodes after an ablation procedure. In some embodiments, therapy can reduce or eliminate the number, dose, and/or frequency of medications that a patient may need to take for their underlying arrhythmia, advantageously reducing side effects/potential toxicities. In some embodiments, therapy can have an unexpectedly synergistic effect when combined with one, two, or more pharmacologic agents such as a rate-control agent (e.g., a beta-blocker such as for example atenolol, metoprolol, propranolol, carvedilol; a calcium-channel blocker such as for example nifedipine, amlodipine, diltiazem, or verapamil; or a cardiac glycoside such as digoxin) and/or an anti-arrhythmic agent (e.g., quinidine, procainamide, disopyramide, lidocaine, mexiletine, flecainide, propafenone, sotalol, ibutilide, dofetilide, amiodarone or dronedarone). In some embodiments, a cardiac glycoside such as digoxin can be administered orally, intravenously, or another route along with peripheral nerve stimulation protocols such as described herein for an unexpected synergistically beneficial effect in treating cardiac arrhythmias, cardiac dyssynchrony, and/or hypertension. Not to be limited by theory, digitalis glycosides and cardiac glycosides, sometimes referred to as digoxin or deacetyllanatoside C., can modulate arterial baroreflex mechanisms in humans. A diminishing of the baroreceptor reflex can lead to continuous and excessive sympathetic activity, which in turn can lead to an increase in heart rate, blood pressure, and the initiation and maintenance of cardiac dysrhythmias. Abnormal baroreceptor function can be related to elevated activation of the sodium-potassium ATPase pump; digitalis glycosides and cardiac glycosides act to decrease this elevated activation, which leads to increased sensitivity of the baroreceptors, including sensitivity to stimulation. Thus, electrical stimulation of peripheral nerves that modulates the baroreceptors, e.g., median, radial, ulnar or cutaneous fibers of the arm, can have an unexpectedly synergistic effect with digitalis glycosides and cardiac glycosides to inhibit elevated sympathetic activity; the glycosides increase sensitivity of the baroreceptor reflex, and stimulation activates the baroreceptor reflex. This synergistic effect can be advantageous by reducing the required dosage of the glycosides to treat cardiac dysfunction, such as hypertension or cardiac dysrhythmias, as the therapeutic index of digoxin is very narrow and severe toxic effects may occur at plasma concentrations only twice the therapeutic plasma concentration range. In some embodiments, the dose of cardiac glycoside, such as digoxin, administered to the patient can be much less than conventionally prescribed, such as about or less than about 3, 2.8, 2.6, 2.4, 2.2, 2.0, 1.8, 1.6, 1.4, 1.2, 1.0, 0.8, 0.6, 0.4 or 0.2 mcg/kg per day. In some embodiments, the dose of cardiac glycoside can be titrated to a blood level that is less than therapeutic, for example, about or less than about 1.5, 1.4, 1.3, 1.2, 1.1, 1.0, 0.9, 0.8, 0.7, 0.6, 0.5, 0.4, 0.3, 0.2, or 0.1 ng/ml. In some embodiments, the digoxin is provided in single-dose forms of administration (e.g., a tablet) of about or less than about 250 mcg, 125 mcg, 62.5 mcg, 31.25 mcg, 16 mcg, 8 mcg, 4 mcg, 2 mcg, 1 mcg, or less.

Afferent nerves in the periphery or distal limbs, including but not limited to the median nerve, are connected via neural pathways to the arcuate nucleus of the hypothalamus, as illustrated schematically in FIG. 12A. Not to be limited by theory, but in some cases modulation of the arcuate nucleus can reduce elevated sympathetic outflow via two pathways: (1) descending input into the neuroendocrine or hormonal system from the pituitary gland and (2) descending input via the ventrolateral peri-acqueductal grey in the midbrain and the nucleus raphe pallidus in the medulla to the rostral ventrolateral medulla (RVLM). This pathway can also be via the cholinergic mu-receptors.

Not to be limited by theory, radial nerve stimulation can prevent arrhythmias by inhibiting the nucleus of the solitary tract and vagal nuclei, inhibiting the aortic depressor nerve, and thereby the parasympathetic cardiac input; median nerve stimulation can prevent arrhythmias by exciting the arcuate nucleus-ventral periaqueductal gray-nuclei raphe pathway, inhibiting the rostral ventrolateral medulla (rVLM) and thereby the sympathetic cardiac input, as illustrated schematically in FIG. 12B. Alternatively, median, radial, and/or ulnar nerve stimulation can modulate sympathetic outflow via a neural pathway involving the stellate ganglion; tragus nerve stimulation modulates vagal tone directly via the vagus nerve. In combination, stimulation of the two sites can restore autonomic balance.

FIGS. 1A-1E illustrate an embodiment of a device and system 10 that provides transcutaneous peripheral nerve stimulation, targeting individual nerves, to treat cardiac dysrhythmias, reduce cardiac dyssynchrony, and/or reduce blood pressure. In some embodiments, the device 10 is designed to be worn on the wrist or arm. In some embodiments, electronics located in a watch-like housing 12 measure blood pressure and also generate an electrical stimulation waveform. Electrical contacts in a band 14 and/or housing 12 transmit the stimulation waveform to the disposable electrodes 16. The location of the contacts in the band 12 is arranged such that one or more specific nerves are targeted at the wrist, such as the median, radial, and/or ulnar nerves. The electronics housing 12 also can have a digital display screen to provide feedback about the stimulation and measured cardiac rhythm and/or blood pressure characteristics and history to the wearer of the device.

In some embodiments, the treatment device 10 is a wrist-worn device that can include, for example, 1) an array of electrodes 16 encircling the wrist, 2) a skin interface to ensure good electrical contact to the person, 3) an electronics box or housing 12 containing the stimulator or pulse generator 18, sensors 20, and other associated electronics such as a controller or processor 22 for executing instructions, memory 24 for storing instructions, a user interface 26 which can include a display and buttons, a communications module 28, a battery 30 that can be rechargeable, and optionally an inductive coil 32 for charging the battery 30, and the like, and 4) a band to hold all the components together and securely fasten the device around the wrist of an individual.

Typically for nerve excitation in the wrist, two electrodes 200' are placed longitudinally along the nerve with a reasonable spacing of at least 1 cm, as shown in FIG. 2B, which typically results in band width of at least 1 cm where the electrodes are located. The purpose of this positioning is to get the electric field 202' to penetrate into the tissue to depolarize the underlying nerve 204. With two adjacent electrodes 200', there is only a shallow penetration of the stimulating current. In contrast as shown in FIG. 2A, with electrodes 200 placed circumferentially around the wrist and excited on opposite sides of the wrist, the electric field 202 extends through the wrist and this enables excitation of nerves 204 deeper in the tissue. Therefore, the circumferential array is compact, allowing a band width that is approximately the same size as the electrode width, and thus advantageous for wearable devices. In some embodiments, the advantage of having the configurability of the array is that the same nerves can be reached, but in a more compact form factor than conventional median nerve excitation. The devices described herein may be described and illustrated with electrodes placed circumferentially or longitudinally, but it should be understood that either electrode configuration can be used by the devices. In addition, the devices may be described and shown with 2, 3 or more electrodes, but it should be understood that the device can have only 2 electrodes, or can have more than 2 electrodes. Some devices may be designed to stimulate just a single nerve, such as the median nerve, and some devices may be designed to stimulate more than one nerve.

FIG. 2C illustrates a system that can be configured to stimulates multiple dermatomes similarly in a timed manner with an array of electrodes embedded in a sleeve across the arm by stimulating adjacent pairs of electrodes at regular intervals such that specific points along the nerve are stimulated. Dermatomes in the arm that carry sensory information that can be stimulated, including for example C5 (lateral aspect of the upper extremity at and above the elbow); C6 (the forearm and radial side of the hand); C7 (the middle finger); C8 (the skin over the little finger and the medial aspect of each hand); T1 (the medial side of the forearm); and T2 (the medial and upper aspect of the arm and the axillary region).

In some embodiments, electrodes can be positioned to selectively target specific nerves in the arm or specific dermatomes associated with levels of nerve innervation into the spinal cord. The illustrations of FIGS. 2D-2S depict various options for targeting these nerves or regions. In some cases, to stimulate a specific nerve, the active electrode can be aligned directly over the nerve such that the path of electrical current flows from the active electrode through the nerve (and surrounding tissue) to the return electrode. Along with electrode alignment or configuration, successful stimulation of the nerve depends on various factors, including size and shape of the electrode, stimulation waveform parameters, such as pulse width and frequency, and the amplitude of the stimulation. Using 22 mm×22 mm sized electrodes for example, shifting the active electrode by, for example, about, least about, or no more than about 5, 6, 7, 8, 9, 10, 11, 12, 13, 14, 15 or more mm (or ranges incorporating any two of the aforementioned values) either medially or laterally of the target nerve can preclude stimulation of the nerve and instead stimulates cutaneous fibers of the adjacent dermatome.

Additionally, higher current levels can be required to transcutaneously stimulate nerves that are deeper under the surface of the skin. The median, radial, and ulnar nerves tend to be closer to the skin surface more distal on the arm (i.e., closer to the wrist), thus it can be advantageous in some cases to selectively target dermatomes more proximally on the arm to avoid also stimulation the major nerves.

To stimulate a dermatome, the active electrode can be placed in a region of the dermatome that is not directly over an adjacent nerve, such as offset about 5, 6, 7, 8, 9, 10, 11, 12, 13, 14, or 15 mm (or ranges including any two of the aforementioned values) medially or laterally from the off-target nerve in some cases. FIGS. 2D-2S depict various electrode configurations, including in-line configurations where the active and return electrodes are aligned with the axon of the nerves, and a circumferential configuration where the active and return electrodes are on opposite sides of the arm. FIG. 2D illustrates an embodiment of target stimulation locations and transverse placement for active and return electrodes for targeting the radial, median, and/or ulnar nerves; while FIG. 2E illustrates an embodiment of target stimulation locations and transverse placement for active and return electrodes for targeting the C6, C8, and T1 dermatomes.

FIG. 2F illustrates an embodiment of a target transverse electrode configuration for the median nerve, while FIG. 2G illustrates an embodiment of a target transverse electrode configuration for the T1 dermatome.

FIG. 2H illustrates an embodiment of a target transverse electrode configuration for the radial nerve, while FIG. 2I illustrates an embodiment of a target transverse electrode configuration for the C8 dermatome.

FIG. 2J illustrates an embodiment of a target electrode transverse configuration for the ulnar nerve, while FIG. 2K illustrates an embodiment of a target transverse electrode configuration for the C6 dermatome.

FIG. 2L illustrates an embodiment of target stimulation locations and in line placement for active and return electrodes for targeting the radial, median, and/or ulnar nerves; while FIG. 2M illustrates an embodiment of target stimulation locations and in line placement for active and return electrodes for targeting the C6, C8, and T1 dermatomes.

FIG. 2N illustrates an embodiment of a target in line electrode configuration for the median nerve, while FIG. 2O illustrates an embodiment of a target in line electrode configuration for the T1 dermatome.

FIG. 2P illustrates an embodiment of a target in line electrode configuration for the radial nerve, while FIG. 2Q illustrates an embodiment of a target in line electrode configuration for the C8 dermatome.

FIG. 2R illustrates an embodiment of a target electrode in line configuration for the ulnar nerve, while FIG. 2S illustrates an embodiment of a target in line electrode configuration for the C6 dermatome.

In some embodiments, stimulating three or more electrodes can be used to stimulate two or more nerves or dermatomes. In some embodiments as shown in FIG. 2T the electronics and electrical circuit 1200 used to drive the array can include an adaptable switch that allows each individual electrode 1202 to be connected to either one of the two contacts 1204, 1206 of the stimulator 1208 at a given time by opening or closing switches 1210 in each channel. Each channel can include a DC blocking circuit 1212, as charge balance can be important to prevent skin irritation and burns, and also be individually current limited by current IO limiters 1214 in order to prevent current surges that could cause injury or discomfort. This current limitation can be set to a predetermined tolerability threshold for a particular patient or group of patients.

There are many transistor circuits or components like polyfuses to limit or shutdown the current to a particular node. These circuits and its components, such as the stimulator, switches, and current limiters, can be controlled and/or be programmable by a microprocessor 1216 in real-time. The 15 switch matrix allows multiple electrodes to be connected to the same stimulator contacts at a given time for maximum flexibility. In addition, electrodes can be switched between the positive and negative contacts of the stimulator to produce a bipolar pulse.

FIG. 2U shows an embodiment of a wearable band 900 with integrated electrodes 902, 904. The integrated electrodes 902, 904 can be dry electrodes in electrical communication with a detachable controller 910 through a flexible circuit embedded in the band. In some cases, dry electrodes may be more suitable for longer term use electrodes that can be used for months, such as at least 1, 2, or 3 months, before the band needs to be replaced. In some embodiments, the band may be a single use band that can be used for a relatively long period of time before replacement.

In some embodiments, disclosed herein are systems and methods for stimulating a plurality of nerves for the treatment of cardiac dysfunction. Stimulation of 2, 3, or more nerves or dermatomes, such as the median, median cutaneous, radial, and/or ulnar nerve could be used for the treatment of conditions such as cardiac dysrhythmia. Dual nerve stimulation can in some cases synergistically increase the effectiveness of therapy by an effect at the brachial plexus, the proximal location where individual nerves converge near the spinal cord. For example, in one embodiment, the devices disclosed herein are used to stimulate two nerves (including but not limited to the median, radial, ulnar, or median cutaneous nerve) located at a distance from the brachial plexus at two different times, wherein, ultimately, the brachial plexus is stimulated by both signals from two or more nerves substantially simultaneously (e.g., less than about 2 ms, 1 ms, 0.5 ms, 0.4 ms, 0.3 ms, 0.2 ms, 0.1 ms, 0.09 ms, 0.08 ms, 0.07 ms, 0.06 ms, 0.05 ms, 0.04 ms, 0.03 ms, 0.02 ms, 0.01 ms, or less), but could be higher in some cases. In one embodiment, the two nerves are offset (in terms of timing of stimulation) by 0.1-3.0 ms. In one embodiment, two, three, four or more nerves located at a distance from a target (including but not limited to the brachial plexus) are stimulated at different times in order to hit the target at substantially the same time. In some embodiments, including those disclosed in connection with FIG. 2V below, the system can be configured to independently control stimulation of a first target nerve (including stimulation parameters such as frequency and others listed herein) and a second target nerve respectively. In other words, the first target nerve and the second target nerve can be stimulated with either the same or different parameters, and can be stimulated simultaneously or in alternating or other fashion. In some embodiments, the stimulation systems can include a plurality of independent stimulation circuits, or a common circuit with a controller configured to switch stimulation parameters for one, two, or more nerves.

In some embodiments, as illustrated schematically in FIG. 2V, a system 1400 can utilize three electrodes: a first electrode 1404 positioned over a first nerve, e.g., the tibial nerve 1402, a second electrode 1406 positioned over a second nerve, e.g., the saphenous nerve 1408, and a third electrode 1410 positioned, for example, on the outer side of the leg, opposite to the first two electrodes 1404, 1406. This third electrode 1410 would serve as a common cathode for the other two electrodes 1404, 1406. The three electrodes 1404, 1406, 1410 can be oriented in such a way that the electric fields between each of the first two electrodes 1404, 1406 and the common cathode 1410 pass through the tibial nerve 1402 and saphenous nerve 1408, respectively. In some embodiments, other nerves innervating the leg including, for example, the common peroneal nerve, the femoral nerve, the sacral nerve, the sciatic nerve, and the sural nerve can also be stimulated.

Embodiments of the invention can include a device and system and method to measure and collect biological data (e.g., heart rate, heart rate variability, ECG, galvanic skin response, temperature, and blood pressure), analyze the data as to interpret how these measures may influence cardiac rhythm and/or blood pressure, and provide peripheral nerve stimulation that targets one or more individual nerves, such as the median, ulnar, and/or radial nerve, to treat or prevent cardiac dysrhythmias, reduce cardiac dyssynchrony, and/or reduce blood pressure, where the stimulation applied may or may not be modified based on the measured data.

Embodiments of the therapy system can be flexible or adaptable to be worn on various locations of the body to access a specific nerve, such as the median nerve at the wrist or elbow or the saphenous or tibial nerves near the knee or ankle for example; or various nerves, such as the radial and/or ulnar nerves, or various acu-pressure or meridian points as shown in FIGS. 8A and 8B.

In some embodiments, the electrodes can be positioned for myofascial innervation, preferably near the Neiguan or PC 5-6 or PE5 or PE6 acupressure point, which is about 3 finger widths proximally from the wrist crease. Alternatively, the electrodes can be positioned distally on the arm, where the median nerves are closer to the skin surface, which requires less power and can provide a more comfortable transcutaneous simulation.

Embodiments of the therapy system can include any number of the following three components: (1) a monitoring unit having sensors, circuitry, and optionally may have a power source and/or a microcontroller. (2) a therapy unit having a stimulator (e.g., a pulse generator), circuitry, a power source and a microcontroller, and (3) a skin interface having electrodes and electrical connections for electrically connecting the electrodes to the therapy unit. In some embodiments, all three components are separate components that can be reversibly attached to each other to form a wearable therapy system. In some embodiments, any two of the components can be combined or integrated together to form a wearable two part system that can be reversibly attached to each other. It should be noted that some functions can crossover, such as the electrodes of the skin interface being used as sensors to measure electrical activity (e.g. EMG and ECG) and impedance, for example. In some embodiments, any one of the detachable components can be disposable and/or can be sent back to the manufacturer for recycling. In some embodiments, the sensor can be separate, such as a band with a pressure sensor around the arm to measure blood pressure, which can wirelessly communicate with the stimulator.

In some embodiments, some or all of components of the therapy system can be implantable, percutaneous, and/or transcutaneous. For example, the stimulation electrodes may be implanted in the vicinity of a target nerve. Electrical power can be delivered to the electrodes via a wired connection or wirelessly. Implanted electrodes can have various shapes to direct the flow of current toward the target nerve, including but not limited to a nerve cuff or electrodes that might be cylindrical or flat (plate shaped). The stimulation electrodes can also be inserted percutaneously or transcutaneously. Alternatively, sensors, such as a cardiac monitor, can be implanted in a location such that they are able to continuously measure electrical activity (e.g., a loop recorder), like in the chest or in the wrist, percutaneous, and/or transcutaneous. Implanted components can also communicate with other components of the therapy system via wired connection or wirelessly.

One embodiment, as shown in FIG. 3A, is a two-part system 310 including a monitor unit 312 that can be wearable in some embodiments and a therapy unit 314. In some embodiments, the therapy unit 314 can be can be detachable and can be reversibly attached to the wearable monitor unit 312. The therapy unit 314 may contain an electrical stimulation signal generator 316, power source 318, and a microprocessor and/or microcontroller 320 to control the stimulation. The therapy unit 314 can reversibly connect and communicate directly and/or wirelessly to the wearable monitor 312. In some embodiments, the therapy unit 314 may remain separate from the wearable monitor unit 312 and can communicate wirelessly with the wearable monitor unit 312. In some embodiments, the therapy unit 314 can have a data/power port 315, such as a USB port that allows a user to charge the power source 318, update the software and/or parameters on the microcontroller 320, and/or retrieve data from memory on the wearable monitor unit 312 and/or therapy unit 314. In some embodiments, the data/power port can be located on the wearable monitor unit 312 or both the wearable monitor unit 12 and therapy unit 314. In some embodiments, the wearable monitor unit 312 and/or therapy unit 314 can communicate wirelessly with an external computing device to update the software and/or parameters and/or retrieve data.

In some embodiments, the wearable monitor unit 312 can have a housing with a user interface 322 that encloses one or more sensors 324. In some embodiments, the wearable monitor 312 can be used to measure heart rate, rhythm, blood pressure, or other measures correlated or related to cardiac dysrhythmias, cardiac dyssynchrony, cardiac activity, hypertension, heart failure, or response of the sympathetic nervous system. In some embodiments, the wearable monitor 312 can have one or more electrodes 326 located on the base of the housing that makes contact with the patient's skin. In addition or alternatively, the wearable monitor 312 can have a band 328 or other securement feature with one or more electrodes on the skin facing side of the band 328. In some embodiments, the wearable monitor unit 312 has 2 or 3 electrodes, or at least 2 or 3 electrodes. In some embodiments, the wearable monitor unit 312 lacks a power source and relies on the power source 318 in the therapy unit 314 for power. In other embodiments, both the wearable monitor unit 312 and the therapy unit 314 have power sources. In some embodiments, only the wearable monitor unit 312 has a power source and the therapy unit relies on power from the monitoring unit.

In some embodiments, as shown in FIG. 3B, the therapy unit 314' may directly make contact with the wearer's skin and have the capability to provide electrical stimulation of targeted nerves, such as the median, radial, and/or ulnar, using electrodes 326. In some embodiments, the therapy unit 14' has 2 or 3 electrodes, or at least 2 or 3 electrodes. These electrodes 326 may be located on the housing of the therapy unit 314' and/or the therapy unit 314' may also have a band 328 or securement feature with electrodes 326. In some embodiments, when the therapy unit 314' has electrodes 326, the wearable monitor unit 312' does not have electrodes. In some embodiments, both the monitor unit and the therapy unit can have electrodes. As above, the therapy unit 314' can have a stimulator 316, power source 318, and microcontroller 320. The wearable monitor unit 312' can have a user interface 322 and one or more sensors 324 and, optionally, a power source 330 and microcontroller 321. In some embodiments, when the monitor unit has a power source 330 and/or a microcontroller 321, the therapy unit does not have a power source and/or a microcontroller. In some embodiments, the wearable monitor unit 312' is a smart watch or other wearable device, such as the Apple Watch or an Android based smart watch, with an application that allows the wearable device to communicate with the therapy unit and perform as a monitor unit. In some embodiments, the wearable monitor unit 312' can communicate with the therapy unit 314' wirelessly, and one or both of these devices can also communicate with an external computing device wirelessly. In some embodiments, one or both of the wearable monitor unit 312' and the therapy unit 314' can have a data/power port 315. In some embodiments, the wearable monitor unit 312 and the therapy unit 314' can be connected to each other through the data/power ports 315.

In some embodiments, the sensors can be located in or on the therapy unit instead of the monitoring unit. In some embodiments, the sensors can be located on both the therapy unit and the monitoring unit. In some embodiments, one or more sensors can be located on a separate wearable device, such as a sensor on a band that can be worn around the arm, leg, neck, or chest, or a sensor implanted inside the body, which may communicate via a wired or wireless connection with the therapy unit and/or the monitoring unit.

In some embodiments, the monitor unit can instead be carried by the user in, for example, the user's hand or pocket, rather than be worn. For example, a monitor unit carried by the user can be a smart phone, such as an Android smartphone or iPhone.

In some embodiments, the two part system or the monitor unit may instruct the user to perform an action, such as to sit and relax the arm, or to remain still or to attempt to remain still while the wearable monitor unit takes a measurement with one of the sensors.

In some embodiments, the user interface can include a display. In some embodiments, the display can be a touch screen display or capacitive sensor. In some embodiments, the display can be an array of LED lights. In some embodiments, the user interface can include one or more buttons, a dial, and/or a keyboard.

In some embodiments, the electrodes can be dry-contact (e.g., fabric, metal, silicone or any other plastic impregnated with conductive fillers, or a combination), use a conductive gel (e.g., hydrogels), or have a wet electrode surface (e.g., a sponge with water or conductive liquids or gels), or have fine micro needles, for example. In some embodiments, the electrodes can have a foam backing.

In some embodiments, the monitor unit can be a wearable monitor having a housing with a user interface. The housing can use a plurality of sensors to collect, store, and analyze biological measures about the wearer including, but not limited to, blood pressure, motion (e.g., accelerometers, gyroscopes, magnetometer, bend sensors), muscle activity (e.g., EMG using electrodes), cardiovascular rhythm measures (e.g., heart rate, heart rate variability, or ventricular and/or atrial dyssynchrony using electrodes to measure ECG, heart rhythm abnormalities), skin conductance (e.g., skin conductance response, galvanic skin response, using electrodes), respiratory rate, skin temperature, pupil diameter, and sleep state (e.g., awake, light sleep, deep sleep, REM). Heart rhythm measures can be recorded with optical, electrical, and/or accelerometery-based sensors. In particular, studies have shown that increased stress levels can increase blood pressure. Activities such as exercise, can also affect cardiac rate and/or rhythm, and/or affect blood pressure—measuring accelerometry (motion), heart rate, etc. could help identify these activities and normalize the measurements by similar activities. Additionally, hypertension has been correlated with heart failure—measuring ventricle dyssynchrony with ECG sensors could help identify the effectiveness of the stimulation to chronically reduce hypertension. Thus, using standard statistical analysis, machine learning, deep learning, or big data techniques, such as a logistical regression or Naïve Bayes classifier, these biological measures can be analyzed to assess a person's state, such as level of stress, which in turn, can serve as a predictor for increases in cardiac dysrhythmia, cardiac dyssynchrony, and/or blood pressure. In some embodiments, the device can provide stimulation based on measurements of one or more biological measures, a determination of a person's state, and/or a prediction of cardiac dysrhythmia, cardiac dyssynchrony, and/or a change in blood pressure.

In some embodiments, the responsiveness could be dependent on activity. For instance in arrhythmias that may be exacerbated with activity, a motion sensor such as an accelerometer or gyroscope could sense if a person is exercising, for example. During that time, the device could turn on to provide appropriate stimulation. In some embodiments, the device could turn off once the activity is complete. In some embodiments, the sensors could activate stimulation during periods of no activity (e.g., when the subject is sleeping).

In some embodiments, the responsiveness of stimulation could be dependent on one, two, or more sensors housed in the device to collect, store, and analyze biological measures about the wearer including, but not limited to, motion (e.g., accelerometers, gyroscopes, magnetometer, bend sensors), ground reaction force or foot pressure (e.g., force sensors or pressure insoles), muscle activity (e.g., EMG), cardiovascular measures (e.g., heart rate, heart rate variability (HRV), photoplethysmography (PPG), or ventricular and/or atrial dyssynchrony using electrodes to measure ECG and/or heart rhythm abnormalities), skin conductance (e.g., skin conductance response, galvanic skin response), respiratory rate, skin temperature, pupil diameter, and sleep state (e.g., awake, light sleep, deep sleep, REM). Using standard statistical analysis, machine learning, deep learning, or big data techniques, such as a logistical regression or a Naïve Bayesian classifier, these biological measures can be analyzed to assess the wearer's activity state, such as sedentary versus active, level of stress and the like, which in turn, can serve as a predictor for changes in blood pressure, cardiac arrhythmias, or cardiac dyssynchrony.

Sympathetic and parasympathetic activity can be measured through several methods, including microneurography (MSNA), catecholamine tests, heart rate, HRV, or galvanic skin response. HRV can provide a quick and effective approximation of autonomic activity in the body. HRV can be determined by analyzing the time intervals between heartbeats, also known as RR intervals. Heart rate can be accurately captured, for example, through recording devices such as chest straps or finger sensors. The differences between successive RR intervals can provide a picture of one's heart health and autonomic activity. Generally speaking, healthier hearts have more variability between successive RR-intervals. This interbeat data can also be used to denote an individual's sympathetic and parasympathetic activity levels. Through frequency-domain analysis, heartbeat frequencies can be separated into distinct bands. High-frequency signals (~0.15-0.4 Hz) can almost exclusively reflect parasympathetic activity, and low-frequency signals (~0.04-0.15 Hz) can represent a mixture of sympathetic and parasympathetic activity. Therefore, taking the ratio of high frequency (HF) to low frequency (LF) signals can yield an approximation of one's sympathetic tone. In some embodiments, HRV can be analyzed, for example, under time-domain, geometric domain methods in addition to frequency domain methods. In some embodiments, increased heart rate variability can signify increased parasympathetic response and/or decreased sympathetic response. Decreased heart rate variability can signify decreased parasympathetic response and/or increased sympathetic response. In some embodiments, a system can sense an increase or decrease in HRV of about or more than about 5%, 10%, 15%, 20%, 25%, 30%, 35%, 40%, 45%, 50%, 75%, 100%, or more over a baseline value (or target desired HRV value) and institute a change in one, two, or more stimulation modality parameters accordingly. In some embodiments, the one, two, or more stimulation modalities can be configured to modulate, such as increase or decrease stimulation to one or more nerves (e.g., peripheral nerves) associated with the sympathetic and/or parasympathetic nervous system, and a response to therapy can be confirmed by sensing an increase or decrease in parasympathetic or sympathetic tone, including but not limited to increase or decrease in HRV, changes in high frequency content of HRV, and changes in the ratio of high frequency and low frequency content of HRV. In some embodiments, balance of parasympathetic and sympathetic activity can be assessed with frequency analysis of heart rate variability measured with pulsed plethysmography with an LED light source and optical sensor disposed in the device that measures fluctuations in light level due to blood flow that target one of the major blood vessels around the knee (or in the arm or neck in other embodiments), which could include one or more of the following, femoral, popliteal, tibial, posterior tibial, anterior tibial, and/or descending genicular arteries or veins. In some embodiments, heart rate could be measured using accelerometer-based sensors or with electrical-based sensors, similar to single or multiple-lead ECG monitors.

A large source of error in optical measurements of heart rate is motion artifacts due to relative motion between the optical sensor and the blood vessel being measures. In some embodiments, the optical heart rate sensor has an adhesive on the side of housing that contacts the wearer's skin to reduce relative motion between the sensor and the target blood vessel.

HRV measurements in subjects with cardiovascular disease can be significantly different compared to controls. Through frequency-domain analysis, heartbeat frequencies can be separated into distinct bands. High-frequency signals (between about 0.15 Hz and about 0.4 Hz) can almost exclusively reflect parasympathetic activity, and low-frequency signals (between about 0.04 Hz and about 0.15 Hz) can represent a mixture of sympathetic and parasympathetic activity. In some embodiments, taking the ratio of high frequency (HF) to low frequency (LF) signals yields an approximation of one's sympathetic tone. Very low frequency (VLF) signals (between about 0.004 Hz and about 0.040 Hz) can also be evaluated to assess parasympathetic activity. The total power of HRV in the frequency domain can also be evaluated to assess autonomic activity.

Sympathetic and parasympathetic functions can also be evaluated, for example, by analyzing mean normal-to-normal intervals, e.g., all intervals between adjacent QRS complexes of measured cardiac rhythm, including the number of interval differences of successive NN intervals greater than 50 milliseconds; square root of the mean squared differences of successive NN intervals, and standard deviation of the NN intervals.

In some embodiments, sympathetic activity can also be assessed using more traditional techniques, such as measuring blood pressure changes before release and before starting a hand grip exercise, or measuring blood pressure changes before and after immersing the hand in a bath of cold water (e.g., cold pressor test). Parasympathetic activity can be assessed by measuring heart rate response during deep breathing, or heart rate response to standing from lying or seated position (orthostatics), or by changing the orientation of a person's body using, for example, a tilt table. Both sympathetic and parasympathetic activity can be assessed during the Valsalva maneuver (e.g., blowing into a mercury manometer and maintaining a pressure of about or at least about 40 mmHg), or orthostatic heart rate response (e.g., to standing from lying or seated position).

In some embodiments, one, two, or more additional sensors are disposed in the device, including electrical and/or accelerometer sensors in contact with the wearer's skin to measure cardiac activity or pressure sensors to measure changes in blood vessels, to be used in combination with an optical sensor to improve the fidelity of heart rate measurement.

In some embodiments, the system and device have memory and a processor to extract RR intervals from sensor data, calculate variability of RR intervals, transform data into frequency domain, and calculate high frequency signals, low frequency signals, and the ratio of the high frequency and low frequency signals. In some embodiments, the system could store cardiac events, such as arrhythmias, tachycardias, bradycardia, etc.

In some embodiments, the heart rate sensor can store collected data for specified time period to gather adequate date for heart rate variability calculation. Specified time period can range in some cases from 1-60 seconds, and may extend to 10 minutes or more.

In some embodiments, electrodermal activity, also known as galvanic skin response or skin conductance response, for example, can be measured using sensors, such as electrodes; hereafter, galvanic skin response and electrodermal activity are used synonymously. Galvanic skin response is the change of the electrical resistance of the skin caused by emotional stress, and measurable with a sensitive galvanometer. Not to be limited by theory, skin resistance varies with the state of sweat glands in the skin. Sweating is controlled by the sympathetic nervous system, and skin conductance can be an indication of psychological or physiological arousal. If the sympathetic nervous system is highly aroused, then sweat gland activity also increases, which in turn increases skin conductance. In this way, skin conductance can be a measure of emotional and sympathetic responses, and the feedback data can be sent to the controller, which will in turn modulate stimulation to, for example, decrease sympathetic nervous system activity. Other non-limiting parameters associated with sympathetic and/or parasympathetic nervous system activity that can be sensed include, for example, sweating during particular times of the day and/or night, sleep states as detected, for example, by an EEG headband (to determine when sympathetic and/or parasympathetic activity is particularly high or low, and potentially correlating a sleep state such as stage 1, 2, 3, 4, or REM), and/or motion. In some embodiments, a diagnostic and/or combination diagnostic/stimulation device can be configured to measure a person's heart rate and galvanic skin response for improved estimation of the person's autonomic activity; this estimation of autonomic activity can in turn be used to adjust the stimulation applied as treatment, including but not limited to frequency of stimulation, coordination of bursting of stimulation, selected nerve target, duration of stimulation session, or the time of day stimulation is applied. In some embodiments, a wearable device, such as a wrist-worn device can include both electrodermal activity (EDA) sensors and heart rate sensors. This combination of data can in some embodiments advantageously and synergistically provide improved estimation of sympathetic and parasympathetic activity than a single measure alone. In some embodiments, the system can include multiple sensors to measure electrodermal activity in conjunction with heart rate and HRV. Data from the multiple sensors can be analyzed by a hardware or software processor and combined to provide a more accurate estimation of sympathetic and/or parasympathetic activity. In some embodiments, the EDA and HR sensors can be disposed in a wrist-worn device that communicates via a wired or wireless connection to the stimulator or to send data to a centralized remote server (e.g., the cloud). Stimulation parameters, such as frequency or pulse width among others, nerve target locations (e.g., tibial and/or saphenous nerves for example) or dosing regimen (e.g., duration or time of day of stimulation sessions) could be adjusted based on estimations of sympathetic and/or parasympathetic activity. In some embodiments, significant changes in sympathetic and/or parasympathetic activity can be used to predict the onset of a ventricular and/or atrial dyssynchrony or heart rhythm abnormalities, and the device can start stimulation to prevent or reduce the duration of the dyssynchrony event. Adjustments could be made in real-time, or in subsequent stimulation sessions. In some embodiments, stimulation frequency can be adjusted to either increase or decrease autonomic activity modulated by a single specific nerve, or multiple nerves. For example, in some embodiments, relatively low frequency stimulation of a target nerve (e.g., below a threshold value, e.g., about 5 Hz) can potentially inhibit the nerve and thus decreases sympathetic activity, while higher frequency stimulation (e.g., above a threshold value, e.g., about 5 Hz) can potentially excite the nerve and thus increases sympathetic activity. Additionally, pulse width of the stimulation waveform can be adjusted to recruit more or less of a specific fiber type, including cutaneous fibers, which can inhibit sympathetic activity. The same effect can occur with the same or other target nerves to regulate parasympathetic activity. In other words, in some embodiments, relatively low frequency stimulation of the target nerve (e.g., below a threshold value, e.g., about 5 Hz) can potentially inhibit the nerve and thus decreases parasympathetic activity, while higher frequency stimulation (e.g., above a threshold value, e.g., about 5 Hz) can potentially excite the nerve and thus increases parasympathetic activity. Not to be limited by theory, depending on the stimulation parameters for example, in some cases stimulating the target nerve can increase or decrease either sympathetic activity, parasympathetic activity, or both. In some embodiments, stimulation of the saphenous nerve can affect sympathetic activity, and stimulation of the tibial nerve can affect parasympathetic activity.

Not to be limited by theory, some arrhythmias including atrial fibrillation can be triggered by simultaneous discharge of vagal and sympathetic activity, which leads to an imbalance of both arms of the autonomic nervous system. In some embodiments, systems and methods can include assessment of sympathovagal balance using measurements of heart rate variability, galvanic skin response, and arrhythmias, e.g., atrial fibrillation events to determine likelihood of response to peripheral stimulation. For example, a device could be worn on the wrist that combines sensors to measure heart rate, such as optical based sensors, and/or galvanic skin response to assess the sympathovagal balance and detect arrhythmia, e.g., atrial fibrillation events, and a stimulation device. The device could measure HRV and/or GSR and detects atrial fibrillation events over a specified period of time, such as 1-3 days, or 1 week, to adjust stimulation parameters (e.g., stimulation frequency, alternating frequency, duration of stimulation, stimulation time of day) based on an assessment of sympathovagal balance and detection of arrhythmic events. In some embodiments, stimulation of one, two, or more nerves in the upper and/or lower extremity can be combined with stimulation of the auricular branch of the vagus nerve, such as by way of the tragus, to modulate vagal activity and restore balance of the autonomic nervous system. FIG. 3C illustrates select anatomy of the ear 390, including a relatively medial area of the ear 390 generally innervated by the auriculotemporal nerve 399, the tragus 398, the helix 397, the concha 396, an area innervated by the great auricular nerve 395 generally at the inferior and lateral edge of the ear, and an area innervated by the auricular branch of the vagus nerve 394 more centrally and generally in the vicinity of the tragus 398.

Stimulation of the tragus can occur, for example, noninvasively via a plug, earpiece, or other device that can include electrodes for transcutaneous electrical stimulation in some cases. FIG. 3D illustrates an embodiment of a tragus stimulator 392 with an earbud configuration positioned in the tragus 398 of the ear 390. The stimulator 392 can be wired as shown, or wireless in other embodiments. The stimulator 392 can include a distal ear receptacle portion 389 that can include a cathode 387 and an anode 388, a hub 386 proximate the receptacle portion 389, and a conduit 388 to a source of electromagnetic energy, such as electrical energy. In some embodiments, the tragus stimulator 392 includes one or more sensors for measuring parameters relating to stimulation and/or physiologic function as discussed elsewhere herein. The tragus stimulator 392 can be unilateral or bilateral (e.g., placed in both ears).

In some embodiments, a system can include a plurality of stimulators that communicate with each other wirelessly and provided a synchronized, patterned stimulation. In some embodiments, multiple stimulators may be in electrical connection with multiple electrode pairs to stimulate multiple nerves simultaneously. In one embodiment, a system can include a stimulator on the wrist to target median nerve and a stimulator in the ear to target the auricular branch of the vagus nerve. Each stimulator in the system can communicate with each other via a wired or wireless connection. Multiple stimulators can provide synchronized stimulation to the multiple nerves. Stimulation may be, for example, burst, offset, or alternating between the multiple nerves.

The device could also be responsive to number of episodes of symptoms, including chest pain, dyspnea, lightheadedness, and/or palpitations signifying the presence of arrhythmias, cardiac dyssynchrony, and/or abnormal blood pressure in some cases. If more episodes occur in one day, treatment can be increased by increasing the amplitude of the stimulation, duration of the stimulation, or number of treatment sessions, for example.

The number of episodes of symptoms could be detected in various ways to control the stimulation applied by system and devices. In some embodiments, the patient can enter events related to cardiac symptoms, including but not limited to chest pain, dyspnea, lightheadedness, and/or palpitations events on a mobile device.

One embodiment of the system could centrally store biological measures from multiple wearers on a server system (e.g., the cloud), along with other relevant demographic data about each user, including age, weight, height, gender, ethnicity, etc. Data collected from multiple wearers can be analyzed using standard statistical analysis, machine learning, deep learning, or big data techniques, such as a logistic regression or Naive Bayes classifier (or other classifiers), to improve prediction of cardiac dysrhythmia, cardiac dyssynchrony, blood pressure or blood pressure changes by determining correlations between biological measures and other recorded events and cardiac dysrhythmia, cardiac dyssynchrony, and/or increased blood pressure. These correlations can be used to set parameters of the stimulation waveform applied by the therapy unit, determine best time to apply stimulation therapy, and/or adapt the stimulation waveform applied by the therapy unit in real time.

In one embodiment of the system, the wearable monitor automatically detects and records the dosage and consumption of medications to (1) track compliance of the patient; (2) combine with the measurement of cardiac dysrhythmia, cardiac dyssynchrony, and/or blood pressure to assess therapeutic effectiveness, and (3) determine or predict cardiac dysrhythmia, cardiac dyssynchrony, blood pressure or changes in blood pressure. The dosage and consumption of medications can be detected and record in multiple ways, including (1) using visual scanner to record a marking on the pill pack or bottle each time medication is consumed, (2) a smart pill cap with force sensors and a wireless transmitter to detect each time the medication is consumed from a pill bottle, (3) an RFID chip that is of similar size and shape as a pill that is consumed with each dosage of medication that is activated by digestion and communicates with the monitor device, (4) an RFID chip embedded in a sugar pill that is consumed with each dosage of medication that is activated by digestion and communicates with the monitor device, (5) a pill with a visual encoding that is scanned and recorded by a camera on the monitor unit each time medication is consumed, or (6) by having the patient logging drug consumption into the device.

The system can also log the patient satisfaction after each stimulation session or the end of a specified period, like a day or week or month, via an input on the device, which provides another piece of information to help feedback application of therapy. In some cases, if a person is satisfied, the therapy is maintained at the current stimulation waveforms and levels. In other cases, this may mean that the stimulation treatment may need to be optimized, for example, by changing stimulation parameters such as waveform frequency or amplitude.

In some embodiments, the wearable monitor can have a visual, auditory, tactile (e.g., squeezing band), or vibrotactile cues to notify the wearer of key events based on analysis of biological measures, including, but not limited to, prediction of cardiac dysrhythmia, cardiac dyssynchrony, blood pressure or increased blood pressure, and/or increase in stress level, heart rate, heart rate variability, or other parameters. The cuing system could also notify the wearer of other predetermined events or reminders set by the wearer. Cuing system is used to communicate information to the wearer, such as the presence of an arrhythmia such as atrial fibrillation, high blood pressure or other predetermined events, in a more discreet, personalized way, without drawing attention from others in social situations.

In some embodiments, the form of the wearable monitor and/or therapy unit could be a wrist band or watch, a ring, a glove, an arm sleeve or arm band or cuff, knee band, sock, leg sleeve or cuff, an ear piece/headphone, head band, a necklace or neck band, or a compliant patch that conforms to multiple locations on the body.

In one embodiment, the wearable monitor can have a processing unit and memory that collects, stores, processes, and analyzes the biological measures, along with other data input by the wearer.

In some embodiments, the wearable monitor can take user input about events, including diet history, medication history, caffeine intake, alcohol intake, sodium intake, etc. The monitor can use accelerometers to measure specific movements, gestures, or tapping patterns to record user inputs at specific prompts. Other touch sensors, such as resistive strips or pressure sensitive screens, could be used to measure specific gestures to record user inputs. These gesture based measures to record user input minimize the complexity of steps required to input user data into the device. The data can be stored in memory and processed by the processing unit. In some embodiments, the data can be transmitted from the wearable monitor to an external computing device.

In one embodiment, the wearable monitor and/or the therapy unit can connect with other applications, such as calendars and activity logs, to sync and track events or a saved calendar can be saved and stored on the device. In some embodiments, the wearable monitor and/or the therapy unit can communicate with a variety of computing devices, such as a smart phone, a smart watch, a tablet, a laptop computer, or a desktop computer, for example, that have these applications. In some embodiments, the wearable monitor can include an ambulatory blood pressure monitor.

In one embodiment, the monitor unit and/or therapy unit can have a GPS or similar device to track the location and assess activity of the wearer. GPS measures can be combined with mapping or location systems to determine context of the wearer's activity (e.g., gym, office, home) or determine changes in elevation during specific activities, such as running or cycling.

In some embodiments as shown in FIGS. 4A-4D, a single monitor unit 412 can be used with a plurality of therapy units 414 having different sizes, shapes, colors, markings and/or capabilities, which includes different battery capacity and power output. Different wearers and usage scenarios may require different amounts of stimulation duration and power, making a smaller or larger therapy unit more desirable and giving the wearer options to meet their needs in different scenarios. In some embodiments, the therapy units 412 can also have different programming, including different stimulation parameters and/or therapies which can be tailored to different types of treatments. For example, one therapy unit can be tailored to treat cardiac dysrhythmias, cardiac dyssynchrony, while other therapy units can be used to treat hypertension. In some embodiments, the therapy units can each be tailored to provide different intensity of treatments, such as one unit for light treatment of cardiac dysrhythmia, cardiac dyssynchrony, and/or hypertension and another for heavy and aggressive treatment of hypertension, or for various usage patterns or dosing regimens, such as one unit for daily stimulation and one unit for weekly stimulation. The different features and capabilities of the therapy units can correspond to the different sizes, shapes, color, and/or markings. A carrying case 432 can be used to hold a set of therapy units, such as a set of therapy units to treat cardiac dysrhythmia, cardiac dyssynchrony, and/or hypertension that differ in battery capacity and power output or some other feature.

In one embodiment, the therapy units have a unique charging station that can simultaneously charge multiple therapy units. The charging station could have a custom direct electrical connection to the therapy units or could charge the therapy units wirelessly in a close proximity. Similarly, in some embodiments, the charging station can charge the monitoring units in a similar manner.

In one embodiment, the wearable monitor can track parameters about stimulation provided by the therapy unit, including time of stimulation, duration of the stimulation session, and power used by the therapy unit. This data can be stored on memory in the wearable monitor, processed by the wearable monitor, and/or transmitted to an external computing device.

In one embodiment, the therapy unit can use switches or an electrical sensor to detect connection of electrodes: (1) to ensure proper and unique electrodes are being installed (i.e., not using a different or incorrect type of electrode) communicating a unique code, for example via RFID, an encoded EEPROM chip, a resistance or capacitance based ID, a binary identifier, or a surface pattern (2) to regulate the number of uses for each electrode or lifetime of the electrode to prevent over use, and (3) to prevent the usage of the device without an electrode to prevent small shock. In some embodiments, the therapy unit and/or the monitor unit can have an identifier that can be transmitted to and be received by each other or to an external computing device. The identifier can allow one unit to determine the features, capabilities, and/or configuration of the other device, including the electrode configuration described above, so that the appropriate treatment parameters can be used, and also the usage life or expiration of the component, which can be based on voltage measurements, time, number of therapy sessions, or other parameters. In some embodiments, instead of using an identifier, the features, capabilities, and/or configuration of one device can be transmitted to the other device, either directly from one device to the other device, or through entry into the user interface, or through an external computing device.

Other components of the therapy system, including the band, the therapy unit, the monitoring unit, the skin interface, can each have one or more identifiers that performs the functions described above. These identifiers can encode a variety of information as described herein, as well as pre-determined dosing regimens, initialization routines, calibration routines, or specific parameters. The identifiers may be associated with a lookup table that stores the encoded information.

In some embodiments, the wearable monitor and/or the therapy unit can communicate with an external computer or device (e.g., tablet, smartphone, smartwatch, or custom base station that includes a charger and communications connection) to store data. Communication between the monitor and external device can be a direct, physical connection, or with a wireless communication connection such as Bluetooth or GSM or cellular.

In one embodiment of the device, the therapy unit has an array of electrodes and one or more sensors, such as pressure sensors, between the therapy unit and the wearer's wrist to measure contact pressure of the skin interface at and/or around the electrodes. Consistent pressure of the skin interface is especially critical for comfort of dry electrode materials. This pressure data can be analyzed to determine which electrodes in the array stimulate the appropriate nerves or to detect changes in skin contact due to motion or other conditions and switch stimulation of the electrode array to an optimal location. These methods are used to (1) assess poor contact of electrodes, and (2) adjust amplitude of stimulation based on pressure measurement.

Increasing contact pressure between the device and the wearer's skin and/or stimulating with electrodes with an adequate contact pressure or above a contact pressure threshold could: (1) increase the surface area of contact, which reduces discomfort, (2) activate deep somatic pain peripheral nerve fibers, which could reduce discomfort from stimulation, which activates superficial pain fibers, (3) reduce the stimulation amplitude needed because it improves stimulation of the targeted nerve (e.g., the electrode is physically closer to the nerve by compression of the surrounding tissue), or (4) reduce the effect of skin motion.

In some embodiments, specific fiber types within a nerve or nerves can be selectively activated (e.g., create action potentials in such specific fiber types) to restore autonomic balance by specifically modulating sympathetic and parasympathetic limbs of the autonomic nervous system (e.g., selectively only one, or more than one of A-alpha, A-beta, A-delta, B, and/or C fibers). In some embodiments, systems and methods do not stimulate or substantially stimulate A-alpha, A-beta, A-delta, B fibers, or C fibers.

Not to be limited by theory, stimulation of superficial and/or cutaneous afferent and/or efferent nerves can prevent arrhythmias by inhibiting the nucleus of the solitary tract and vagal nuclei, inhibiting the aortic depressor nerve, and thereby the parasympathetic cardiac input; stimulation of deep afferent and/or efferent nerves can prevent arrhythmias by exciting the arcuate nucleus-ventral periaqueductal gray-nuclei raphe pathway, inhibiting the rostral ventrolateral medulla (rVLM) and thereby the sympathetic cardiac input. Superficial fibers are finer (e.g., smaller diameter) afferents that relay sensory information to the superficial dorsal horn, which is a distinct region of the dorsal horn and spinal gray matter; deep fibers are thicker (e.g., larger diameter) afferents that relay sensory information to the deep dorsal horn.

Some embodiments can include preferential stimulation of cutaneous fibers (e.g., A-alpha, A-beta, A-delta, and/or C) fibers to inhibit sympathetic activity of via the stellate ganglion. Stimulation of select cutaneous fibers at the wrist can carry sensory information by way of the medial cutaneous nerve and the medial cord of the brachial plexus, which innervates the spinal cord at the level of C8-T1; stimulation in turn modulates cardiac sympathetic activity by way of the stellate or cervicothoracic ganglion, which are a collection of sympathetic nerves at the level of C7-T1. In some embodiments, peripheral nerve effectors can be positioned, e.g., on the patient's skin such as on the medial side of the forearm as to stimulate the median cutaneous nerve but not stimulate or not substantially stimulate the median, radial, or ulnar nerves, or at least stimulate the medial cutaneous nerve preferentially. In some embodiments, the lateral cutaneous nerve and/or musculocutaneous nerve, or specific fibers thereof can be preferentially or specifically stimulated. In some embodiments, only a single type of nerve fiber is activated, while other types are not activated. For example, in one embodiment, only A-alpha fibers are activated but B fibers are not activated. In one embodiment, 1-5 types of fibers are activated, while leaving one or more fiber types inactivated (or functionally unstimulated). In some embodiments, inactivated fibers do not fire or carry an action potential. In some embodiments, one or more of A-alpha, A-beta, A-delta, B fibers, or C fibers are activated, or not activated. In some embodiments, one or more fibers is preferentially activated, such that a greater number or fraction of one or more fiber types of a particular peripheral nerve is stimulated with respect to other fibers of that peripheral nerve and/or other peripheral nerves proximate the target peripheral nerve. In some embodiments, more than about 50%, 60%, 70%, 80%, 90%, 95%, or substantially all fibers of one or more fiber types of a nerve is activated, while less than about 50%, 40%, 30%, 20%, 10%, 5%, or less of another fiber type is activated, such that there is preferential activation of one or more fiber types with respect to one or more different fiber types of the same nerve and/or other peripheral nerves proximate the target peripheral nerve.

Selective activation of various nerve fiber types can be accomplished in various ways. In some embodiments, stimulation parameters such as pulse width of a biphasic square wave (shown schematically in FIG. 13A) can be controlled to selectively activate specific fiber types (e.g., without activating other fiber types). For example, pulse widths of about 50-100 μs can selectively stimulate larger A-alpha fibers; pulse widths of about 150-200 μs can selectively stimulate smaller A-delta fibers; and pulse widths of about 300-400 μs can selectively stimulate even smaller C fibers.

In some embodiments, frequency of a sine wave pattern (shown schematically in FIG. 13B) can be controlled to selectively activate specific fiber types. For example, frequencies of about 2000 Hz, about 250 Hz, and about 5 Hz can selectively activate A-beta, A-delta and C afferent fibers, respectively.

In some embodiments, a device can include electrodes configured to selectively stimulate superficial nerve fibers (e.g., fibers closer to the surface of the skin) by aligning the electrodes along the length of the nerve axon. FIG. 2A previously described schematically illustrates an example on the wrist. In some embodiments, electrodes of a device can be selectively configured to selectively stimulate deep nerve fibers (e.g., fibers further away from the surface of the skin) by transversely aligning the electrodes across the limb. FIG. 2B previously described schematically shows an example on the wrist.

In some embodiments, a device can include a plurality of electrodes, e.g., four electrodes to where a first electrode pair stimulates at a specified first frequency, f Hz. and a second electrode pair stimulates at a second frequency slightly higher or lower than the first pair, f±x Hz. In some embodiments, the second frequency can be different from that of, but within about ±20%, 15%, 10%, 9%, 8%, 7%, 6%, 5%, 4%, 3%, 2%, or 1% of the first frequency.

In some embodiments, the electrode pairs can be spaced on the limb, as shown in FIG. 13C, such that the stimulation waveforms combine at a specific crossing point to target deep fibers in the limb by creating an interferential pattern of stimulation with a frequency that is the difference between the frequencies of the two waveforms, e.g., x Hz.

Some embodiments can involve stimulation patterns (e.g., bursting, pulse patterns, random, pseudo-random, or noise) selected to improve the efficiency and efficacy of stimulation. In some embodiments, as illustrated schematically in FIG. 13D, an array of electrodes can be aligned along the axon of the nerve that stimulate adjacent pairs of electrodes at regular intervals such that specific points along the nerve are stimulated at a velocity of, for example, between about 1 cm/s and about 10 cm/s. In some embodiments, stimulation can be provided in a bursting pattern where the bursting can either be rhythmic (e.g., at regular intervals) or pseudorandom. In some embodiments, a stimulation waveform can be provided that combines infraslow stimulation frequency (0.01-0.1 Hz) with a higher frequency stimulation (1-200 Hz), or lower frequency (1-200 Hz) with very high frequencies (1000-10 kHz).

In some embodiments, disclosed herein are wearable systems and methods that can utilize transcutaneous sensory stimulation in the form of a burst pattern, e.g., a theta burst pattern to improve cardiac dysrhythmias, cardiac dyssynchrony, hypertension, and/or a variety of other conditions, including but not limited to those disclosed herein. Noninvasive peripheral nerve theta burst stimulation may be effective in some cases in driving cortical or spinal plasticity more efficiently than continuous stimulation to reduce symptoms and improve an individual's quality of life.

In some embodiments, the stimulation involves patterns of electromagnetic stimulation of peripheral nerves. The patterned stimulation could be a bursting stimulation, such as an on/off pattern that repeats at regular intervals (e.g., on for 10 ms, off for 20 ms, etc.), or non-burst patterned stimulation that can be more complex in some embodiments, such as a stochastic pattern or a sinusoidal envelope for example. The electromagnetic stimulation could include, for example, electrical energy, mechanical energy (e.g., vibration), magnetic energy, ultrasound energy, radiofrequency energy, thermal energy, light energy (such as infrared or ultraviolet energy for example), and/or microwave energy, or combinations thereof. In some embodiments, the stimulation is limited to only electrical energy (e.g., no magnetic or other types of energy are applied). The peripheral stimulation could include transcutaneous, percutaneous, and/or implanted stimulation.

In some embodiments, the stimulation involves noninvasive transcutaneous electrical patterned or burst stimulation of peripheral nerves, including afferent and/or efferent nerves. Not to be limited by theory, but burst stimulation of peripheral nerves can unexpectedly result in one or more of the following compared with conventional or continuous stimulation: greater efficacy; greater plasticity; increased tolerance or tolerability; reduced effects of habituation; increased comfort; and/or reduced treatment time required to achieve the same beneficial effects. Burst stimulation of peripheral nerves, including afferent nerves, can in some cases deliver a more efficacious therapy by remotely accelerating plasticity of one or more central nervous system (e.g., brain and/or spinal cord) circuits, in other words creating plasticity in neural circuits for a period of time that is far longer than the duration of the stimulation session, such as, for example, about or at least about 6 hours, 12 hours, 24 hours, 2 days, 3 days, 4 days, 5 days, 6 days, 7 days, 2 weeks, 3 weeks, 1 month, 2 months, 3 months, 4 months, 5 months, 6 months, 9 months, 12 months, 18 months, 24 months, 36 months, or even longer. Peripheral stimulation in some cases can be more convenient and comfortable for the user than central stimulation (e.g., transcranial stimulation and/or spinal stimulation) and can be more suitable for home and ambulatory use.

In some embodiments, the burst stimulation includes theta burst stimulation. Theta burst stimulation (TBS) is a patterned form of repetitive stimulation that uses high frequency pulses separated by varying inter-burst intervals. Originally used for the induction of long term potentiation in hippocampal learning and memory research, theta burst stimulation in the form of repetitive magnetic stimulation (rTMS) has been demonstrated to noninvasively induce plasticity in humans in the motor, sensory and visual cortex. Depending on various parameters including the duration and continuity of stimulation, a long term potentiation or depression (LTP/LTD) like effect can be observed, which are surrogate measures of synaptic efficacy. The number of sessions and the spacing interval between individual sessions of stimulation can also have an effect on the duration of the induced response. The level of muscle relaxation before or during stimulation can also affect the resulting direction or amplitude of plasticity induction suggesting that homeostatic mechanisms are in place that adjust the threshold for plasticity depending on prior synaptic activity. The effective modulation of nervous system plasticity demonstrated with theta burst stimulation can have great potential for the treatment of various neurologic disorders, and can have an effect on other central neural circuits.

In some embodiments, theta burst stimulation can take the form of intermittent theta burst stimulation (iTBS), continuous theta burst stimulation (cTBS), and intermediate theta burst stimulation (imTBS). Non-limiting examples of iTBS, cTBS, and imTBS are illustrated in FIG. 14A. Each illustrate examples of TBS including a burst of 3 stimuli at 50 Hz (20 ms between each stimulus) which was repeated at inter-burst intervals of 200 ms (5 Hz). In the iTBS example pattern, an about 2 second train of TBS is repeated about every 10 seconds for a total of 190 seconds (600 pulses). In the imTBS example pattern, an about 10 second train of TBS is repeated every 15 seconds for a total of 11 seconds (600 pulses). In the cTBS pattern, a 40 second train of uninterrupted TBS is given (600 pulses). The burst pattern (or a combination of two or more burst patterns) can be selected depending on the desired clinical result. In some cases, cTBS can be inhibitory, iTBS can be excitatory, and imTBS can be neither excitatory nor inhibitory, but this may be varied depending on the parameters. In some embodiments, inhibitory stimulation of a first nerve (e.g., the median, ulnar, or radial nerve) can be used alone or in combination with excitatory stimulation of a second nerve (e.g., the median, ulnar, or radial nerve), such as to restore or improve sympathetic and parasympathetic balance. In some embodiments, inhibitory or excitatory stimulation of a nerve can be controlled by adjusting frequency or pulse width of the stimulation waveform.

In some embodiments, each burst can include a plurality of stimuli, such as about or at least about 2, 3, 4, 5, 6, 7, 8, 9, 10, 11, 12, 13, 14, 15, 16, 17, 18, 19, 20, 30, 40, 50, 60, 70, 80, 90, 100, or more stimuli. Each burst can have the same, or a variable number of stimuli.

In some embodiments, the intraburst frequency could be about or at least about 10 Hz, 20 Hz, 30 Hz, 40 Hz, 50 Hz, 100 Hz, 250 Hz, 500 Hz, 1 kHz, or more. In some embodiments, intraburst frequency could vary between about 10 Hz and about 20 KHz. Intraburst frequency can also be varied in a random or pseudorandom fashion during the burst to reduce habituation and/or increase comfort. In other embodiments, the intraburst frequency can be between about 10 Hz and about 250 Hz, between about 50 Hz and about 150 Hz, between about 10 Hz and about 100 Hz, between about 100 Hz and about 150 Hz, between about 50 Hz and about 250 Hz, or between about 50 Hz to about 1000 Hz, in order to maximize tremor reduction, improve comfort, reduce habituation, and/or reduce power consumption of the electrical stimulator device.

In some embodiments, the interburst frequency can be between about 1 Hz to about 20 Hz, such as between about 4 Hz (250 ms between the start of each burst) and about 12 Hz (83 ms), such as between about 4 Hz (250 ms) and about 8 Hz (142 ms) which is generally accepted as the theta band frequency, including about 5 Hz (200 ms), or in some embodiments between about 3.5 Hz and about 7.5 Hz, or between about 6 Hz and about 10 Hz.

In some embodiments, the inter-session frequency can be between about 1 minute and about 12 hours, such as between about 5 minutes and about 120 minutes, between about 5 minutes and about 60 minutes, between about 10 minutes and about 30 minutes, about 5, 10, 15, 20, 25, 30, 35, 40, 45, 50, 55, 60, 75, 90, 120, 180, 240, 300, 360, 420, 480, 540, 600, 660, or 720 minutes, or ranges incorporating any two of the aforementioned values.

In some embodiments, a repetitive patterned stimulation known as quadripulse stimulation could be used, which includes four pulses at a short interval frequency (inter-stimulus interval of 1.5 ms) repeated at about 0.2 Hz for a period of time, such as about 30 minutes. Quadripulse stimulation has been shown to induce prolonged plasticity. Variation of the intraburst frequency using this paradigm can influence the direction of induced plasticity. These repetitive small pulses could be anywhere between 2-10 pulses or more.

Other burst patterns other than theta burst stimulation can also be used, instead or in addition. Some non-limiting examples include delta (0-4 Hz), alpha (8-12 Hz), beta (12-30 Hz), and gamma (30-100 Hz) inter-burst frequencies. In some embodiments, peripheral burst stimulation can include a sinusoidal, square, rectangular, triangular, sawtooth, or other waveform.

In some embodiments, burst transcutaneous peripheral electrical stimulation can be preferred in some cases over burst transcutaneous peripheral magnetic stimulation. In some cases transcutaneous peripheral electrical stimulation can be advantageous because magnetic theta burst can require more power and/or be a heavier device. Electrical stimulation can advantageously provide ambulatory home use, and a more precise stimulation of targeted nerves by controlling flow of current between electrodes or by using a percutaneous needle. In some embodiments, stimulation can be provided at a fixed bursting frequency without measuring for/adjusting for a measured frequency of a physiologic or pathological parameter or symptom associated with a subject.

In one embodiment, the timing of individual sessions of stimulation can be varied in order to prolong the duration of plasticity, as illustrated in FIGS. 14B and 14C. The intersession interval could be between a lower threshold of approximately 1 minute and an upper threshold of approximately 24 hours. Theta burst stimulation intersession interval variation can have a significant effect of varying the spacing intervals between stimulation sessions. Prolongation of the duration of symptom improvement may improve the tolerability of chronic repetitive stimulation. In some embodiments, the intersession interval can be randomized between a lower threshold and an upper threshold. In some embodiments, the intersession interval can increase from a lower threshold or value to an upper threshold or value. In some embodiments, the intersession interval can decrease from an upper threshold or value to a lower threshold or value. In some embodiments, the intersession interval can be varied according to a predetermined algorithm or schedule. In some embodiments, the intersession interval can be varied based on feedback based on data from an accelerometer or electromyography. In some embodiments, the intersession interval can be varied based upon feedback based on tracking symptoms and/or measures of autonomic activity (e.g., HRV, EDA). The interval could also be optimized using machine learning algorithms, such as deep learning, naïve Bayesian networks, neural networks, and/or crowdsourced or otherwise aggregated datasets from multiple users with data (e.g., device usage, symptom tracking, autonomic activity) stored on a remote centralized server (e.g., the cloud).

In some embodiments, alternating stimulation of nerves in the wrist (e.g., radial, median, and/or ulnar nerve) can be performed in a rhythmic pattern or pseudorandom pattern. Not to be limited by theory, bursting at a rhythmic pattern can improve efficiency of therapeutic benefit by promoting plasticity of corticospinal circuits. Rhythmic or pseudorandom bursting patterns can prevent habituation of nerves, which occurs with constant stimulation. In some embodiments, rhythmic bursting patterns can be synchronized to heart rhythm events detected by heart rate monitors in the system, including but not limited to an electrical phase of the cardiac cycle, such as the P wave, R wave, QRS complex, ST segment, T wave, and the like. Not to be limited by theory, alternating bursting stimulation on the medial, radial, and/or ulnar nerves can prevent arrhythmias by having a synergistic effect that increases input to the nucleus of the solitary tract (NTS) in the medulla and influences the activity of NTS neurons projecting to the inhibitory vagal efferent neurons of the dorsal vagal nucleus (DVN) and nucleus ambiguous (NA). These vagal efferent neurons propagate the vagal tone to the sinoatrial node (SA). Alternating bursting stimulation of the medial, radial, and/or ulnar nerves may also excite NTS neurons sending excitatory projections to the caudal ventrolateral medulla (CVLM). The CVLM inhibits the rostroventrolateral medulla (RVLM) which is the primary source of excitatory drive to sympathetic preganglionic neurons in the intermediolateral cell column (IML) of the spinal cord. A schematic of such a reflex loop is illustrated in FIG. 14D. This inhibition could decrease sympathetic activity. This stimulation pattern could improve sympathovagal balance to reduce the burden of cardiac dysrhythmias.

Not to be limited by theory, alternating bursting stimulation on the medial, radial, and/or ulnar nerves can prevent arrhythmias by having a synergistic effect that increases input to stellate ganglion via the brachial plexus to inhibit sympathetic activity or modulate vagal tone via the carotid sinus nerve.

In some embodiments, median, radial, and/or ulnar stimulation can be combined for a synergistic effect at the brachial plexus. The median, radial, and ulnar nerves innervate different levels of the spinal cord at the brachial plexus, with pathways that proceed to different target locations and organs. Some embodiments can provide timed stimulation, either simultaneously or with a delay, to the median, radial, and/or ulnar nerves to control targeting within the brachial plexus to provide a synergistic effect of neural activation at the brachial plexus, which leads to the stellate ganglia and the sympathetic chain. This synergistic effect can provide an advantage of greater therapeutic benefit with less discomfort and less current (e.g., less power for longer battery life). Timing of the stimulation may be simultaneous, or with a delay to account for differences in conduction velocities for the different nerves such that the signals reach the brachial plexus at the same time. Not to be limited by theory, but simultaneous or near simultaneous activation of the brachial plexus can enhance stimulation through the pathway to the stellate ganglia, and increase the effect (e.g., inhibition) of the sympathetic nervous system. For example, the average conduction velocities of sensory nerves of radial, median, and ulnar nerves are about 51 m/s, 60 m/s, and 63 m/s respectively. Based on variation in nerve length from the wrist to the brachial plexus from 1st percentile female to 99th percentile male, this would require a delay in stimulation between the median and radial nerves of about 1.3 to about 1.7 milliseconds, between median and ulnar of about 0.3 and about 0.4 ms, and between radial and ulnar of about 1.6 ms and about 2.1 ms. In some embodiments the delay in stimulation between a first nerve and a second nerve can be between about 0.3 ms and about 1.7 ms, or between about 0.2 ms and about 2.0 ms, between about 1.2 ms and about 2.1 ms, or between about 1 ms and about 2 ms. Lower threshold stimulation on the median, radial, and/or ulnar nerves in combination can advantageously require lower threshold stimulation on the individual nerves with a resultant synergistic effect at the brachial plexus. In some embodiments, a system could include a nerve conduction velocity measurement by applying a stimulation source on a distal portion of the nerve(s) and a measurement electrode on a proximal portion of the nerve(s) to measure an individual's nerve conduction velocities and modify the timed delay based on the individualized measurements.

In some embodiments, a system could include an electrode configuration to stimulate nerves (e.g., radial, median, and/or ulnar) in an alternating pattern that could be rhythmic or pseudorandom. For rhythmic alternating patterns, the alternating frequency can be in a range from 1-100 Hz, which has been shown improve efficiency of therapy by promoting plasticity of corticospinal circuits. In some embodiments, a device embodiment could include an electrode configuration to alternate stimulation of nerves (e.g., radial, median, and/or ulnar) and adjust stimulation parameters (e.g., stimulation frequency, alternating frequency, duration of stimulation, stimulation time of day) based on an assessment of autonomic balance, for example, by measuring heart rate variability (HRV) and analyzing sympathovagal balance as a ratio of absolute low frequency (LF) to absolute high frequency (HF) power, or LF/HF of measured HRV as noted elsewhere herein.

One aspect of the device, as schematically illustrated in FIGS. 14E-14G, is the use of only three electrodes to electrically stimulate two nerves (e.g., median and radial), with an electrode 302, 304 placed on the skin over or proximate to each one of the two nerves 306, 308 and a third charge balance electrode 300 placed on an opposite side of the body part (e.g., wrist) as the two nerves 306, 308. FIG. 14E shows the dorsal side (left) and ventral side (right) of a user's wrist and illustrates an example of the placement of the three electrodes 300, 302, 304 on the user's wrist for targeting two nerves. The three electrodes 300, 302, 304 may all be operatively connected to a single controller 301, as schematically illustrated in FIG. 14E, for regulating the targeted stimulation of the nerves. In some embodiments, the third electrode 300 (e.g., a charge balance electrode) can be placed approximately on the longitudinal midline of the dorsal side of the arm or wrist. In some embodiments, the first electrode 302 can be placed approximately on the longitudinal midline of the ventral side of the arm or wrist to target the median nerve. In some embodiments, the second electrode 304 can be placed in between the charge balance electrode 300 and the ventrally placed electrode 302 to target the radial nerve. In some embodiments, yet another electrode (not shown) can be placed to target the ulnar nerve or an electrode targeting the ulnar nerve can replace either the first electrode 302 targeting the median nerve 306 or the second electrode 304 targeting the radial nerve 308.

FIGS. 14F and 14G illustrate the positions of the charge balance electrode 300, the ventrally placed electrode 302, and the radial electrode 304 in relation to the median nerve 206 and the radial nerve 208 in a distal-looking transverse cross-sectional plane of the patient's wrist or arm. The electrodes 200, 202, 204 are positioned such that in a projection into the transverse cross-sectional plane of the arm or wrist there is a 90 degree to 180 degree angle, al, between a line connecting the median nerve 306 and the center of the charge balance electrode 300 and a line connecting the median nerve 306 and the center of the ventrally placed electrode 303, and there is a 90 degree to 180 degree angle, α2, between a line connecting the radial nerve 308 and the charge balance electrode 300 and a line connecting the radial nerve 308 and the radial electrode 304. The angles α1 and α2 may each be measured in either a counter-clockwise direction (as al is shown in FIG. 14F) or in a clockwise direction (as al is shown in FIG. 14G). More generally, the electrodes 300, 302, 304 can be spaced apart by a predetermined distance such that when the electrodes 300, 302, 304 are positioned circumferentially around a patient's wrist, one of the angles formed between each electrode pair and its target nerve is between about 90 degrees and 180 degrees. Such an orientation results in each electrode of the electrode pair being placed generally on opposite sides of the target nerve. In other words, the target nerve is positioned approximately between the electrode pair.

The effects of an individual stimulation session may be modulated by a priming stimulation session, an example of which is illustrated in FIG. 15. Prior history of synaptic activity may influence the response to a plasticity inducing paradigm according to the Bienenstock-Cooper-Munro (BCM) theory. A priming protocol may vary stimulation waveform parameters, including intensity (e.g., stimulation amplitude), stimulation frequency, duration of stimulation, and/or duration interval between the priming session and stimulation session with subsequent variation in the effects on a subsequent theta burst stimulation session. Waveform parameters may be varied in such a way that are comfortable or increase comfort. Repetitive peripheral nerve stimulation at fixed frequencies may have effects on neural circuit excitability (e.g., motor cortical or spinal reflex circuits) depending on whether the frequency is low (3-10 Hz) or higher (50-200 Hz or more). Depending on the desired effect on brain excitability with burst stimulation, e.g., theta burst, an initial priming session using, e.g., fixed frequency stimulation may allow for controlling the direction or level of plastic effects. In some embodiments, each stimulation session may be preceded by a priming session. In some embodiments, the priming sessions may precede only some but not all of the stimulation sessions, such as every other stimulation session. In some embodiments, the priming session may be delivered based on feedback from a sensor, such as an accelerometer, gyroscope, electromyography, HRV monitor, or EDA sensor. For instance, duration of the priming sessions may increase if the amount of sympathetic activity measured by the sensors is more or less than the average sympathetic activity through the day. The duration of the priming session may be up to as long as the stimulation session duration, or about, at least about, or no more than about 10%, 20%, 30%, 40%, 50%, 60%, 70%, 80%, or 90% or the duration of the stimulation session. In some embodiments, the intraburst frequency of stimulation (201) could be varied to conserve power or improve the efficacy of stimulation. The intraburst frequency can be, for example, as disclosed elsewhere herein.

In some embodiments, a stimulation frequency can be determined by a noise classification, including white noise (all frequencies with equal energy, not dependent on frequency), grey noise (all frequencies with equal loudness, not dependent on frequency), pink noise (power decreases at a rate proportional to $1/f$), red or brownian noise (power decreases at a rate proportional to $1/f^2$), or black noise (power decreases at a rate proportional to $1/f^3$).

In one embodiment, the therapy unit has the form of an inflatable wrist band or arm cuff, which is made of a pliable, airtight material. An inflatable band or cuff is advantageous, especially with a dry electrode or skin interface material, to apply consistent pressure to maintain good contact and conformance between the skin and electrode. A small pump is actuated or activated by the user to fill the bladder with air and increase pressure to increase the surface area of contact, which reduces discomfort. In some embodiments, the pump is integrated into the wrist band and can be either mechanically actuated by the user or electrically powered by a battery. In other embodiments, the pump can be separate from the wrist band. In some embodiments, the band or cuff can include a blood pressure sensor.

Figure 10A:
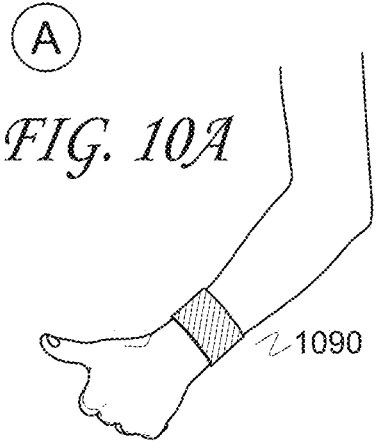
Figure 10B:
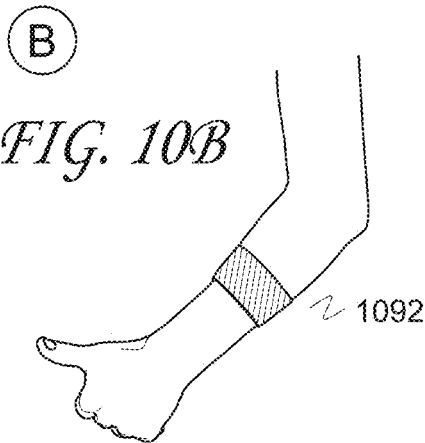
Figure 10C:
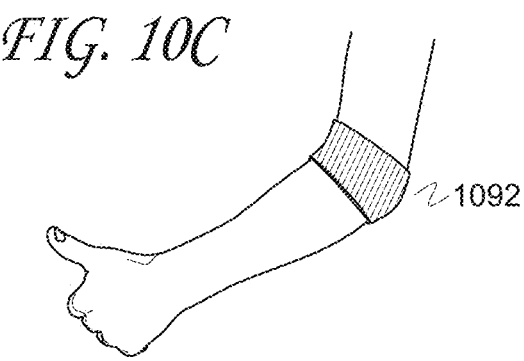
Figure 10D:
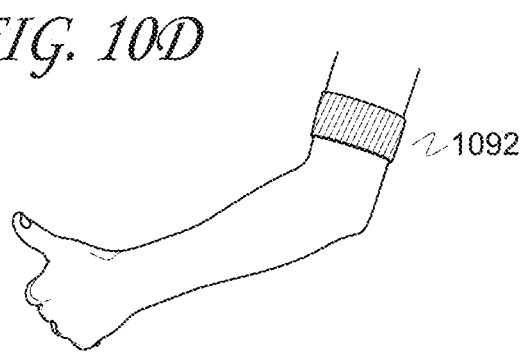

In one embodiment, the therapy unit with the inflatable wrist band or arm cuff has a pressure sensor, such as a piezo-resistive transducer, to measure heart rate, blood pressure, or other cardiac parameters, in addition to the stimulation electronics and electrodes. Other types of cardiac or blood pressure sensors can also be used, such as a microphone to detect the sound of blood flow. The inflatable band or cuff can inflate to a pressure to slow down blood flow in the limb, and then the pressure can be lowered until blood flow is detected by the microphone. The unit could be worn on the wrist, forearm, elbow, upper arm, or under the armpit to find an ideal target for stimulation and blood pressure measurement, as shown in FIGS. 10A-10D. In some embodiments, the system can separate the functions into separate devices. For example, a wrist worn device can be used to stimulate the median nerve, while an arm cuff worn on the arm can be used to measure blood pressure, and a device worn on the torso over the heart can be used to measure heart rate, heart rate variability, and dyssynchrony. FIG. 10A illustrates an embodiment of a wrist band device 1090. FIG. 10B illustrates an embodiment of an arm cuff 1092 on the forearm. FIG. 10C illustrates an embodiment of an arm cuff 1092 at the elbow. FIG. 10D illustrates an embodiment of an arm cuff 1094 under the arm pit or on the upper arm.

In one embodiment, the pressure is provided by a compliant material within the band, such a soft open cell foam or an array of mini springs (e.g., pogo pins).

Figure 5A:
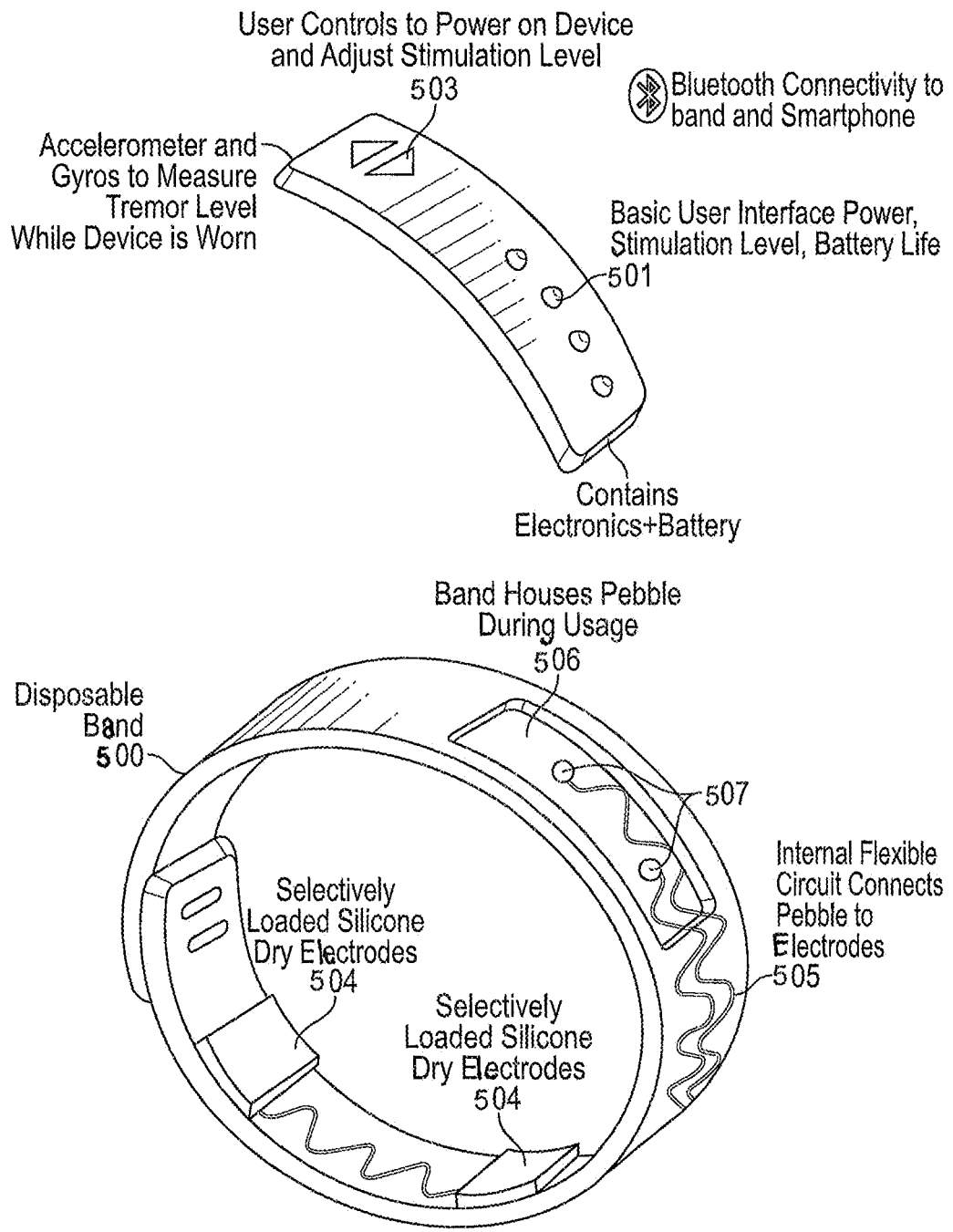
Figure 5F:
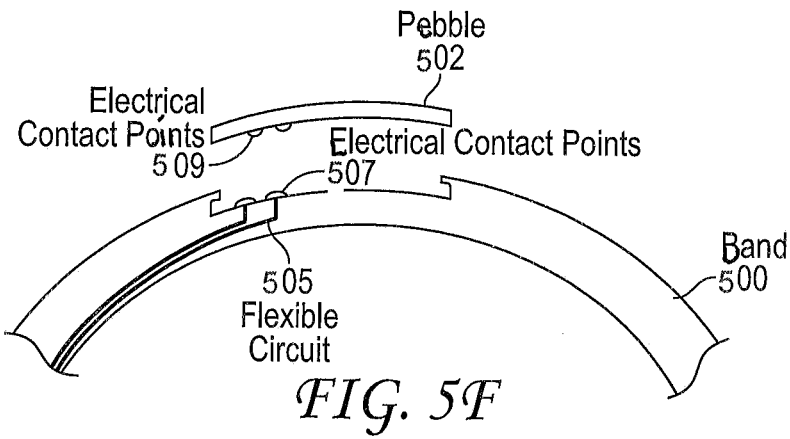
Figure 5G:
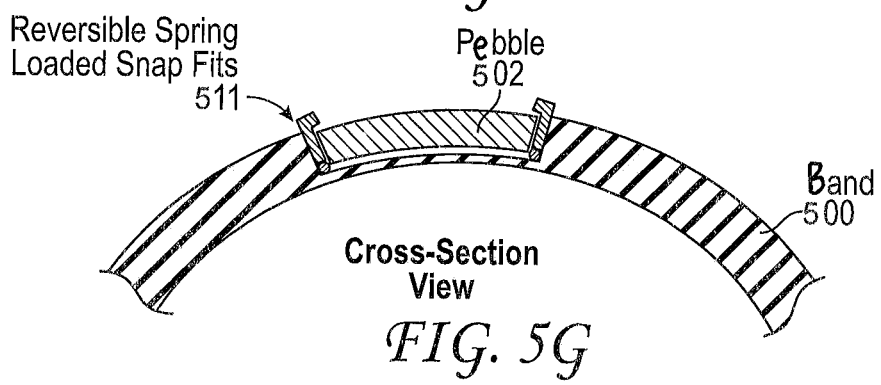
Figure 5H:
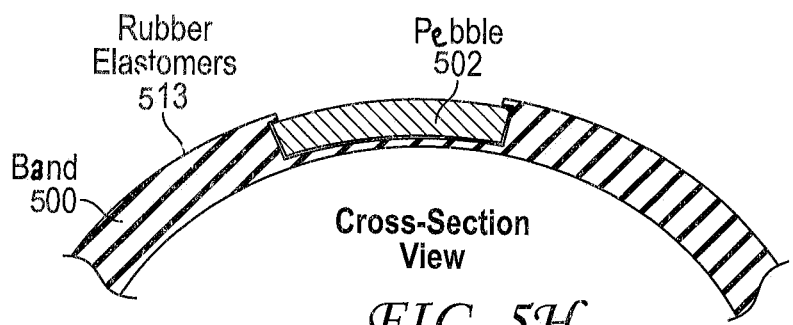
Figure 5I:
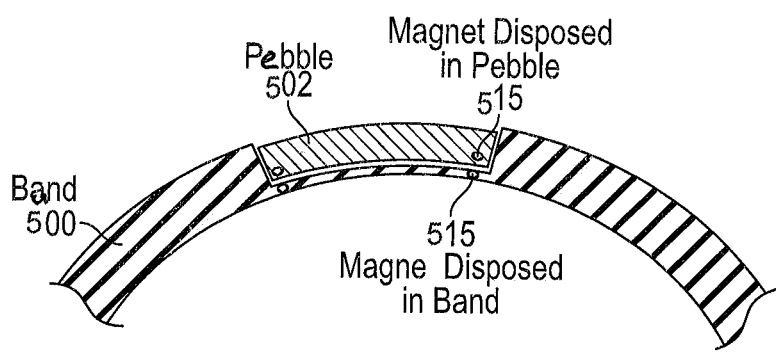

FIGS. 5A-5I illustrates another embodiment of a two part therapy system that includes a disposable band 500 and a therapy unit 502 that can be reversibly attached to the disposable band 500. The disposable band 500 can have two or more electrodes 504 disposed on a skin facing or inside surface of the band and a receptacle 506 or receiving portion for reversibly receiving the therapy unit 502. Within the band 500 are wires and/or conductive traces that form a flexible circuit 505 that runs from the electrodes 504 to the receptacle 506 for electrically connecting the electrodes 504 to the therapy unit 502 when the therapy unit 502 is disposed in the receptacle 506. In some embodiments, the wires and/or conductive traces of the flexible circuit 505 are arranged in a wave or undulating pattern in order to improve its ability to flex. In some embodiments as shown in FIG. 5F, the receptacle 506 can have one or more electrical contact points, such as one or more pin holes 507, for receiving one or more complementary electrical contacts, such as pins 509, from the therapy unit 502. The flexible circuit 505 can extend to the pin holes 507 such that an electrical connection is formed when the pins are inserted into the pin holes. In some embodiments, as shown in FIGS. 5G-5I, the receptacle 506 can have a clip, retaining lip, magnet, a snap fit, a twist fit, a hook, a latch, a sliding mechanism, or other securement feature for reversibly securing the therapy unit 502 to the band 500. FIG. 5G illustrates clips 511 that may or may not be spring loaded to form a snap fit around the therapy unit 502. FIG. 5H illustrates a flexible lip 513 around the opening of the receptacle that can be used to retain the therapy unit 502 after it is inserted into the receptacle 506. FIG. 5I illustrates magnets 515 that can be placed in complementary positions in the therapy unit 502 and the receptacle. In some embodiments, the clip, magnet, snap fit mechanism, twist fit mechanism, hook, or other securement feature is made of metal or some other conductive material and can be electrically connected to the electrodes via the wires and/or conductive traces. The electrodes 504 can be dry electrodes or can be coated with a conductive gel.

In some embodiments, the therapy unit 502 can include a battery, which may be rechargeable, and electronics to deliver electrical stimulation through the electrodes to the patient's nerves. The electronics can include a stimulator and a microcontroller, and may also include memory and one or more sensors, such as a blood pressure sensor and/or a sensor to measure heart rate and/or heart rate variability and/or galvanic skin response, or one, two, or more ECG electrodes to measure dyssynchrony. In some embodiments, the device is able to sense the impedance of the electrodes in order to assess the integrity of the electrode to skin interface. In some embodiments, there can be an electrical indication (e.g. reading of a chip, pushing in of a sensor on the connector, etc.) to detect integrity of the connection between the band and the therapy unit. In some embodiments, the therapy unit 502 can have one or more LEDs, mini OLED screens, LCS, or indicators 501 that can indicate the status of the therapy unit 502, such as whether the therapy unit 502 is connected to the band 500, the power remaining in the battery of the therapy unit 502, whether a stimulation is being delivered, the stimulation level, whether data is being transmitted, whether a sensor measurement is being taken, whether a calibration routine is being performed, whether the therapy unit 502 is initializing, whether the therapy unit 502 is paired with another device such as a smart watch and/or smart phone, whether the battery is being charged, and the like. In some embodiments, the therapy unit 502 may also include a user interface 503, such as one or more buttons.

FIG. 5B illustrates a kit including a wrist worn device that can be sent to a user. The kit can contain a plurality of bands 500 of different sizes, shapes, colors, etc. to accommodate patients having different wrist sizes or other body part sizes, such as ankles, arms, fingers, and legs and to accommodate different types of connected accessories like secondary displays (e.g. smart watch). In some embodiments, the kit has three bands to accommodate a majority of wrist sizes. In some embodiments, the kit has two bands to cover most sizes. Additionally, the kit can contain one or more electronic units 502. If multiple electronic units 502 are provided in the kit, the battery capacity of the different electronic units 502 can be different to accommodate different usage types. For example, a relatively low capacity battery can be used for on-demand stimulation, while a relatively high capacity battery can be used for automated and/or responsive stimulation driven by the microcontroller. In some embodiments, only a single electronic unit is provided. In other embodiments, a plurality of electronic units are provided while a single band is provided. The kit may also include a charger 508 to charge the therapy unit 502. In some embodiments, the charger 508 can inductively charge the therapy unit 502. In other embodiments, the charger 508 can charge the therapy unit with a charge cable that can be inserted into a power port in the therapy unit. In some embodiments, the therapy unit 502 can be docked with the charger 508 for charging.

FIG. 5C illustrates an embodiment where a smart watch 510, such as the Apple Watch, is reversibly or permanently fastened to a band 500, which may also have a therapy unit 502. In some embodiments, the smart watch 510 may provide a display and a user interface for the therapy unit 502. The smart watch 510 may communicate with the therapy unit 502 wirelessly, such as through Bluetooth or Wi-Fi, or through a direct connection through a data port in the smart watch and a data port in the therapy unit 502. In some embodiments, the electronic unit 502 and/or smart watch 510 may communicate with a smart phone 512, as described herein, to transmit data or to update the software and/or stimulation parameters on the therapy unit 502 and/or smart watch 510. In some embodiments, the band 500 and therapy unit 502 are permanently affixed or integrated together while the smart watch 510 is reversibly attachable to the band 500. The smart phone 512 and/or the smart watch 510 can include an application, which may be downloaded through the cloud or a computer, configured to interface with the therapy unit 502.

FIGS. 5D and 5E illustrate that the wearable two part system can be worn and used throughout the day. When the power remaining in the battery of the therapy unit is low, the therapy unit 502 can be recharged with the charger 508. Charging can be performed at night or whenever the battery is low or when desired. In some embodiments, the therapy unit can be removed from the band before charging. In some embodiments, the user can swap a low charge therapy unit with a high charged therapy unit so that the user can always be wearing a therapy unit.

In some embodiments, the kit illustrated in FIG. 5B can be used as a diagnostic trial kit. The patient can initially wear the therapy system for about, at least about, or no more than about 1 day to about 90 days, or about or at least about 1, 2, 3, 4, 5, 6, 9, 12, or more months, or for a predetermined length of time. This initial period is used to collect data with the sensors in the therapy unit and/or band in order to characterize the cardiac rhythm, blood pressure profile, or other related measures, or other disease, and assess the patient's response to the therapy during the trial period in order to identify how well the patient is responding to the various treatments. The sensor data can be stored in memory in the therapy unit, and/or can be transmitted through a network to the cloud or a server or to another computing device, which can be accessed by the patient's physician, the company, or another third party.

Additional specific examples of methodologies that can treat a disorder relating to cardiac dysfunction by restoring balance to sympathetic and parasympathetic nervous system activity, including but not limited to reducing sympathetic and/or parasympathetic nervous system activation relating to neural cardiac circuits, are disclosed herein.

FIG. 16A illustrates a flow chart of an example of a therapeutic protocol for treating cardiac dysrhythmias, hypertension or other cardiac dysfunction, according to some embodiments of the invention. Any number of the steps can be performed automatically by a device that includes a memory and a processor for receiving feedback information and execution of such steps. In some embodiments, sympathetic and parasympathetic activity can be assessed during a baseline period (e.g., from about 24 hours to about 30 days in some embodiments) using sensors that measure heart rate, heart rate variability, and/or electrodermal activity 1600. Heart rate and HRV can be measured in various ways and sympathetic overactivation or underactivation assessed 1602, including an optical sensor in a wrist worn device, a chest strap or patch that measures changes in electrical activity, a pulse oximeter worn on the finger, and the like. Sympathetic and parasympathetic activity can also be measured using electrodermal activity sensors as described elsewhere herein. In some embodiments, a single device can include both an optical heart rate sensor and electrodermal activity sensors to improve the estimation of sympathetic and parasympathetic activity. If abnormal sympathetic activity is identified (e.g., from HRV and/or other autonomic measurements), median, ulnar, or radial nerve stimulation can be initiated (or stimulation of other nerves, e.g., as disclosed herein associated with sympathetic activity) 1604. If abnormal parasympathetic activity is identified, tragus nerve stimulation (or stimulation of other nerves, e.g., as disclosed herein associated with parasympathetic activity) 1606 can be initiated. After a period (e.g., about 1-4 weeks) of stimulation, a controlled measure of autonomic function, e.g., HRV, can be reassessed 1607.

In some embodiments, sympathetic and parasympathetic activity are assessed prior to initial stimulation to select specific nerve targets, stimulation waveforms, stimulator parameters, or dosing of stimulation (e.g., time of day, duration of stimulation, number of times per day or week). In other methods, a default stimulation 1608 is applied in a trial fashion, and HRV can be measured and symptoms tracked during a select period of therapy (e.g., for about 1-4 weeks) 1609. If there is an acceptable therapeutic response the therapy is continued 1610, and only if a person does not respond to treatment is sympathetic and parasympathetic activity assessed 1612, as illustrated in FIG. 16B and FIG. 16C. If abnormal parasympathetic activity is identified, tragus nerve stimulation (or stimulation of other nerves, e.g., as disclosed herein associated with parasympathetic activity) 1614 can be initiated. If abnormal sympathetic activity is identified despite median nerve (or stimulation of other nerves, e.g., as disclosed herein associated with sympathetic activity), stimulation parameters of the median nerve can be modified 1618. HRV or other parameters can then be measured during a subsequent period of therapy 1620, e.g., about 1-4 weeks in some cases). In other methods, sympathetic and parasympathetic activity are assessed over a single day or over multiple days during an initial period of treatment to measure any changes in autonomic activity.

In some embodiments, if a person does not respond to therapy, a number of parameters can be altered to modify therapy, including but not limited to increasing or decreasing, or otherwise changing any number of the following: duration of session (e.g., 20-120 minutes); number of sessions per day or week (e.g., 2 times per day to 3 times per week); time of day or night of stimulation; stimulation frequency; bursting or other stimulation pattern (including bursting frequency); nerve target (e.g., median or tragus); and/or stimulation amplitude.

FIG. 17 schematically illustrates a diagnosis, assessment, and prescription flow chart for a subject with cardiac dysfunction, according to some embodiments of the invention. A physician can diagnose a subject, and then utilize an assessment kit, which can include an autonomic nervous system activity monitoring device, such as a continuous or intermittent wrist-worn HRV monitor for example, and an application for tracking cardiac symptoms, including AF events. The physician can review the assessment data and prescribe customized therapy based on the assessment data.

In some embodiments, the frequency and duration of treatment sessions or the properties of the waveform applied by the therapy unit (e.g., pulse width, frequency, and amplitude) could be adjusted based on measurements and data collected and stored by the therapy system. For example, the frequency of treatment sessions could be increased if cardiac dysrhythmia, cardiac dyssynchrony, and/or blood pressure measurements, collected and stored daily by the device, are above a specific threshold. Once the cardiac dysrhythmia, cardiac dyssynchrony, and/or blood pressure drops below the threshold, the frequency of treatments can decrease, as shown in FIG. 9A. Multiple thresholds could be established based on existing classifications of cardiac dysrhythmia and/or cardiac dyssynchrony, including but not limited to variability in the R wave-to-R wave (RR) interval (also referred to as heart rate variability). For example, stimulation may be applied or a parameter modified when the RR interval increases above a specific threshold, for example. Multiple thresholds can also be established, for example, based upon existing classifications of hypertension or atrial fibrillation, for example, as described in the table below.

TABLE 1

| Top number (systolic) in mm Hg | Bottom number (diastolic) in mm Hg | Hypertension category* |
|---|---|---|
| Below 120 | and Below 80 | Normal blood pressure |
| Between 120-139 | or Between 80-89 | Prehypertension |
| Between 140-159 | or Between 90-99 | Stage 1 hypertension |
| 160 or higher | or 100 or higher | Stage 2 hypertension |

For atrial fibrillation, metrics can include atrial fibrillation symptom score or atrial fibrillation burden, which can be an aggregate of duration, frequency, and other burden variables. Metrics can also include, for example, stroke risk factor scores associated with atrial fibrillation including a CHADS score, e.g., the CHA2DS2-VASc score, taking into account any number of stroke risk factors such as, for example, the presence or absence of congestive heart failure, hypertension, age greater than or equal to 75 years, diabetes mellitus, prior stroke, TIA, or thromboembolic event, vascular disease (e.g., peripheral arterial disease, myocardial infarction, aortic plaque), age 65-74 years; or sex category (e.g., male or female sex).

In some embodiments, cardiac dysrhythmia and/or cardiac dyssynchrony measurements can be measured with a sensor at or near the chest, or on the wrist, including but not limited to radial pulse, or dorsalis pedis or posterior tibial pulses in the feet.

In some embodiments, a cardiac monitor can detect bradycardia and adjust parameters of the stimulation, such as amplitude or frequency, or the duration or number of times stimulation is applied, in a closed-loop system. Bradycardia can arise if vagal tone is increased too much, thus the goal can be in some cases to limit overstimulation.

In some embodiments, the patient can return the kit to the physician or manufacturer of the kit, and data can be retrieved from the system and transmitted to the patient's physician.

Using the data from the system, the physician can characterize the patient's cardiac dysrhythmia or cardiac dyssynchrony, or hypertension, blood pressure or other disease, generate a diagnosis, and determine the appropriate treatment for the patient, which may include selection of the appropriate therapy system and stimulation parameters, and/or changes in medication.

FIG. 6 illustrates an embodiment of a system for treating hypertension or another disease or condition using a wearable therapy device. As described above, the therapy device may have two parts, a band 500 and therapy unit 502. A base station 600, which may replace the charger in the kit described above, can be used to both charge the therapy device and to receive and transmit data to the therapy device and to the cloud 602. Communication between the base station 600 and the therapy device can be wireless, such as through Bluetooth and/or Wi-Fi, and communication between the base station 600 and the cloud 602 can be through a cellular network, using a 3G or 4G connection, or through a wired connection to the internet, using DSL or cable or Ethernet, for example. A physician or other user can view and/or retrieve data stored on the cloud 602 using an online portal or a physician web portal 604. In addition, the physician can prescribe and/or modify a treatment regimen on the therapy unit 502 through the cloud 602 and base station 600 using the web portal 604.

In some embodiments, the base station 600 is used to receive and transmit relatively large amounts of data that may require a high bandwidth, such as the transmission of raw data from the therapy device, which may be about 10 to 100 Mb/day, or about 10, 20, 30, 40, or 50 Mb/day. In some embodiments, the data may be stored in memory in the base station 600 and transmitted at another interval, such as weekly or twice weekly, with a scaling up of the bandwidth of transmission. The high bandwidth transmission of the raw data can occur daily while the therapy device is being charged, such as at night during a regular charging period. In some embodiments, the raw data can be processed by the cloud and/or the physician into processed data and sent back to the therapy device.

In some embodiments, the system may optionally include a portable computing device 606, such as a smart phone or tablet, to provide a secondary display and user interface for the patient and to run applications to more easily control the therapy device and view the raw and processed data. The portable computing device can be used to make patient or physician adjustments to the therapy device, such as adjusting the stimulation parameters and dosing, and can receive device state data from the therapy device, which includes data relating to the device, such as when the device was used, errors, therapy parameters such as amplitude and when they were set and delivered. In some embodiments, the portable computing device 606 can receive processed data from the cloud 602 through a cellular network and/or through an internet connection using Wi-Fi, for example.

FIG. 7 illustrates the various components that can be included in a therapy unit 700, band 702, and base station 704. These components are described in detail above and also below as one particular embodiment. For example, the therapy unit 700 includes one or more indicators 706, which can be LEDs, and a user interface 708, which can be push buttons, for example. The therapy unit 700 can also have a stimulator 710 with stimulation electronics and may include the capability to measure current and voltage. The therapy unit 700 can also have a battery 712, which may be rechargeable and can be recharged using charging circuitry 714, which may be inductive. The therapy unit 710 may further include a processor 716 and memory 718 to store and execute programs and instructions to accomplish the functions described herein. The therapy unit 710 may also include sensors 720, such as blood pressure sensors, and a communications module 722, which may be wireless and can communicate with the base station 704 and/or a secondary display/computing device.

The band 702 can have electrodes 724 and may also include memory to store identification information or may include some other form of identifier 726 as described herein.

The base station 704 can include charging circuitry 728, which may also be inductive and can transmit power to the complementary charging circuitry 714 on the therapy unit 700. The base station 704 can also have a processor and memory for storing and executing instructions and programs. The base station 704 can further include a communication module 732, which may be cellular, to communicate with the cloud, and another communication module 734, which may be wireless and used to communicate with the therapy unit.

In some embodiments, the device can be a heart rate monitor, ECG monitor, or other cardiac monitor worn on the body, or a blood pressure cuff, each which could include an integrated nerve stimulator. In some embodiments, the nerve stimulator and cardiac monitor and/or blood pressure device can be separate devices that communicate wirelessly. In some embodiments, the device can measure cardiac rhythm and/or blood pressure over the course of minutes, hours, days, weeks and/or months to determine whether the patient's cardiac dysrhythmia, cardiac dyssynchrony, and/or blood pressure is increasing, decreasing, or staying the same. In some embodiments, the cardiac rhythm and/or blood pressure measurements are time averaged over a window, which can be days, weeks, or months. In some embodiments, a sensor, such as a motion sensor, IMU, or GPS, can be used to detect patient activity, which can affect cardiac rhythm and/or blood pressure measurements. In some embodiments, cardiac rhythm and/or blood pressure measurements are not taken when the patient is active. In some embodiments, cardiac rhythm and/or blood pressure measurements are only taken when the patient activity sensors determine that the patient is at rest. In some embodiments, the sensor can be an electrode that measures galvanic skin response, which can be correlated to stress, and changes in cardiac rhythm, blood pressure, and/or sympathetic activity. In some embodiments, cardiac rhythm and/or blood pressure is measured at the same time each day with the same conditions to improve measurement consistency and to reduce variability. In some embodiments, the stimulator is applied to one wrist or arm to stimulate one peripheral nerve in the arm, such as the median nerve, or specific nerve location, such as an acu-pressure point or meridians.

In other embodiments, a stimulator is applied to both wrists/arms to bilaterally stimulate the nerves in the wrist and/or arm, such as median nerves or acu-pressure points, as shown in FIG. 11. In some embodiments, the device can be worn around the wrist, the forearm, or the upper arm, or the leg below the knee, above the knee, or near the ankle or in the car or on the tragus. In some embodiments, the two bilateral devices can be operated simultaneously to stimulate both nerves at the same time. The stimulation parameters for each device may be the same, or may differ. The two devices may be in communication wirelessly to synchronize or offset the waveforms between to devices. The waveforms may be offset to affect pacing of the heartbeat (i.e., timing of the contractions of the left and right ventricle) to improve dyssynchrony, arrhythmia, or contractile properties of heart tissue, etc., associated with heart failure. In some cases, pacing of heart rhythm may be achieved by affecting neural dynamics associated with the vagus nerve or by direct electrical activity of the heart. In some embodiments, the two bilateral devices can be operated in an alternating fashion such that only one device delivers stimulation at a time. The alternating devices can alternate stimulation on an hourly, daily, weekly, or monthly basis; and the frequency of the alternation can be modified based on measures of blood pressures.

In some embodiments, the stimulation parameters of the devices described herein are an amplitude of between about 1 mA to about 20 mA, such as between about 1 mA to about 10 mA, or between about 2 mA to about 5 mA. In some embodiments, the frequency can be between about 1 Hz to about 100 kHz, between about 1 Hz and about 150 Hz, or between about 1 Hz and about 10 Hz. In some embodiments, the pulse width can be from about 10 µS to about 1000 µs. In some embodiments, the pulse spacing can be from about 0 µS to about 1000 µs. In some embodiments, the frequency may be a high frequency stimulation, and include frequencies from about 100 Hz to about 100 kHz. In some embodiments, the stimulation waveform is biphasic (i.e., positive portion of a pulse is followed, substantially immediately, by a negative portion of the pulse or vice-versa) or monophasic square wave, sine wave, triangle wave, or other shapes Other embodiments can include curved waveforms where there can be a ramp-up and/or ramp-down period to or from maximum amplitude. In some embodiments, the stimulation is symmetric or asymmetric. In some embodiments, the asymmetric waveform can be configured to be charge balanced such that the area under the positive-going pulse can be equal to the area under the negative-going pulse. In some embodiments, the leading pulse has a positive polarity or a negative polarity.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description. The methods disclosed herein include certain actions taken by a practitioner; however, they can also include any third-party instruction of those actions, either expressly or by implication. For example, actions such as "percutaneously stimulating an afferent peripheral nerve" includes "instructing the stimulation of an afferent peripheral nerve."

What is claimed is:

1. A transcutaneous method for treating at least one of cardiac arrhythmias and hypertension with selective activation, comprising:
   positioning a first peripheral nerve effector on a patient's skin on an extremity of the patient;
   positioning a second peripheral nerve effector on the patient's skin on the extremity of the patient;
   delivering a first electrical nerve stimulation signal transcutaneously to the first peripheral nerve effector to stimulate a first peripheral nerve relating to the cardiac arrhythmia or hypertension; and
   delivering a second electrical nerve stimulation signal transcutaneously to the second peripheral nerve effector to stimulate a second peripheral nerve relating to the cardiac arrhythmia or hypertension,
   wherein the first and the second peripheral nerves are selected from the group consisting of one or more of: a median nerve, a radial nerve, and an ulnar nerve,
   wherein the first electrical nerve stimulation signal activates an A-alpha fiber and a C-fiber of the first peripheral nerve,
   wherein the second electrical nerve stimulation signal activates an A-alpha fiber and one or more of: A-delta or C-fibers of the second peripheral nerve,
   wherein the second peripheral nerve is different from the first peripheral nerve, and
   wherein the method does not utilize any implantable components, and only involves transcutaneous stimulation.

2. The method of claim 1, further comprising positioning a third peripheral nerve effector on a tragus of an ear of the patient; and delivering a third electrical nerve stimulation signal transcutaneously to the third peripheral nerve effector to stimulate a third peripheral nerve relating to the cardiac arrhythmia or hypertension of the patient.

3. The method of claim 1, wherein the first electrical nerve stimulation signal further includes activation of A-beta fibers of the first peripheral nerve.

4. The method of claim 1, wherein the first electrical nerve stimulation signal preferentially activates A-delta fibers of the first peripheral nerve.

5. The method of claim 1, wherein the first electrical nerve stimulation signal preferentially activates C fibers of the first peripheral nerve.

6. The method of claim 1, wherein the first electrical nerve stimulation signal comprises a frequency of about 2,000 Hz.

7. The method of claim 1, wherein the first electrical nerve stimulation signal comprises a frequency of about 250 Hz.

8. The method of claim 1, wherein the first electrical nerve stimulation signal comprises a frequency of about 5 Hz.

9. The method of claim 1, wherein the first peripheral nerve effector comprises a first electrode and a second electrode, and wherein the method further comprises positioning the first electrode and the second electrode such that they are substantially aligned along a length of a nerve axon.

10. The method of claim 1, wherein the second electrical nerve stimulation signal affects parasympathetic or sympathetic nervous system activity of the patient.

11. The method of claim 1, further comprising receiving an input relating to autonomic nervous system activity of the patient.

12. The method of claim 11, wherein receiving an input relating to autonomic nervous system activity of the patient comprises receiving data from a sensor that measures heart rate variability of the patient.

13. The method of claim 11, wherein receiving an input relating to autonomic nervous system activity of the patient comprises receiving data from a sensor that measures at least one of electrodermal activity, thermometry, and ECG information of the patient.

14. The method of claim 1, wherein both the first and second peripheral nerve are related to the cardiac arrhythmia.

15. The method of claim 1, wherein delivering the second electrical nerve stimulation signal is offset temporally from delivering the first electrical nerve stimulation signal.

16. A wearable transcutaneous system for treating cardiac arrhythmias or hypertension with selective activation, comprising:
   a controller;
   a first peripheral nerve effector configured to be positioned on a patient's skin on an extremity of the patient;
   a second peripheral nerve effector configured to be positioned on the patient's skin on the extremity of the patient; and
   at least one sensor or data input source configured to provide biological information;

wherein the controller is configured to generate a first electrical nerve stimulation signal transcutaneously to the first peripheral nerve effector to stimulate a first peripheral nerve relating to the cardiac arrhythmia or hypertension, wherein the controller is configured to generate a second electrical nerve stimulation signal transcutaneously to the second peripheral nerve effector to stimulate a second peripheral nerve relating to the cardiac arrhythmia or hypertension, wherein the first and the second peripheral nerves are selected from the group consisting of one or more of: a median nerve, a radial nerve, and an ulnar nerve, wherein the first electrical nerve stimulation signal activates an A-alpha, and a C-fiber of the first peripheral nerve, wherein the second peripheral nerve is different from the first peripheral nerve, and wherein the system does not utilize any implantable components.

17. The system of claim 16, wherein both the first and second peripheral nerve are related to the cardiac arrhythmia.

18. The system of claim 16, wherein the second electrical nerve stimulation signal activates one or more of: A-delta or C-fibers.

19. The system of claim 16, wherein the biological information comprises heart rate variability.

20. The system of claim 16, wherein the biological information comprises galvanic skin response.

21. The system of claim 16, wherein the first electrical nerve stimulation signal further includes activation of A-beta fibers of the first peripheral nerve.

* * * * *